United States Patent
Toma et al.

(10) Patent No.: US 8,460,269 B2
(45) Date of Patent: Jun. 11, 2013

(54) DIRECTED CELL-BASED THERAPY USING MICROBUBBLE TAGGED CELLS

(75) Inventors: Catalin Toma, Pittsburgh, PA (US); Flordeliza Villanueva, Pittsburgh, PA (US); William Richard Wagner, Wexford, PA (US); Joon S. Lee, Pittsburgh, PA (US); Jianjun Wang, Glenshaw, PA (US); Xucai Chen, Glenshaw, PA (US); Andrew Fisher, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 33 days.

(21) Appl. No.: 12/880,807

(22) Filed: Sep. 13, 2010

(65) Prior Publication Data

US 2011/0208113 A1 Aug. 25, 2011

Related U.S. Application Data

(60) Provisional application No. 61/242,099, filed on Sep. 14, 2009.

(51) Int. Cl.
*A61M 31/00* (2006.01)
(52) U.S. Cl.
USPC ........... 604/500; 604/22; 435/177; 424/93.7; 424/723
(58) Field of Classification Search
USPC ............... 604/22; 424/93.7–93.73, 400, 422, 424/423; 435/174, 177
See application file for complete search history.

(56) References Cited

U.S. PATENT DOCUMENTS

| | | | |
|---|---|---|---|
| 4,586,512 A | 5/1986 | Do-huu et al. | 600/447 |
| 4,620,546 A | 11/1986 | Aida et al. | 600/439 |
| 4,658,828 A | 4/1987 | Dory | 600/439 |
| 5,558,092 A | 9/1996 | Unger et al. | 600/439 |
| 5,980,551 A | 11/1999 | Summers et al. | 606/194 |
| 6,416,740 B1 | 7/2002 | Unger | 424/9.52 |
| 7,358,226 B2 * | 4/2008 | Dayton et al. | 514/1.2 |
| 2003/0185870 A1 * | 10/2003 | Grinstaff et al. | 424/423 |
| 2004/0191225 A1 * | 9/2004 | Dinsmore et al. | 424/93.7 |
| 2008/0200862 A1 * | 8/2008 | Unger et al. | 604/22 |
| 2008/0305156 A1 * | 12/2008 | Laing et al. | 424/450 |
| 2008/0312581 A1 * | 12/2008 | Hardy | 604/22 |

OTHER PUBLICATIONS

Aggarwal, S. and Pittenger, M. F. (2005) Human mesenchymal stem cells modulate allogeneic immune cell responses, *Blood* 105(4), 1815-1822.

(Continued)

*Primary Examiner* — Emily Schmidt
(74) *Attorney, Agent, or Firm* — Medlen & Carroll, LLP

(57) ABSTRACT

The disclosed technology describes compositions and methods useful for providing cell based therapy. For example, one embodiment of cell based therapy involves the regeneration of injured tissue and/or promoting wound healing. Certain embodiments provide improved therapeutic compositions using microbubbles by delivering biological progenitor cells to the injured tissues. The administration of the microbubbles is directed by acoustic radiation forces that interact with embodiments of microbubbles comprising an acoustically active gas. As such, a high efficiency of progenitor cell delivery to injured tissue is realized. One advantage of this technique over targeted delivery of pharmaceutical compounds, is that the delivered progenitors cells may be derived from the patient (i.e., personalized therapy), thereby avoiding side effects, allergic reactions, and overall problems associated with refractive drug responses.

11 Claims, 18 Drawing Sheets

OTHER PUBLICATIONS

Alkan-Onyuksel, H. et al. (1996) Development of inherently echogenic liposomes as an ultrasonic contrast agent, *Journal of Pharmaceutical Sciences* 85(5), 486-490.

Aoki, J. et al. (2005) Endothelial Progenitor Cell Capture by Stents Coated With Antibody Against CD34: The HEALING-FIM (Healthy Endothelial Accelerated Lining Inhibits Neointimal Growth-First in Man) Registry, *Journal of the American College of Cardiology* 45(10), 1574-1579.

Behrendt, D. and Ganz, P. (2002) Endothelial function: From vascular biology to clinical applications, *The American Journal of Cardiology* 90(10, Supplement 3), L40-L48.

Blindt, R. et al. (2006) A Novel Drug-Eluting Stent Coated With an Integrin-Binding Cyclic Arg-Gly-Asp Peptide Inhibits Neointimal Hyperplasia by Recruiting Endothelial Progenitor Cells, *Journal of the American College of Cardiology* 47(9), 1786-1795.

Borden, M. A. et al. (2006) Ultrasound Radiation Force Modulates Ligand Availability on Targeted Contrast Agents, *Molecular Imaging* 5(3), 139-147.

Caplan, A. I. and Dennis, J. E. (2006) Mesenchymal stem cells as trophic mediators, *Journal of Cellular Biochemistry* 98(5), 1076-1084.

Chen, X. and Apfel, R. E. (1996) Radiation force on a spherical object in an axisymmetric wave field and its application to the calibration of high-frequency transducers, *The Journal of the Acoustical Society of America* 99(2), 713-724.

Cho, H.-J. et al. (2006) The Effect of Stem Cell Mobilization by Granulocyte-Colony Stimulating Factor on Neointimal Hyperplasia and Endothelial Healing After Vascular Injury With Bare-Metal Versus Paclitaxel-Eluting Stents, *Journal of the American College of Cardiology* 48(2), 366-374.

Co, M. et al. (2008) Use of endothelial progenitor cell capture stent (Genous Bio-Engineered R Stent) during primary percutaneous coronary intervention in acute myocardial infarction: Intermediate- to long-term clinical follow-up, *American Heart Journal* 155(1), 128-132.

Conte, M. S. et al. (1994) Efficient repopulation of denuded rabbit arteries with autologous genetically modified endothelial cells, *Circulation* 89(5), 2161-2169.

Conti, E. et al. (2004) Insulin-Like Growth Factor-1 as a Vascular Protective Factor, *Circulation* 110(15), 2260-2265.

U.S. Appl. No. 10/520,405, filed Jul. 9, 2003, Katz, L.-h., Issue Date Oct. 6, 2005.

U.S. Appl. No. 09/765,614, filed Jan. 22, 2001, Klaveness, J. et al., Issue Date Aug. 1, 2002.

U.S. Appl. No. 10/108,284, filed Mar. 26, 2002, Unger, E. C. et al., Issue Date Feb. 27, 2003.

Crisan, M. et al. (2008) A Perivascular Origin for Mesenchymal Stem Cells in Multiple Human Organs, *Cell Stem Cell* 3(3), 301-313.

Dayton, P. et al. (1999) Acoustic radiation force in vivo: a mechanism to assist targeting of microbubbles, *Ultrasound in Medicine & Biology* 25(8), 1195-1201.

Dayton, P. A. et al. (2002) The magnitude of radiation force on ultrasound contrast agents, *The Journal of the Acoustical Society of America* 112(5), 2183-2192.

Dayton, P. A. et al. (2006) Application of Ultrasound to Selectively Localize Nanodroplets for Targeted Imaging and Therapy, *Molecular Imaging* 5(3), 160-174.

Dong, C. and Goldschmidt-Clermont, P. J. (2007) Endothelial Progenitor Cells: A Promising Therapeutic Alternative for Cardiovascular Disease, *Journal of Interventional Cardiology* 20(2), 93-99.

Dong, J.-d. et al. (2009) Response of mesenchymal stem cells to shear stress in tissue-engineered vascular grafts, *Acta Pharmacol Sin* 30(5), 530-536.

Doriot, P.-A. et al. (2000) In-vivo measurements of wall shear stress in human coronary arteries, *Coronary Artery Disease* 11(6), 495-502.

Duda, D. G. et al. (2007) A protocol for phenotypic detection and enumeration of circulating endothelial cells and circulating progenitor cells in human blood, *Nature Protocols* 2(4), 805-810.

Finn, A. V. et al. (2007) Vascular Responses to Drug Eluting Stents, *Arteriosclerosis, Thrombosis, and Vascular Biology* 27(7), 1500-1510.

Forte, A. et al. (2008) Mesenchymal stem cells effectively reduce surgically induced stenosis in rat carotids, *Journal of Cellular Physiology* 217(3), 789-799.

Gnecchi, M. et al. (2006) Evidence supporting paracrine hypothesis for Akt-modified mesenchymal stem cell-mediated cardiac protection and functional improvement, *The FASEB Journal* 20(6), 661-669.

Hamilos, M. I. et al. (2008) Differential Effects of Drug-Eluting Stents on Local Endothelium-Dependent Coronary Vasomotion, *Journal of the American College of Cardiology* 51(22), 2123-2129.

Hare, J. M. et al. (2009) A Randomized, Double-Blind, Placebo-Controlled, Dose-Escalation Study of Intravenous Adult Human Mesenchymal Stem Cells (Prochymal) After Acute Myocardial Infarction, *Journal of the American College of Cardiology* 54(24), 2277-2286.

Hashi, C. K. et al. (2007) Antithrombogenic property of bone marrow mesenchymal stem cells in nanofibrous vascular grafts, *Proceedings of the National Academy of Sciences* 104(29), 11915-11920.

Hawkes, J. J. et al. (2004) Continuous cell washing and mixing driven by an ultrasound standing wave within a microfluidic channel, *Lab on a Chip* 4(5), 446-452.

He, T. et al. (2004) Transplantation of Circulating Endothelial Progenitor Cells Restores Endothelial Function of Denuded Rabbit Carotid Arteries, *Stroke* 35(10), 2378-2384.

Hu, Y. et al. (2009) Chirp excitation technique to enhance microbubble displacement induced by ultrasound radiation force, *Journal of the Acoustical Society of America* 125(3), 1410-1415.

Joner, M. et al. (2008) Endothelial Cell Recovery Between Comparator Polymer-Based Drug-Eluting Stents, *Journal of the American College of Cardiology* 52(5), 333-342.

Kawabata, K. and Umemura, S. (1996) Effect of second-harmonic superimposition on efficient induction of sonochemical effect, *Ultrasonics Sonochemistry* 3(1), 1-5.

Kawamoto, A. and Asahara, T. (2007) Role of progenitor endothelial cells in cardiovascular disease and upcoming therapies, *Catheterization and Cardiovascular Interventions* 70(4), 477-484.

Keegan, M. E. et al. (2004) Biodegradable Microspheres with Enhanced Capacity for Covalently Bound Surface Ligands, *Macromolecules* 37(26), 9779-9784.

Kinnaird, T. et al. (2004) Bone Marrow-Derived Cells for Enhancing Collateral Development, *Circulation Research* 95(4), 354-363.

Kong, D. et al. (2004) Enhanced Inhibition of Neointimal Hyperplasia by Genetically Engineered Endothelial Progenitor Cells, *Circulation* 109(14), 1769-1775.

Kutryk, M. J. B. and Kuliszewski, M. A. (2003) In Vivo Endothelial Progenitor Cell Seeding for the Accelerated Endothelialization of Endovascular Devices, *The American Journal of Cardiology* 92(6, Supplement 1), 94-97.

Kyrtatos, P. G. et al. (2009) Magnetic Tagging Increases Delivery of Circulating Progenitors in Vascular Injury, *JACC: Cardiovascular Interventions* 2(8), 794-802.

Lagerqvist, B. et al. (2007) Long-Term Outcomes with Drug-Eluting Stents versus Bare-Metal Stents in Sweden, *New England Journal of Medicine* 356(10), 1009-1019.

Le Blanc, K. et al. (2008) Mesenchymal stem cells for treatment of steroid-resistant, severe, acute graft-versus-host disease: a phase II study, *The Lancet* 371(9624), 1579-1586.

Leon, M. B. et al. (1998) A Clinical Trial Comparing Three Antithrombotic-Drug Regimens after Coronary-Artery Stenting, *New England Journal of Medicine* 339(23), 1665-1671.

Llevadot, J. et al. (2001) HMG-CoA reductase inhibitor mobilizes bone marrow-derived endothelial progenitor cells, *Journal of Clinical Investigation* 108(3), 399-405.

Lu, X. et al. (2004) A new method to denude the endothelium without damage to media: structural, functional, and biomechanical validation, *American Journal of Physiology—Heart and Circulatory Physiology* 286(5), H1889-H1894.

Massachusetts Institute of Technology. (2004) Moving Cells With Sound, *Technology Review*.

Mintz, G. S. et al. (2001) American College of Cardiology clinical expert consensus document on standards for acquisition, measurement and reporting of intravascular ultrasound studies (ivus): A report of the american college of cardiology task force on clinical expert consensus documents developed in collaboration with the european society of cardiology endorsed by the society of cardiac angiography and interventions, *Journal of the American College of Cardiology 37*(5), 1478-1492.

Mirza, A. et al. (2008) Undifferentiated mesenchymal stem cells seeded on a vascular prosthesis contribute to the restoration of a physiologic vascular wall, *Journal of Vascular Surgery 47*(6), 1313-1321.

Nakazawa, G. et al. (2008) Delayed Arterial Healing and Increased Late Stent Thrombosis at Culprit Sites After Drug-Eluting Stent Placement for Acute Myocardial Infarction Patients, *Circulation 118*(11), 1138-1145.

Pendyala, L. K. et al. (2009) Endothelium-Dependent Vasomotor Dysfunction in Pig Coronary Arteries With Paclitaxel-Eluting Stents Is Associated With Inflammation and Oxidative Stress, *JACC: Cardiovascular Interventions 2*(3), 253-262.

Petersson, F. et al. (2007) Free Flow Acoustophoresis: Microfluidic-Based Mode of Particle and Cell Separation, *Analytical Chemistry 79*(14), 5117-5123.

Pfisterer, M. et al. (2006) Late Clinical Events After Clopidogrel Discontinuation May Limit the Benefit of Drug-Eluting Stents: An Observational Study of Drug-Eluting Versus Bare-Metal Stents, *Journal of the American College of Cardiology 48*(12), 2584-2591.

Pislaru, S. V. et al. (2006) Magnetically Targeted Endothelial Cell Localization in Stented Vessels, *Journal of the American College of Cardiology 48*(9), 1839-1845.

Pittenger, M. F. et al. (1999) Multilineage potential of adult human mesenchymal stem cells, 284 5411(143-7).

Popma, J. J. et al. (2007) FDA Advisory Panel on the Safety and Efficacy of Drug-Eluting Stents: Summary of Findings and Recommendations, *Journal of Interventional Cardiology 20*(6), 425-446.

Potapova, I. A. et al. (2007) Mesenchymal Stem Cells Support Migration, Extracellular Matrix Invasion, Proliferation, and Survival of Endothelial Cells In Vitro, *Stem Cells 25*(7), 1761-1768.

Quevedo, H. C. et al. (2009) Allogeneic mesenchymal stem cells restore cardiac function in chronic ischemic cardiomyopathy via trilineage differentiating capacity, *Proceedings of the National Academy of Sciences 106*(33), 14022-14027.

Rafii, S. and Lyden, D. (2003) Therapeutic stem and progenitor cell transplantation for organ vascularization and regeneration, *Nature Medicine 9*(6), 702-712.

Rauscher, F. M. et al. (2003) Aging, Progenitor Cell Exhaustion, and Atherosclerosis, *Circulation 108*(4), 457-463.

Schinköthe, T. et al. (2008) In vitro secreting profile of human mesenchymal stem cells, *Stem Cells and Development 17*(1), 199-206.

Schwartz, R. S. et al. (2008) Drug-Eluting Stents in Preclinical Studies, *Circulation: Cardiovascular Interventions 1*(2), 143-153.

Soenen, S. J. H. et al. (2009) Addressing the problem of cationic lipid-mediated toxicity: The magnetoliposome model, *Biomaterials 30*(22), 3691-3701.

Soltani, A. et al. (2007) Absence of biological damage from prolonged exposure to intravascular ultrasound: A swine model, *Ultrasonics 46*(1), 60-67.

Sorrell, J. M. et al. (2009) Influence of adult mesenchymal stem cells on in vitro vascular formation, *Tissue Engineering, Part A: Tissue Engineering 15*(7), 1751-1761.

Suzuki, Y. et al. (2009) The Pre-Clinical Animal Model in the Translational Research of Interventional Cardiology, *JACC: Cardiovascular Interventions 2*(5), 373-383.

Takano, M. et al. (2007) Serial long-term evaluation of neointimal stent coverage and thrombus after sirolimus-eluting stent implantation by use of coronary angioscopy, *Heart 93*(11), 1353-1356.

Tartis, M. S. et al. (2006) Therapeutic effects of paclitaxel-containing ultrasound contrast agents, *Ultrasound in Medicine & Biology 32*(11), 1771-1780.

Tögel, F. et al. (2007) Vasculotropic, paracrine actions of infused mesenchymal stem cells are important to the recovery from acute kidney injury, *American Journal of Physiology—Renal Physiology 292*(5), F1626-F1635.

Toma, C. et al. (2007) Positive effect of darbepoetin on peri-infarction remodeling in a porcine model of myocardial ischemia-reperfusion, *J. Mol. Cell. Cardiol. 43*(2), 130-136.

Toma, C. et al. (2002) Human Mesenchymal Stem Cells Differentiate to a Cardiomyocyte Phenotype in the Adult Murine Heart, *Circulation 105*(1), 93-98.

Toma, C. et al. (2009) Fate of Culture-Expanded Mesenchymal Stem Cells in the Microvasculature, *Circ. Res. 104*(3), 398-402.

Tomsick, T. et al. (2008) Revascularization Results in the Interventional Management of Stroke II Trial, *American Journal of Neuroradiology 29*(3), 582-587.

Uccelli, A. et al. (2008) Mesenchymal stem cells in health and disease, *Nature Reviews Immunology 8*(9), 726-736.

Unger, E. C. et al. (2004) Therapeutic applications of lipid-coated microbubbles, *Advanced Drug Delivery Reviews 56*(9), 1291-1314.

Villanueva, F. S. et al. (2007) Myocardial Ischemic Memory Imaging With Molecular Echocardiography, *Circulation 115*(3), 345-352.

Wang, C.-H. et al. (2008) Late-Outgrowth Endothelial Cells Attenuate Intimal Hyperplasia Contributed by Mesenchymal Stem Cells After Vascular Injury, *Arteriosclerosis, Thrombosis, and Vascular Biology 28*(1), 54-60.

Wang, S.-H. et al. (2009) Late Outgrowth Endothelial Cells Derived From Wharton Jelly in Human Umbilical Cord Reduce Neointimal Formation After Vascular Injury, *Arteriosclerosis, Thrombosis, and Vascular Biology 29*(6), 816-822.

Wheatley, M. A. et al. (1998) Ultrasound-Triggered Drug Delivery with Contrast Imaging: Effect of Microencapsulation Method, *Materials Research Society symposia proceedings 550*, 113.

Wissgott, C. et al. (2007) Treatment of Critical Limb Ischemia Using Ultrasound-enhanced Thrombolysis (PARES Trial): Final Results, *Journal of Endovascular Therapy 14*(4), 438-443.

Wu, X. et al. (2005) Effect of Paclitaxel and Mesenchymal Stem Cells Seeding on Ex Vivo Vascular Endothelial Repair and Smooth Muscle Cells Growth, *Journal of Cardiovascular Pharmacology 46*(6), 779-786.

Young, J. J. et al. (2008) Vulnerable plaque intervention: State of the art, *Catheterization and Cardiovascular Interventions 71*(3), 367-374.

Yue, W.-M. et al. (2008) Mesenchymal stem cells differentiate into an endothelial phenotype, reduce neointimal formation, and enhance endothelial function in a rat vein grafting model, *Stem Cells and Development 17*(4), 785+.

Zeng, L. et al. (2006) HDAC3 is crucial in shear- and VEGF-induced stem cell differentiation toward endothelial cells, *The Journal of Cell Biology 174*(7), 1059-1069.

Zhao, S. et al. (2004) Radiation-Force Assisted Targeting Facilitates Ultrasonic Molecular Imaging, *Molecular Imaging 3*(3), 135-148.

Zheng, H. et al. (2007) Ultrasound-Driven Microbubble Oscillation and Translation Within Small Phantom Vessels, *Ultrasound in Medicine & Biology 33*(12), 1978-1987.

\* cited by examiner

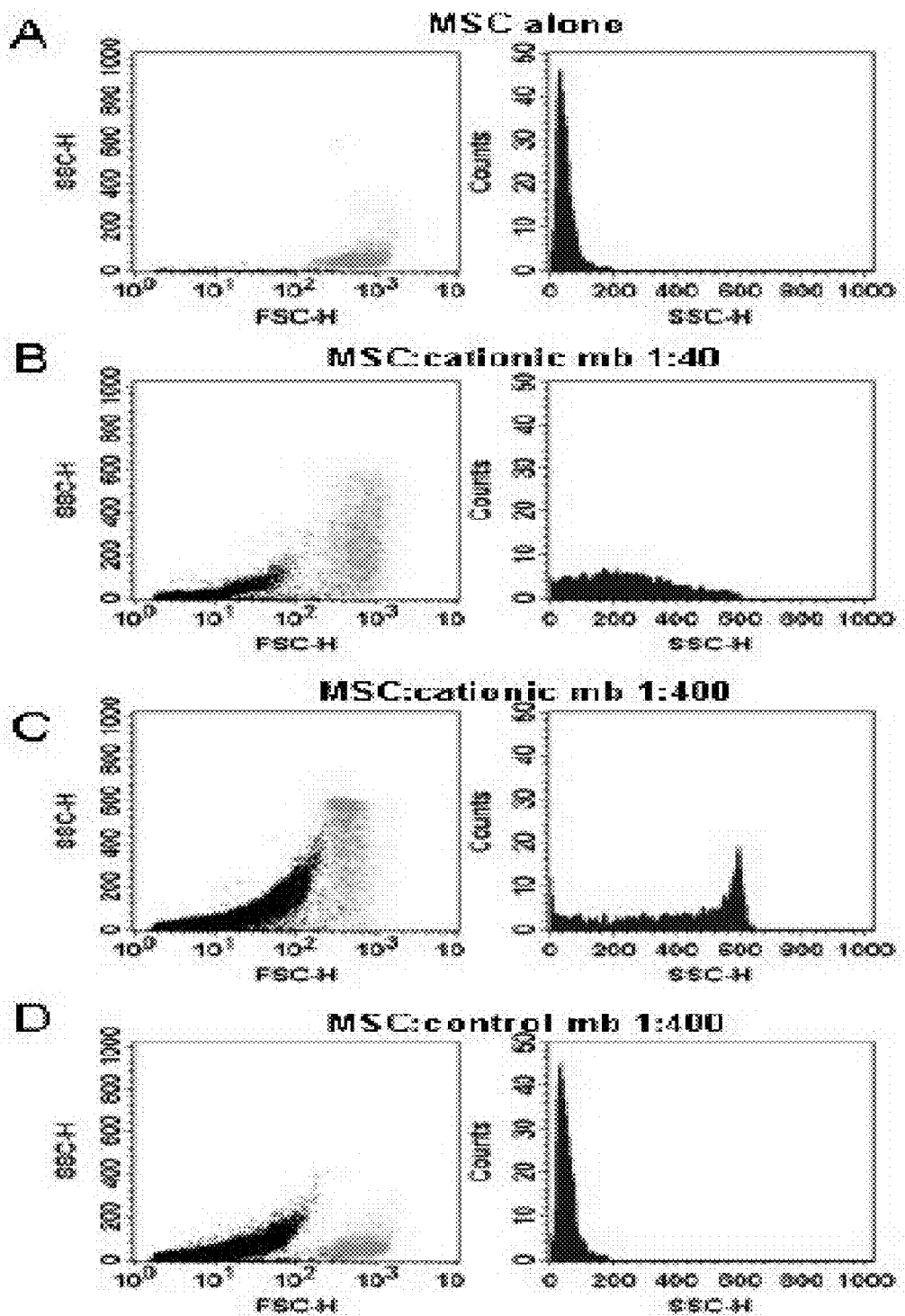
FIGURE 9 (Sheet 1 of 2)

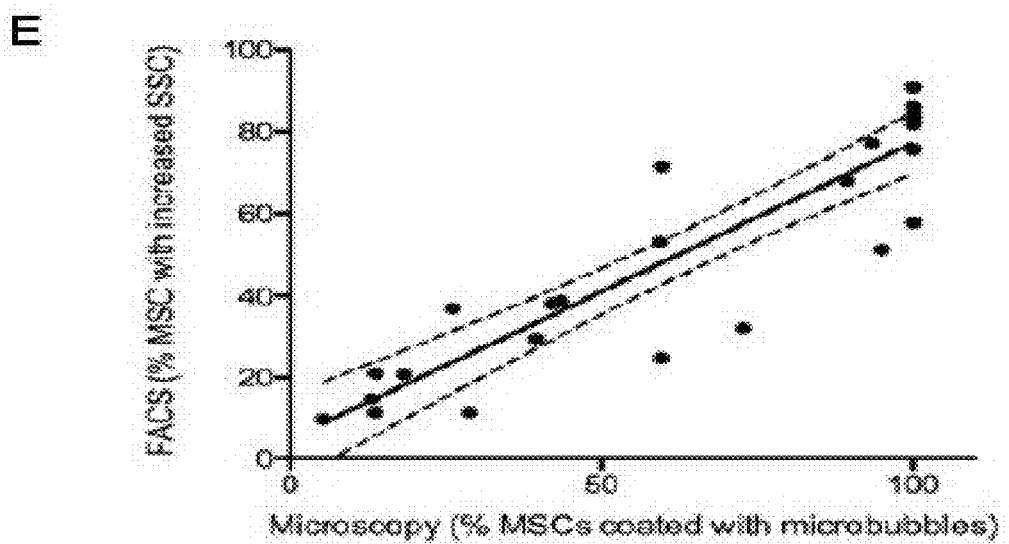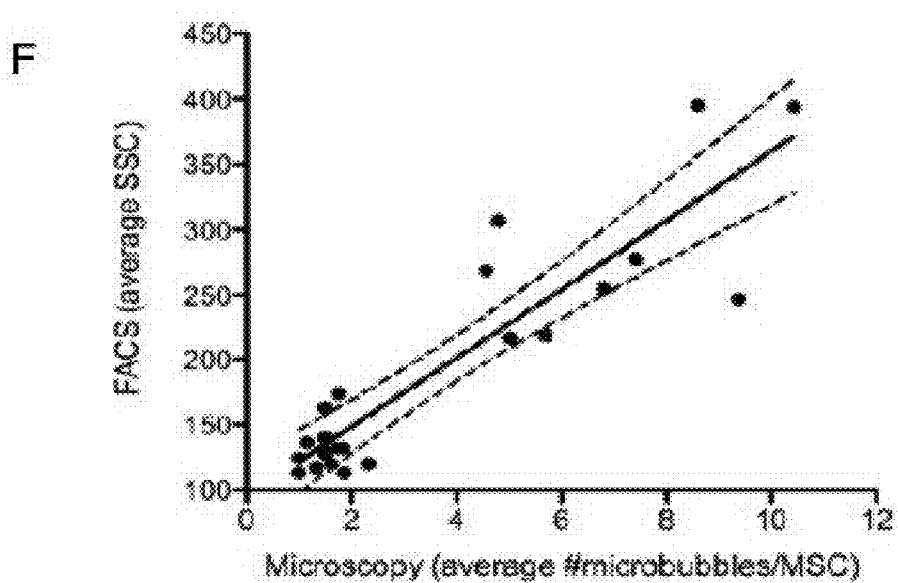
FIGURE 9 (Sheet 2 of 2)

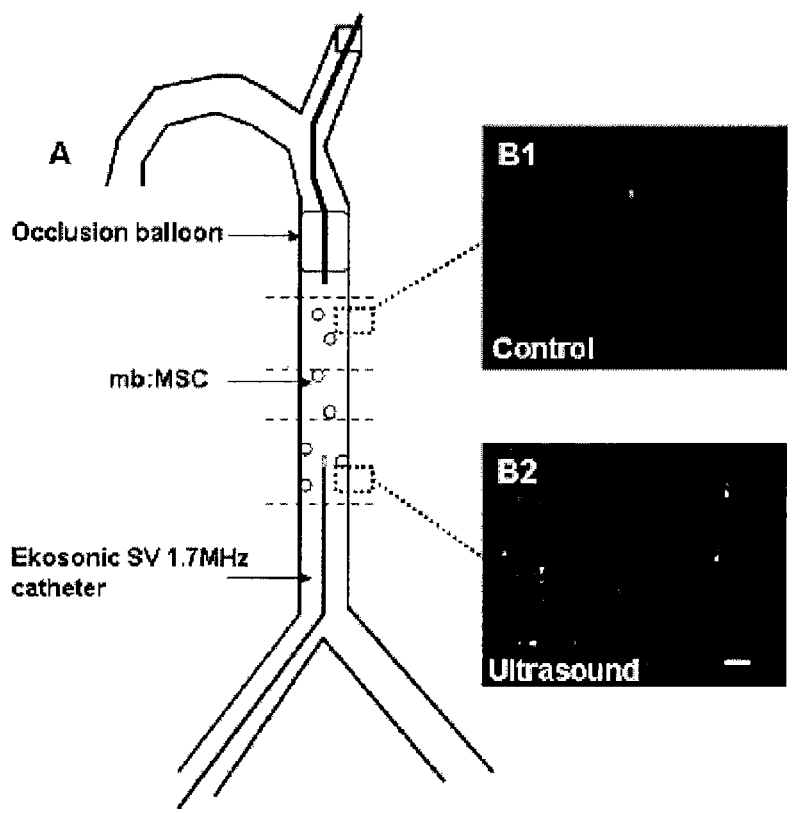
FIGURE 15
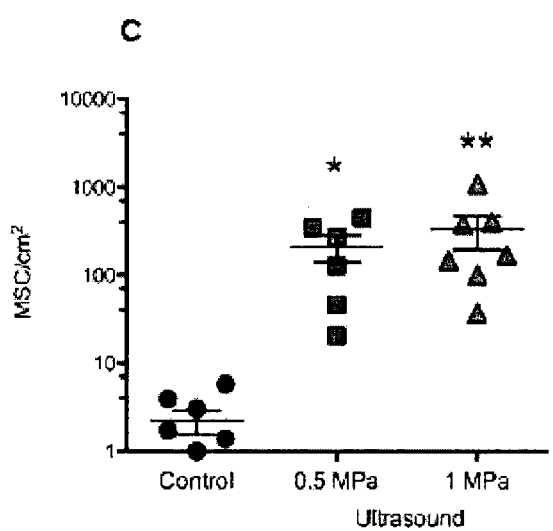

DIRECTED CELL-BASED THERAPY USING MICROBUBBLE TAGGED CELLS

FIELD OF THE INVENTION

The present invention is related to the field of cell based therapy. For example, tissue regeneration and healing may be mediated by an increased presence of biologically active progenitor cells. For example, accelerated endothelial tissue growth may be accomplished following certain cardiovascular surgical procedures and/or vascular injury, insertion of a stent, or after a balloon angioplasty procedure by increasing the presence of endothelial progenitor cells, as well as for prosthetic vascular grafts (for example a dialysis arteriovenous fistula). Such endothelial cell growth may be accelerated by selectively targeting progenitor cells to the area in need for repair using acoustic radiation force. For example, such endothelial growth may reduce thrombotic complications associated with these devices and to increase patency.

BACKGROUND OF THE INVENTION

Endothelial damage occurs early in the development of a coronary atherosclerotic plaque. Moreover, following angioplasty and stenting, there is significant injury to the arterial wall, with loss of endothelial coverage. Gradual re-endothelialization of the stented segment occurs, but this process is significantly delayed with drug eluting stents, and is a major mechanistic contributor to stent thrombosis. Joner et al., "Endothelial cell recovery between comparator polymer-based drug-eluting stents" *J Am Coll Cardiol.* 52:333-3342 (2008); and Finn et al., "Vascular responses to drug eluting stents: importance of delayed healing" *Arterioscler Thromb Vasc Biol.* 27:1500-1510 (2007), respectively.

Very few drugs and other biologicals such as hormones and/or biopeptides have successfully improved tissue regeneration and/or healing. For the most part, most drugs involve indirect mechanisms such as reducing inflammation. Furthermore, compounds having a significant direct effect stimulating cell proliferation are not yet approved for clinical use.

Since the first coronary percutaneous intervention (PCI) performed by Dr. Andreas Grunzing in 1977, the field of interventional cardiology has progressed exponentially, with a major impact in the treatment and outcome of coronary artery disease (CAD). The technology for treating atherosclerotic plaque has progressed from simple balloon angioplasty to intracoronary placement of bare metal stents (BMS) and more recently, to the usage of drug eluting stents (DES), which have been effective at preventing in-stent restenosis associated with BMS. However, one of the problems emerging with the widespread clinical application of stents, in particular with DES, is the occurrence of stent thrombosis, sometimes occurring very late following the index procedure, with devastating clinical consequences. Lagerqvist et al., "SCAAR Study Group. Long-term outcomes with drug-eluting stents versus bare-metal stents in Sweden" *N Engl J Med.* 356(10):1009-1019 (2007). It has been reported that up to 7% of acute myocardial infarctions (MI) are caused by stent thrombosis. Browning et al., "The changing face of ST Elevation myocardial infarction; trends in the drug eluting stent era" *Catheter Cardiovasc Intervention* 73:11 (2009). Stent thrombosis occurs at a rate of 0.25-0.5% yearly with DES, and it is unclear whether a plateau has been reached yet. Pfiesterer et al., "Late clinical events after clopidogrel discontinuation may limit the benefit of drug-eluting stents: an observational study of drug-eluting versus bare-metal stents" *J Am Coll Cardiol* 48:2584-2591 (2006). Hence, with nearly a million coronary stents implanted yearly in the United States alone, the incidence of MI due to stent thrombosis is a potentially expanding problem.

The failure of the normal protective functions of the vascular endothelium is the hallmark of atherosclerotic cardiovascular disease, leading to the formation of atherosclerotic plaques as well as insufficient repair of sites of arterial injury. A similar problem occurs with the use of arterial stents, with late thrombosis due to delayed healing of the vessel wall and incomplete endothelial coverage of the stents struts as well as other artificial vascular prostheses. Takano et al., "Serial long-term evaluation of neointimal stent coverage and thrombus after sirolimus-eluting stent implantation by use of coronary angioscopy" *Heart* 93(11):1353-1356 (2007), What is needed in the art are compositions and methods that can be delivered locally and are capable of accelerating biological pathways (i.e., for example, cell proliferation) where systemically delivered drugs and/or biological compounds are not available and/or marginally clinically effective.

SUMMARY

The present invention is related to the field of cell based therapy. For example, tissue regeneration and healing may be mediated by an increased presence of biologically active progenitor cells. For example, accelerated endothelial tissue growth may be accomplished following certain cardiovascular surgical procedures and/or vascular injury, insertion of a stent, or after a balloon angioplasty procedure by increasing the presence of endothelial progenitor cells. Such endothelial cell growth may be accelerated by administering a microbubble composition comprising personalized endothelial progenitor cells. For example, such endothelial growth may reduce thrombotic complications associated with these devices and to increase patency.

In one embodiment, the present invention contemplates a composition comprising a microbubble attached to a cell, wherein said microbubble encapsulates an acoustically active gas. In one embodiment, the gas is selected from the group comprising air, noble gases, such as helium, rubidium, hyperpolarized xenon, hyperpolarized argon, hyperpolarized helium, neon, argon, xenon, carbon dioxide, nitrogen, fluorine, oxygen, sulfur-based gases, such as sulfur hexafluoride and sulfur tetrafluoride, or fluorinated gases. In one embodiment, the cell comprises a progenitor cell. In one embodiment, the cell comprises a stem cell. In one embodiment, the cell is attached to the microbubble using non-covalent associations. In one embodiment, the cell is attached to the microbubble using covalent associations. In one embodiment, the cell is attached to the microbubble using hydrophobic interactions. In one embodiment, the cell is attached to the microbubble outside surface. In one embodiment, the microbubble displays a progenitor cell-specific ligand. In one embodiment, the biological progenitor cell comprises a stem cell. In one embodiment, the biological progenitor cell comprises an endothelial progenitor cell. In one embodiment, the biological progenitor cell comprises mesenchymal stem cell. In one embodiment, the composition further comprises a pharmaceutically acceptable vehicle.

In one embodiment, the present invention contemplates a method comprising: a) providing: i) a microbubble:biological progenitor cell complex, wherein the microbubble binds the cell via a progenitor cell-specific ligand; and ii) an acoustic radiation source, and b) directing the location of said microbubble:cell complex using acoustic radiation from said acoustic radiation source. In one embodiment, the microbubble further comprises an acoustically active gas. In one embodiment, the biological progenitor cell comprises a stem cell. In one embodiment, the biological progenitor cell comprises an endothelial progenitor cell. In one embodiment, the composition further comprises a pharmaceutically acceptable vehicle.

In one embodiment, the present invention contemplates a method comprising: a) providing: i) a microbubble:biological progenitor cell complex, wherein the microbubble binds the cell via a biological progenitor cell-specific ligand; ii) a patient comprising injured tissue, and iii) an acoustic radiation force, and b) administering said microbubble:cell complex to said patient, and c) applying said acoustic radiation force within said patient under conditions such that said complex contact said injured tissue. In one embodiment, the method further comprises step (d) accelerating injured tissue growth by the contact of the complex to the injured tissue. In one embodiment, the microbubble further comprises an acoustically active gas. In one embodiment, the microbubble is attached to the progenitor cell by the cell-specific ligand. In one embodiment, the progenitor cell is derived from the patient.

In one embodiment, the present invention contemplates a method comprising: a) providing: i) a microbubble:endothelial progenitor cell complex, wherein the microbubble binds the cell via an endothelial progenitor cell-specific ligand, ii) a patient comprising injured endothelial tissue, and iii) an acoustic radiation force, and b) administering said complex to said patient, and c) applying said acoustic radiation force within said patient under conditions such that said complex contacts said injured tissue. In one embodiment, the method further comprises step (d) accelerating injured tissue growth by the contact of the complex to the injured tissue. In one embodiment, the microbubble is attached to the endothelial progenitor cell by the cell-specific ligand. In one embodiment, the injured endothelial tissue is selected from the group consisting of a blood vessel tissue, an artery tissue, and a vein tissue. In one embodiment, the endothelial progenitor cell is derived from the patient.

In one embodiment, the present invention contemplates a method, comprising: a) providing: i) a patient, wherein said patient comprises an endothelial tissue with an implanted stent, ii) a microbubble:endothelial progenitor cell complex, wherein the microbubble binds the cell via an endothelial progenitor cell-specific ligand, and iii) an acoustic radiation force, c) administering the complex to said patient; and d) applying said acoustic radiation force to the complex under conditions such that the complex contacts the stent. In one embodiment, the endothelial tissue comprises an artery. In one embodiment, the endothelial tissue comprises a vein. In one embodiment, the endothelial tissue comprises a damaged vascular surface. In one embodiment, the method further comprises step (e) accelerating the endothelial tissue growth by the contact of the complex with the endothelial tissue. In one embodiment, the microbubble further comprises an acoustically active gas. In one embodiment, the ligand is selected from the group comprising a vascular endothelial growth factor (VEGF) molecule, a monoclonal CD34 antibody, or a monoclonal CD133 antibody. In one embodiment, the acoustic radiation force is generated by an intravascular ultrasound probe. In one embodiment, the administering further comprises a medical device compatible with said patient. In one embodiment, the medical device is selected from the group consisting of an injection needle or a catheter. In one embodiment, the endothelial progenitor cell is derived from the patient.

In one embodiment, the present invention contemplates a method of promoting endothelialization, comprising: a) providing: i) a patient with a stent, ii) a microbubble, iii) a cell, and iv) an acoustic radiation source, b) forming a cell-microbubble complex, c) introducing said cell-microbubble complex into the circulation of said patient proximal to said stent, and d) directing said cell-microbubble complex towards said stent using acoustic radiation from said acoustic radiation source. In one embodiment, the cell is an endothelial progenitor cell. In one embodiment, the cell is a bone marrow derived mesenchymal stem cell (MSC). In one embodiment, the microbubble is an acoustically active microbubble. In one embodiment, the acoustically active microbubble is filled with a gas. In one embodiment, the microbubble includes a ligand. In one embodiment, the ligand is an endothelial progenitor cell-specific ligand. In one embodiment, the ligand is selected from the group comprising a vascular endothelial growth factor (VEGF) molecule, a monoclonal CD34 antibody, or a monoclonal CD133 antibody. In one embodiment, the acoustic radiation source is an intravascular ultrasound probe. In one embodiment, the introducing comprises a route selected from the group consisting of oral, parenteral, intravenous, intradermal, intraperitoneal, intramuscular, intranasal. In one embodiment, the introducing further comprises a medical device compatible with said patient. In one embodiment, the medical device is selected from the group consisting of an injection needle or a catheter. In one embodiment, the endothelial progenitor cell is derived from the patient.

In one embodiment, the present invention contemplates a method comprising: providing a small vessel catheter, wherein the catheter is capable of delivering autologous cells to a stented coronary segment and an intravascular ultrasound catheter. In one embodiment, the autologous cells are attached to a plurality of microbubbles, thereby forming a cell:microbubble complex. In one embodiment, the cell:microbubble complex is formed in an approximate 1:40 ratio. In one embodiment, the cell:microbubble complex comprises an MSC:microbubble complex. In one embodiment, the MSC:microbubble complex is created ex vivo. In one embodiment, the MSC:microbubble complex is administered by an intra-coronary injection. In one embodiment, the intra-coronary injection is administered via the small vessel catheter. In one embodiment, the method further comprises driving the MSC:microbubble complex radially outward from the intravascular ultrasound catheter. In one embodiment, the MSC:microbubble complex adheres to an endothelial wall, thereby accelerating endothelialization of an injured vascular segments. In one embodiment, the vascular segment includes, but is not limited to, a coronary or peripheral vascular segment. In one embodiment, the injured vascular segment may be caused by a vascular stent, a vascular graft, or a vascular prostheses.

In one embodiment, the present invention contemplates a method comprising: a) providing; i) a patient comprising injured vascular tissue; ii) a plurality of cell:microbubble complexes; and iii) an endovascular ultrasound catheter; b) paving the injured vascular tissue with the plurality of cell:microbubble complexes, thereby initiating a self-generating vascular tissue healing process. In one embodiment, the self-generating vascular tissue healing process comprising re-endothelialization. In one embodiment, the self-generating vascular tissue healing process results in formation of a functional endothelium. In one embodiment, the cell:microbubble complexes are in a 1:40 ratio. In one embodiment, the method further comprises, before step b), administering a dose of the plurality of cell:microbubble complexes to the patient. In one embodiment, the paving comprises adherence of at least 30% of the administered cell:microbubble dose to the injured vascular tissue. In one embodiment, the method further comprises, before step b), inserting the catheter into the injured vascular tissue. In one embodiment, the catheter emits radial acoustic energy thereby driving the cell:microbubble complexes towards the vascular tissue.

In one embodiment, the present invention contemplates a kit comprising a pharmaceutically acceptable composition comprising a microbubble displaying a biological progenitor cell-specific ligand. In one embodiment, the microbubble encapsulates an acoustically active gas. In one embodiment, the cell-specific ligand comprises an endothelial progenitor cell-specific ligand. In one embodiment, the cell-specific ligand comprises a stem cell specific ligand. In one embodiment, the endothelial progenitor cell-specific ligand is selected from the group comprising a vasculature endothelial growth factor (VEGF) molecule, a monoclonal CD34 antibody, or a monoclonal CD133 antibody. In one embodiment, the kit further comprises a medical device. In one embodiment, the medical device is selected from the group comprising an injection needle or a catheter. In one embodiment, the kit further comprises reagents to attach the microbubble to an endothelial progenitor cell. In one embodiment, the endothelial progenitor cell is derived from a patient. In one embodiment, the kit further comprises a sheet of instructions describing how to attach the endothelial cell to the microbubble. In one embodiment, the sheet of instructions further describe the use of the composition with the medical device to administer the composition to the patient.

DEFINITIONS

"Cellular paving" or "paving" as used herein, refers to any cell-based method that is capable of adhering a cellular layer on a preselected injured and/or diseased tissue. Cellular paving results in the creation of a self-generating tissue healing process that results in a functional tissue. Such cellular layers include, but are not limited to, 300-10,000 cells/mm$^2$, 500-5,000 cells/mm$^2$, 750-2,000 cells/mm$^2$, or 1000 cell/mm$^2$. Preferable cells for cellular paving include, but are not limited to, progenitor cells.

A "microbubble", as used herein, refer to any spherical molecular complex comprising lipids, proteins, or polymers (or any combination thereof) capable of incorporating an acoustically active gas and displaying a biological cell-specific ligand. Suitable proteins may include, but are not limited to, albumin or polylysine. Suitable lipids may include, but are not limited to, natural, synthetic or semi-synthetic origin, including for example, fatty acids, neutral fats, phosphatides, oils, glycolipids, surface-active agents (surfactants), aliphatic alcohols, waxes, terpenes and steroids. Suitable polymers may include, but are not limited to, a single repeating unit or different repeating units which form a random, alternating or block-type co-polymer. These organic polymers may include, but are not limited to, cross-linked polyelectrolytes such as phosphazenes, imino-substituted polyphosphazenes, polyacrylic acids, polymethacrylic acids, polyvinyl acetates, polyvinyl amines, polyvinyl pyridine, polyvinyl imidazole, and ionic salts thereof. Cross-linking of these polyelectrolytes may be accomplished by reaction with multivalent ions of the opposite charge.

An "acoustically active gas" as used herein, refers to any gas (i.e., for example perfluorobutane) that may be entrapped within a microbubble that vibrates in the presence of an acoustically generated radiation force, thereby inducing movement in the direction of the force. Suitable gases are inert and biocompatible, and include, for example, air, noble gases, such as helium, rubidium, hyperpolarized xenon, hyperpolarized argon, hyperpolarized helium, neon, argon, xenon, carbon dioxide, nitrogen, fluorine, oxygen, sulfur-based gases, such as sulfur hexafluoride and sulfur tetrafluoride, fluorinated gases.

A "stent" as used herein, refers to any device implanted into a vessel lumen intended to maintain fluid flow. For example, a stent may be a mold formed from a resinous compound or a short narrow metal or plastic tube often in the form of a mesh.

The term "vascular graft" as used herein, refers to any conduit or portion thereof intended as a prosthetic device for conveying blood and, therefore, having a blood contacting surface (i.e., "luminal"). While usually in a tubular form, the graft may also be a sheet of material useful for patching portions of the circumference of living blood vessels (these materials are generally referred to as surgical wraps). Likewise, the term vascular graft includes intraluminal grafts for use within living blood vessels. The inventive grafts as such may also be used as a stent covering on the exterior, luminal or both surfaces of an implantable vascular stent.

A "cell" or "biological cell" as used herein refers to any one of the minute protoplasmic masses which make up organized tissue, comprising a mass of protoplasm surrounded by a membrane, including nucleated and unnucleated cells and organelles. For example, a cell may include but is not limited to, progenitor cells, stem cells, bone marrow cells, cancer cells, fibroblast cells, neuronal cells, osteoblast cells, white blood cells, platelet cells, lymph node cells, kidney cells, gastrointestinal cells etc.

An "endothelial progenitor cell" or "EPC" refers to any biological cell that, when in contact with endothelial tissue, directly develops into a mature endothelial cell. For example, an EPC may be derived from a patient in need of endothelial tissue regeneration and/or healing. The EPC expressed specific surface markers, such as, but not limited to CD34 and CD133, and are able to incorporate acetylated LDL and form microtubules in a matrigel assay. The ECPs can be isolated from peripheral blood or bone marrow by flow cytometry or by cell culture on fibronectin coated surfaces. The EPCs can also be isolated by mixing a patients blood with a microbubble displaying an EPC-specific ligand and may be separated by gravity separation techniques.

The term "medical device", as used herein, refers broadly to any apparatus used in relation to a medical procedure. Specifically, any apparatus that contacts a patient during a medical procedure or therapy is contemplated herein as a medical device. Similarly, any apparatus that administers a drug or compound to a patient during a medical procedure or therapy is contemplated herein as a medical device. "Direct medical implants" include, but are not limited to, urinary and intravascular catheters, dialysis catheters, wound drain tubes, skin sutures, vascular grafts and implantable meshes, intraocular devices, implantable drug delivery systems and heart valves, and the like. "Wound care devices" include, but are not limited to, general wound dressings, non-adherent dressings, burn dressings, biological graft materials, tape closures and dressings, surgical drapes, sponges and absorbable hemostats.

The term "surgical devices" include, but are not limited to, surgical instruments, catheter systems (i.e., catheters, vascular catheters, surgical tools such as scalpels, retractors, and the like) and temporary drug delivery devices such as drug ports, injection needles etc. to administer the medium.

The term "administered" or "administering" a drug or compound, as used herein, refers to any method of providing a drug or compound to a patient such that the drug or compound has its intended effect on the patient. For example, one method of administering is by an indirect mechanism using a medical device such as, but not limited to a catheter, applicator gun, syringe etc. A second exemplary method of administering is by a direct mechanism such as, local tissue administration (i.e., for example, extravascular placement), oral ingestion, transdermal patch, topical, inhalation, suppository etc.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The term "biodegradable" as used herein, refers to any material that can be acted upon biochemically by living cells or organisms, or processes thereof, including water, and broken down into lower molecular weight products such that the molecular structure has been altered.

The term "bioerodible" as used herein, refers to any material that is mechanically worn away from a surface to which it is attached without generating any long term inflammatory effects such that the molecular structure has not been altered. In one sense, bioerosion represents the final stages of "biodegradation" wherein stable low molecular weight products undergo a final dissolution.

The term "bioresorbable" as used herein, refers to any material that is assimilated into or across bodily tissues. The bioresorption process may utilize both biodegradation and/or bioerosion.

The term "wound" as used herein, denotes a bodily injury with disruption of the normal integrity of tissue structures. In one sense, the term is intended to encompass a "surgical site". In another sense, the term is intended to encompass wounds including, but not limited to, contused wounds, incised wounds, lacerated wounds, non-penetrating wounds (i.e., wounds in which there is no disruption of the skin but there is injury to underlying structures), open wounds, penetrating wound, perforating wounds, puncture wounds, septic wounds, subcutaneous wounds, burn injuries etc. Conditions related to wounds or sores which may be successfully treated according to the invention are skin diseases.

The term "surgical site" as used herein, refers to a site created by any opening in the skin or internal organs performed for a specific medical purpose. The surgical site may be "open" where medical personnel have direct physical access to the area of interest as in traditional surgery. Alternatively, the surgical site may be "closed" where medical personnel perform procedures using remote devices such as, but not limited to, catheters wherein fluoroscopes may be used to visualize the activities and; endoscopes (i.e., laparoscopes) wherein fiber optic systems may be used to visualize the activities. A surgical site may include, but is not limited to, organs, muscles, tendons, ligaments, connective tissue and the like.

"Surfactant" or "surface active agent" refer to a substance that alters energy relationship at interfaces, such as, for example, synthetic organic compounds displaying surface activity, including, inter alia, wetting agents, detergents, penetrants, spreaders, dispersing agents, and foaming agents. Preferable examples of surfactants useful in the present invention are hydrophobic compounds, and include phospholipids, oils, and fluorosurfactants.

"Emulsion" refers to a mixture of two or more generally immiscible liquids, and is generally in the form of a colloid. The mixture may be of lipids, for example, which may be homogeneously or heterogeneously dispersed throughout the emulsion. Alternatively, the lipids may be aggregated in the form of, for example, clusters or layers, including monolayers or bilayers.

"Dry" and variations thereof; refer to a physical state that is dehydrated or anhydrous, i.e., substantially lacking liquid. Drying includes for example, spray drying, lyophilization, and vacuum drying.

"Spray drying" refers to drying by bringing an emulsion of surfactant and a therapeutic, or portions thereof, in the form of a spray into contact with a gas, such as air, and recovering in the form of a dried emulsion. A blowing agent, such as methylene chloride, for example, may be stabilized by the surfactant.

"Lyophilize" or freeze drying refers to the preparation of a lipid composition in dry form by rapid freezing and dehydration in the frozen state (sometimes referred to as sublimation). Lyophilization takes place at a temperature which results in the crystallization of the lipids to form a lipid matrix. This process may take place under vacuum at a pressure sufficient to maintain frozen product with the ambient temperature of the containing vessel at about room temperature, preferably less than about 500 mTorr, more preferably less than about 200 mTorr, even more preferably less than about 1 mTorr. Due to the small amount of lipids used to prepare the lipid composition of the present invention, lyophilization is not difficult to conduct. The lipid composition in the present invention is an improvement over conventional microsphere compositions because the amount of lipids are reduced in comparison to the prior art and the lipid composition is formulated to minimize loss due to filtration of large (>0.22 µm) particulate matter. The latter is particularly important with lipids having a net negative charge (i.e. phosphatidic acid) because their solubility in aqueous-based diluents is marginal.

"Vacuum drying" refers to drying under reduced air pressure resulting in drying at a lower temperature than required at full pressure.

"Ball milling" refers to pulverizing in a hollow, usually cylindrical, drum that contains pebbles of material, such as steel balls, and optionally a liquid, that is revolved or agitated so the pebbles create a crushing action as they roll about the drum.

"Resuspending" refers to adding a liquid to change a dried physical state of a substance to a liquid physical state. For example, a dried therapeutic delivery system may be resuspended in a liquid such that it has similar characteristics in the dried and resuspended states. The liquid may be an aqueous liquid or an organic liquid, for example. In addition, the resuspending medium may be a cryopreservative. Polyethylene glycol, sucrose, glucose, fructose, mannose, trebalose, glycerol, propylene glycol, and sodium chloride may be useful as resuspending medium.

"Carrier" refers to a pharmaceutically acceptable vehicle, which is a nonpolar, hydrophobic solvent, and which may serve as a reconstituting medium. The carrier may be aqueous-based or organic-based. Carriers include, inter alia, lipids, proteins, polysaccharides, sugars, polymers, copolymers, and acrylates.

"Lipid" refers to a naturally-occurring, synthetic or semi-synthetic (i.e., modified natural) compound which is generally amphipathic. The lipids typically comprise a hydrophilic component and a hydrophobic component. Exemplary lipids include, for example, fatty acids, neutral fats, phosphatides, oils, glycolipids, surface-active agents (surfactants), aliphatic alcohols, waxes, terpenes and steroids. The phrase semi-synthetic (or modified natural) denotes a natural compound that has been chemically modified in some fashion.

"Polymer" or "polymeric" refers to molecules formed from the chemical union of two or more repeating units. Accordingly, included within the term "polymer" may be, for example, dimers, trimers and oligomers. The polymer may be synthetic, naturally-occurring or semisynthetic. In a preferred form, "polymer" refers to molecules which comprise 10 or more repeating units.

"Protein" refers to molecules comprising, and preferably consisting essentially of, .alpha.-amino acids in peptide linkages. Included within the term "protein" are globular proteins such as albumins, globulins and histones, and fibrous proteins such as collagens, elastins and keratins. Also included within the term "protein" are "compound proteins," wherein a protein molecule is united with a nonprotein molecule, such as nucleoproteins, mucoproteins, lipoproteins and metalloproteins. The proteins may be naturally-occurring, synthetic or semi-synthetic.

"Stabilizing material" or "stabilizing compound" refers to any material which is capable of improving the stability of compositions containing the gases, gaseous precursors, steroid prodrugs, cell-specific ligands and/or other bioactive agents described herein, including, for example, mixtures, suspensions, emulsions, dispersions, vesicles, or the like. Encompassed in the definition of "stabilizing material" are certain of the present bioactive agents. The improved stability involves, for example, the maintenance of a relatively balanced condition, and may be exemplified, for example, by increased resistance of the composition against destruction, decomposition, degradation, and the like. In the case of preferred embodiments involving vesicles filled with gases, gaseous precursors, liquids, steroid prodrugs and/or bioactive agents, the stabilizing compounds may serve to either form the vesicles or stabilize the vesicles, in either way serving to minimize or substantially (including completely) prevent the escape of gases, gaseous precursors, steroid prodrugs and/or bioactive agents from the vesicles until said release is desired. The term "substantially," as used in the present context of preventing escape of gases, gaseous precursors, steroid prodrugs and/or bioactive agents from the vesicles, means greater than about 50% is maintained entrapped in the vesicles until release is desired, and preferably greater than about 60%, more preferably greater than about 70%, even more preferably greater than about 80%, still even more preferably greater than about 90%, is maintained entrapped in the vesicles until release is desired. In particularly preferred embodiments, greater than about 95% of the gases, gaseous precursors, steroid prodrugs and/or bioactive agents are maintained entrapped until release is desired. The gases, gaseous precursors, liquids, steroid prodrugs and/or bioactive agents may also be completely maintained entrapped (i.e., about 100% is maintained entrapped), until release is desired. Exemplary stabilizing materials include, for example, lipids, proteins, polymers, carbohydrates and surfactants. The resulting mixture, suspension, emulsion or the like may comprise walls (i.e., films, membranes and the like) around the steroid prodrug, bioactive agent, gases and/or gaseous precursors, or may be substantially devoid of walls or membranes, if desired. The stabilizing may, if desired, form droplets. The stabilizing material may also comprise salts and/or sugars. In certain embodiments, the stabilizing materials may be substantially (including completely) cross-linked. The stabilizing material may be neutral, positively or negatively charged.

"Droplet" refers to a spherical or spheroidal entity which may be substantially liquid or which may comprise liquid and solid, solid and gas, liquid and gas, or liquid, solid and gas. Solid materials within a droplet may be, for example, particles, polymers, lipids, proteins, or surfactants.

The term "a microbubble encapsulating a gas" refers to a microbubble comprising a gas or a gaseous precursor. The microbubble may be minimally, partially, substantially, or completely filled with the gas and/or gaseous precursor. The term "substantially" as used in reference to the gas filled bubble means that greater than about 30% of the internal void of the substantially filled bubble comprises a gas. In certain embodiments, greater than about 40% of the internal void of the substantially filled bubble comprises a gas, with greater than about 50% being more preferred. More preferably, greater than about 60% of the internal void of the substantially filled bubble comprises a gas, with greater than about 70% or 75% being more preferred. Even more preferably, greater than about 80% of the internal void of the substantially filled bubble comprises a gas, with greater than about 85% or 90% being still more preferred. In particularly preferred embodiments, greater than about 95% of the internal void of the bubble comprises a gas, with about 100% being especially preferred. Alternatively, the bubble may contain no or substantially no gas.

"Suspension" or "dispersion" refers to a mixture, preferably finely divided, of two or more phases (solid, liquid or gas), such as, for example, liquid in liquid, solid in solid, gas in liquid, and the like which preferably can remain stable for extended periods of time.

"Patient" refers to animals, including mammals, preferably humans.

"Region of a patient" refers to a particular area or portion of the patient and in some instances to regions throughout the entire patient. Exemplary of such regions are the eye, gastrointestinal region, the cardiovascular region (including myocardial tissue), the renal region as well as other bodily regions, tissues, lymphocytes, receptors, organs and the like, including the vasculature and circulatory system, and as well as diseased tissue, including cancerous tissue, such as the prostate and breast. "Region of a patient" includes, for example, injured regions. The "region of a patient" is preferably internal, although, if desired, it may be external. The phrase "vasculature" denotes blood vessels (including arteries, veins and the like) that are part of the circulatory system. The phrase "gastrointestinal region" includes the region defined by the esophagus, stomach, small and large intestines, and rectum. The phrase "renal region" denotes the region defined by the kidney and the vasculature that leads directly to and from the kidney, and includes the abdominal aorta.

"Therapeutic" refers to any biologic or pharmacologic agent which may be used in the treatment (including the prevention, diagnosis, alleviation, or cure) of a malady, affliction, disease or injury in a patient. Therapeutically useful cells (i.e., for example, progenitor cells) may also comprise peptides, polypeptides and polynucleotides that may be included within the meaning of the term pharmaceutical or drug.

"Bioactive agent" refers to a substance which may be used in connection with an application that is therapeutic or diagnostic, such as, for example, in methods for diagnosing the presence or absence of a disease in a patient and/or methods for the treatment of a disease in a patient. "Bioactive agent" also refers to substances which are capable of exerting a biological effect in vitro and/or in vivo. The bioactive agents may be neutral, positively or negatively charged. Exemplary bioactive agents include, for example, biological cells, biological progenitor cells, prodrugs, cell-specific ligands, diagnostic agents, pharmaceutical agents, drugs, synthetic organic molecules, proteins, peptides, vitamins, steroids, steroid analogs and genetic material, including nucleosides, nucleotides and polynucleotides.

"Cell specific ligands" refer to any material or substance which may promote attachment of biological cells to microbubbles of the present invention. The cell specific ligand may be synthetic, semi-synthetic, or naturally-occurring. Materials or substances which may serve as a cell specific ligand include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, bioactive agents, and genetic material, including nucleosides, nucleotides, nucleotide acid constructs and polynucleotides.

"Microbubble stability" refers to the ability of microbubbles to retain the gas, gaseous precursor and/or other bioactive agents entrapped therein after being exposed, for example, for about one minute, to a pressure of about 100 millimeters (mm) of mercury (Hg). Microbubble stability is measured in percent (%), this being the fraction of the amount of gas which is originally entrapped in the microbubble and which is retained after release of the pressure. Microbubble stability also includes "microbubble resilience" which is the ability of a microbubble to return to its original size after release of the pressure.

"Cross-link," "cross-linked" and "cross-linking" generally refer to the linking of two or more stabilizing materials, including lipid, protein, polymer, carbohydrate, surfactant stabilizing materials and/or bioactive agents, by one ore more bridges. The bridges may be composed of one or more elements, groups, or compounds, and generally serve to join an atom from a first stabilizing material molecule to an atom of a second stabilizing material molecule. The cross-link bridges may involve covalent and/or non-covalent associations. Any of a variety of elements, groups, and/or compounds may form the bridges in the cross-links, and the stabilizing materials may be cross-linked naturally or through synthetic means. For example, cross-linking may occur in nature in material formulated from peptide chains which are joined by disulfide bonds of cysteine residues, as in keratins, insulins and other proteins. Alternatively, cross-linking may be effected by suitable chemical modification, such as, for example, by combining a compound, such as a stabilizing material, and a chemical substance that may serve as a cross-linking agent, which may cause to react by, for example, exposure to heat, high-energy radiation, ultrasonic radiation and the like. Examples include cross-linking by sulfur to form disulfide linkages, cross-linking using organic peroxides, cross-linking of unsaturated materials by means of high-energy radiation, cross-linking with dimethylol carbamate, and the like. If desired, the stabilizing compounds and/or bioactive agents may be substantially cross-linked. The term "substantially" means that greater than about 50% of the stabilizing compounds contain cross-linking bridges. If desired, greater than about 60%, 70%, 80%, 90%, 95% or even 100% of the stabilizing compounds contain such cross-linking bridges. Alternatively, the stabilizing materials may be non-cross-linked, i.e., such that greater than about 50% of the stabilizing compounds are devoid of cross-linking bridges, and if desired, greater than about 60%, 70%, 80%, 90%, 95% or even 100% of the stabilizing compounds are devoid of cross-linking bridges.

The term "attached" or "association" as used herein, refers to any interaction between, for example, a microbubble and a biological cell. Attachment may comprise a reversible association or an irreversible association. Such attachment may be, but is not limited to, covalent bonding, ionic bonding, Van de Waal forces or friction, and the like. A compound is attached to a medium or carrier if it is impregnated, incorporated, coated, in suspension with, in solution with, mixed with, etc.

"Covalent association" refers to an intermolecular association or bond which involves the sharing of electrons in the bonding orbitals of two atoms.

"Non-covalent association" refers to intermolecular interaction among two or more separate molecules which does not involve a covalent bond. Intermolecular interaction is dependent upon a variety of factors, including, for example, the polarity of the involved molecules, and the charge (positive or negative), if any, of the involved molecules. Non-covalent associations are selected from ionic interactions, dipole-dipole interactions, van der Waal's forces, and combinations thereof.

"Ionic interaction" or "electrostatic interaction" refers to intermolecular interaction among two or more molecules, each of which is positively or negatively charged. Thus, for example, "ionic interaction" or "electrostatic interaction" refers to the attraction between a first, positively charged molecule and a second, negatively charged molecule. Ionic or electrostatic interactions include, for example, the attraction between a negatively charged stabilizing material, for example, genetic material, and a positively charged lipid, for example, a cationic lipid, such as lauryltrimethylammonium bromide.

"Dipole-dipole interaction" refers generally to the attraction which can occur among two or more polar molecules. Thus, "dipole-dipole interaction" refers to the attraction of the uncharged, partial positive end of a first polar molecule, commonly designated as $\Delta^+$, to the uncharged, partial negative end of a second polar molecule, commonly designated as $\Delta^-$. Dipole-dipole interactions are exemplified by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole-dipole interaction" also refers to intermolecular hydrogen bonding in which a hydrogen atom serves as a bridge between electronegative atoms on separate molecules and in which a hydrogen atom is held to a first molecule by a covalent bond and to a second molecule by electrostatic forces.

"Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

"Hydrogen bond" refers to an attractive force, or bridge, which may occur between a hydrogen atom which is bonded covalently to an electronegative atom, for example, oxygen, sulfur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

"Hydrophobic interaction" refers to molecules or portions of molecules which do not substantially bind with, absorb and/or dissolve in water.

"Hydrophilic interaction" refers to molecules or portions of molecules which may substantially bind with, absorb and/or dissolve in water. This may result in swelling and/or the formation of reversible gels.

"Tissue" refers generally to specialized cells which may perform a particular function. The term "tissue" may refer to an individual cell or a plurality or aggregate of cells, for example, membranes, blood or organs. The term "tissue" also includes reference to an abnormal cell or a plurality of abnormal cells. Exemplary tissues include myocardial tissue, including myocardial cells and cardiomyocytes, membranous tissues, including endothelium and epithelium, laminae, connective tissue, including interstitial tissue, and tumors.

"Receptor" refers to a molecular structure within a cell or on the surface of a cell which is generally characterized by the selective binding of a specific substance. Exemplary receptors include cell-surface receptors for peptide hormones, neurotransmitters, antigens, complement fragments, immunoglobulins and cytoplasmic receptors for steroid hormones.

"Extracellular" refers to the area encompassing the outer plasma membrane of a cell, including the phospholipid bilayer and associated proteins, glycolipids, receptors etc.

"Progenitor cell" as used herein, refers to an ancestral cell in a direct line of descendent cells, where the descendent cells follow different developmental and differentiation pathways. Under the proper circumstances (i.e., for example, contact with a specific tissue) any one progenitor cell can be induced to develop and mature into the contacted tissue. For example, an endothelial progenitor cell may develop into mature endothelial tissue subsequent to coming into contact with endothelial tissue.

BRIEF DESCRIPTION OF THE FIGURES

FIG. 9 presents exemplary data showing quantification of microbubble coating of progenitor cells using flow cytometry. The flow plots depict the FSC/SSC profile (left column) and the distribution of SSC (right column) of fluorescently labeled MSC alone (A), after mixing with cationic microbubbles at MSC to microbubble mix ratio of 1:40 (B) and 1:400 (C), and after mixing with control negatively charged microbubbles (ratio of 1:400, D). In the FSC/SSC plots, the fluorescent events (i.e. MSCs) are in green, while the black events represent microbubbles. MSC association with the cationic microbubbles (B and C) leads to increased SSC of the cells (blue color plots) relative to MSCs alone (A) and to control microbubbles (D). The increase in side scatter correlates with the proportion of cells coated with microbubbles as identified by microscopy (E), while the average SSC (for the cells with increased SSC) correlated with the average number of microbubbles per MSC (F).

FIG. 11 presents a representative characterization of acoustic energy for cell delivery using an existing intravascular ultrasound catheter. One embodiment of a suitable intravenous RF catheter is shown (i.e., for example, an EkoSonic SV catheter, Ekos Corp, Bothell, Wash.

FIG. 15 presents one embodiment of an in vivo endoluminal cellular paving using acoustic radiation force. A. In vivo experimental setup: An occlusion balloon infusion catheter was inflated proximal to sites of angioplasty-induced denudation in the descending thoracic aorta in rabbits. Mb-MSCs were injected through the central lumen of this balloon catheter, while ultrasound was delivered to injured region using an intravascular ultrasound catheter. B. Low magnification en face imaging of the endoluminal side of an aortic segment 20 min after delivery of mb-MSCs, showing minimal single fluorescent MSC adhesion in a control proximal segment unexposed to ultrasound (Control, B1), whereas numerous MSCs (arrowheads) adhered to the ultrasound-treated areas (Ultrasound, B2). Scale bar 200 mm C. Quantification of the density of retained MSCs for control conditions (black circles), low (0.5 MPa, blue squares) and high (1 MPa, red triangles) acoustic radiation force. * $p<0.05$, ** $p<0.01$ vs control, n=6-7.

DETAILED DESCRIPTION OF THE INVENTION

Figure 1:
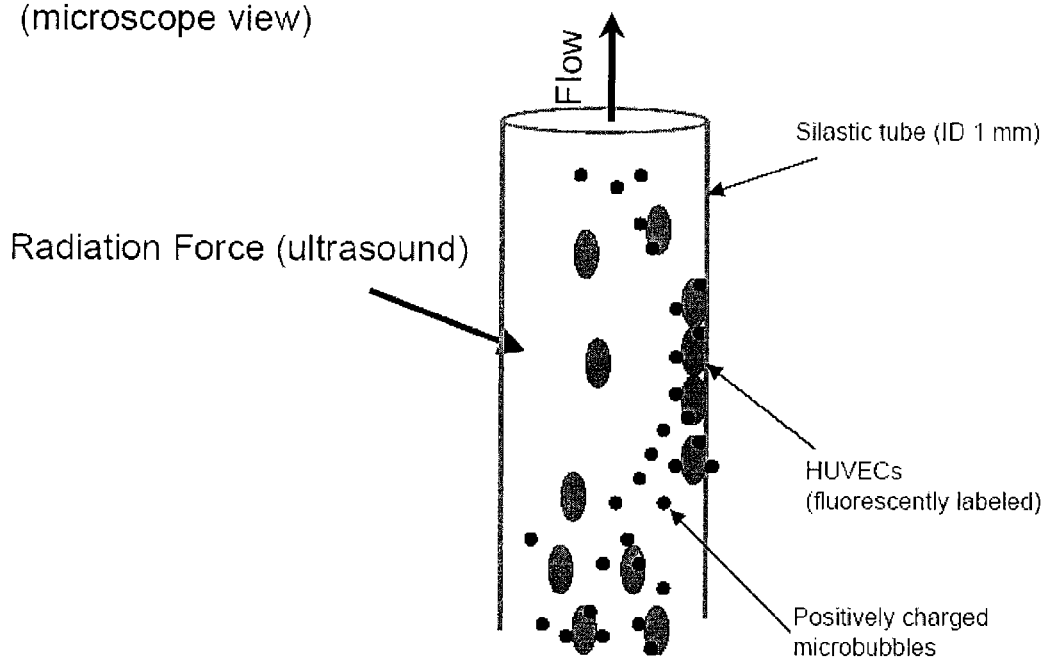
FIG. 1 illustrates an in vitro testing model to demonstrate the feasibility of acoustic radiation force mediated cell delivery. Positively charged microbubbles are moved along a silastic tube using acoustic radiation until contacting human umbilical vascular endothelial (HUVEC) cells. A vessel phantom was made using a polyvinyl chloride (PVC) tube (internal diameter 1 mm) placed in a water tank and under a fluorescence microscope (BX51, Olympus). A 5 MHz ultrasound transducer was immersed perpendicular to the flow direction, with the ultrasound focused at the optical focus.

The present invention is related to the field of cell based therapy. For example, tissue regeneration and healing may be mediated by an increased presence of biologically active progenitor cells. For example, accelerated endothelial tissue growth may be accomplished following certain cardiovascular surgical procedures and/or vascular injury, insertion of a stent, or after a balloon angioplasty procedure by increasing the presence of endothelial progenitor cells. Such endothelial cell growth may be accelerated by administering a microbubble composition comprising personalized endothelial progenitor cells. For example, such endothelial growth may reduce thrombotic complications associated with these devices and to increase patency.

In one embodiment, the present invention contemplates a targeted selective displacement of progenitor and/or other therapeutic cells to an area of interest in the body using a microbubble coating in conjunction with acoustic energy. For example, the method may comprise an in vivo method wherein MSCs are delivered to an injured artery using a commercially available catheter (Ekos) using custom ultrasound parameters.

Although it is not necessary to understand the mechanism of an invention, it is believed that a cell-based approach may present an attractive solution to restoration of a functional endothelium. For example, endothelial progenitor cells (EPCs), such as $CD34^+/Kdr^+$ mononuclear cells, are believed to be present in low numbers in the systemic circulation. Culture-expanded EPCs have been shown to attenuate atherosclerosis progression in $ApoE^{-/-}$ mice. Rauscher et al., "Aging, progenitor cell exhaustion, and atherosclerosis" *Circulation* 108:457-463 (2003). It has also been reported that stents coated with targeting peptides for circulating EPCs may accelerate endothelial coverage as compared to controls. Aoki et al., "Endothelial progenitor cell capture by stents coated with antibody against CD34:the HEALING-FIM Registry" *J Am Coll Cardiol.* 45:1574-1579 (2005); and Blindt et al., "A novel drug-eluting stent coated with an integrin-binding cyclic Arg-Gly-Asp peptide inhibits neointimal hyperplasia by recruiting endothelial progenitor cells" *J Am Coll Cardiol.* 47:1786-1795 (2006). Another potential therapeutic cell may involve the bone marrow derived $CD90^+/105^+/73^+$ mesenchymal stem cell (MSCs). Recent data indicate that MSCs restore functional endothelium and reduce neointimal formation in rodents following vascular injury. Yue et al., "Mesenchymal stem cells differentiate into an endothelial phenotype, reduce neointimal formation, and enhance endothelial function in a rat vein grafting model" *Stem Cells Dev.* 17:785-793 (2008); Forte et al., "Mesenchymal stem cells effectively reduce surgically induced stenosis in rat carotids" *J Cell Physiol.* 217:789-799 (2008); and Wang et al., "Late-outgrowth endothelial cells attenuate intimal hyperplasia contributed by mesenchymal stem cells after vascular injury" *Arterioscler Thromb Vasc Biol.* 28:54-60 (2008).

One limitation to the successful development of cell therapy to a specific vascular segment has been the lack of an effective delivery method under the conditions of high shear stress that exist in the arteries. Various embodiments of the presently contemplated invention present solutions to this problem. For example, one solution comprises a catheter-based, minimally disruptive method for selective cell delivery based on ultrasound radiation force. Although it is not necessary to understand the mechanism of an invention, it is believed that ultrasound radiation force refers to the kinetic energy transferred to a deformable object (i.e., for example, an acoustically active microbubble as described herein) by absorption of acoustic energy thereby leading to the deformable object's displacement away from the energy source. It has been reported that radiation force is proportional to the compressibility of the object, and may be maximal when the incident ultrasound frequency is equal to the natural resonating frequency of the object. Gas-filled microbubble contrast agents have been reported as susceptible to the displacement effects of radiation force exerted by ultrasound. Dayton et al., "Acoustic radiation force in vivo: a mechanism to assist targeting of microbubbles" *Ultrasound Med Biol.* 25:1195-1201 (1999); and Dayton et al., "The magnitude of radiation force on ultrasound contrast agents" *J Acoust Soc Am.* 112:2183-2192 (2002).

In one embodiment, the present invention contemplates a method of applying an acoustic radiation force to selectively displace microbubble-coated therapeutic cells to a specific tissue target. In one embodiment, the tissue target is a diseased and or damaged tissue target. In one embodiment, the microbubble-coated therapeutic cells adhere to (i.e., for example, by attaching and/or binding) the tissue target under conditions such that the diseased and/or damaged tissue target regenerates thereby healing the diseased and/or damaged tissue.

Figure 8:
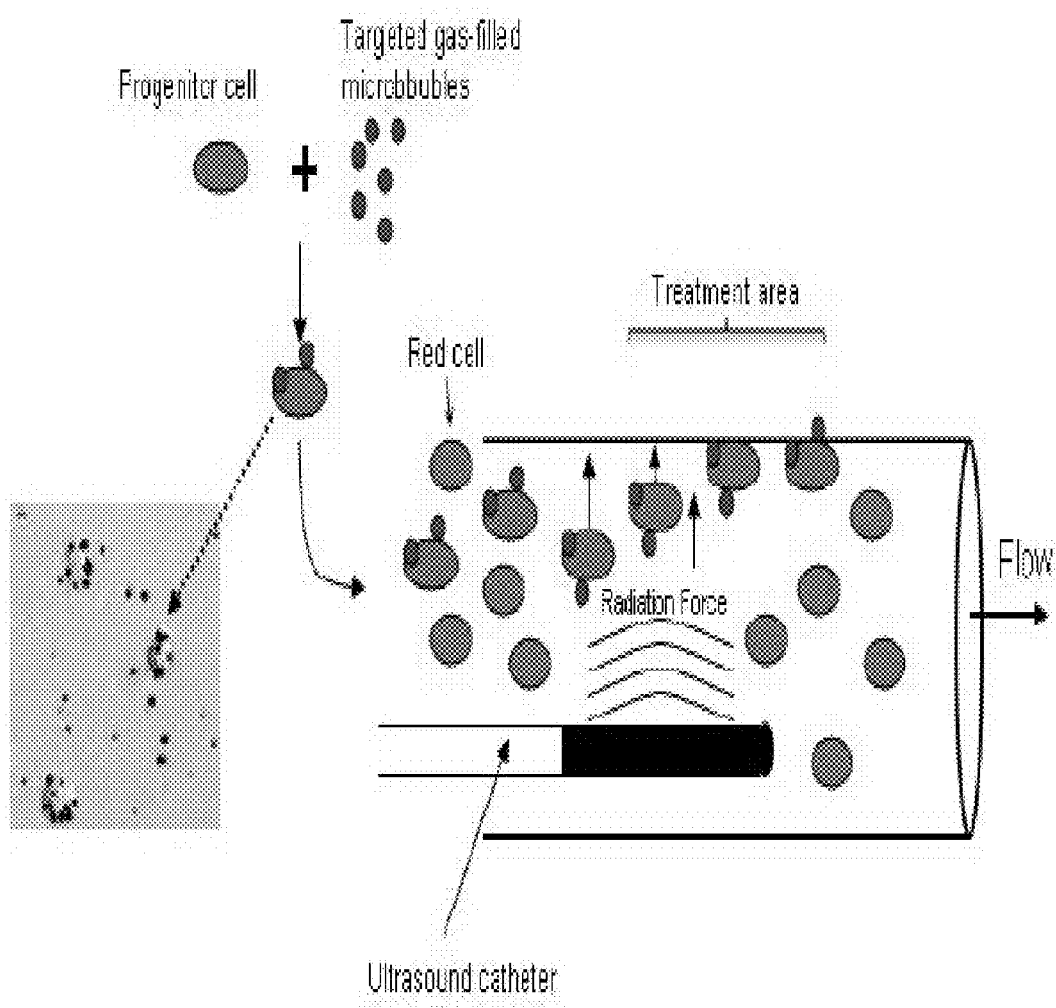
FIG. 8 presents one embodiment of a testing model for an acoustic RF method to demonstrate endoluminal cellular paving. This testing model has been utilized to demonstrate proof of principle for some embodiments of the present invention. Progenitor cells (green ovals) are labeled with gas-filled microbubbles (red circles). An intravascular ultrasound catheter capable of emitting ultrasound radially is placed in the area of interest. As the cell:bubble complexes are injected upstream, RF is applied driving the cell:bubble complexes to the endothelia where the cells adhere to endothelial surface. Inset: an exemplary photomicrograph showing MSCs coated with cationic lipid microbubbles as contemplated herein).

A schematic is presented herein that illustrates the concept of ultrasound radiation force-mediated delivery of progenitor cells for vascular endothelialization. For example, therapeutic cells can be coated with gas-filled acoustically active microbubbles, using either non-specific electrostatic interactions or specific binding via targeting moieties on the bubble's surface. The microbubble cell complexes are then intravascularly introduced proximal to the area of interest. An intravascular ultrasound catheter capable of emitting ultrasound radially is placed at the level of the tissue target (i.e., for example, an arterial segment to be treated). As the microbubble-coated cells pass by the probe, the microbubble-coated cells are selectively displaced peripherally by the acoustic radiation force, thus facilitating cell adhesion to the vessel wall. See, FIG. 8. The above described test model validated the overall concept that: i) progenitor cells can be coated with acoustically active microbubbles using either ligand specific or electrostatic interactions; ii) the cell:microbubble complexes can be infused upstream of a specific site in a luminal vessel (i.e., for example, an arterial area of injury); iii) an ultrasound catheter is capable of delivering acoustic energy in a radial direction when placed at the level of a specific site in a luminal vessel; iv) as the cell:microbubble complexes flow in the vicinity of the catheter, the complexes are displaced by the acoustic radiation force to the periphery of the luminal vessel resulting in cell attachment and seeding on the luminal vessel wall.

The data presented herein demonstrate such a cell delivery method using MSCs. It should be realized that MSC's are not the only cells that may be successfully used in this method, and are utilized herein only as one example. The conclusions of the data shown herein suggest that ultrasound radiation force can effectively displace microbubble-coated cells (i.e., for example MSCs) under physiologic vascular flow conditions in an in vitro vessel phantom. Alternatively, microbubble-coated cells can by directed using ultrasound radiation force to effectively seeded on, and survive within, an in vivo denuded arterial segment.

I. Endothelial Tissue Healing

Acceleration of stent endothelial cell coverage requires an improvement of a natural phenomenon usually occurring at a relatively slow pace. For example, therapies for bare metal stents (BMS) and drug eluting stents (DES), require prolonged antiplatelet therapy to accommodate to delayed endothelialization rates. Accelerated endothelialization may also be expected to decrease thrombosis rates, decrease restenosis occurrence, in addition to promoting rapid healing of the coronary segment injured by the stenting procedure. To date, there are no available drug therapies that address this problem.

One strategy to address endothelial deficiency/dysfunction is to promote re-endothelialization by actively repopulating diseased and/or injured vascular segments with mesenchymal stem cells (MSCs). MSCs are bone marrow derived cells isolated by their adhesion to tissue culture dishes. Pittenger et al., "Multilineage potential of adult human mesenchymal stem cells" *Science* 284(5411):143-147 (1999). The MSCs are potent paracrine secretors and have been reported to reduce inflammation and/or induce angiogenesis when transplanted in ischemic tissues. Caplan et al., "Mesenchymal stem cells as trophic mediators" *J Cell Biochem.* 98(5):1076-1084 (2006); and Gnechi et al., "Evidence supporting paracrine hypothesis for Akt-modified mesenchymal stem cell-mediated cardiac protection and functional improvement" *FASEB J.* 20(6):661-669 (2006). MSCs may also have a favorable effect on vascular healing following angioplasty in animal models. Forte et al., "Mesenchymal stem cells effectively reduce surgically induced stenosis in rat carotids" *J Cell Physiol.* 217(3):789-799 (2008). However, an efficient and predictable delivery method to accomplish cell therapy directly to a vascular segment without mechanical trauma to the vessel wall was, until the present invention, unavailable.

While targeted drug delivery uses microspheres with attached targeting ligands, these microspheres deliver incorporated and/or encapsulated drugs to a specific biological target. Consequently, these compositions are not useful for contacting a progenitor cell with a tissue to stimulate maturation and differentiation of the progenitor cell. Keegan et al. "Biodegradable Microbubbles With Enhanced Capacity For Covalently Bound Surface Ligands" *Macromolecules* 37(26): 9779-9784 (2004).

The present invention contemplates attaching biological progenitor cells to the exterior surface of microbubbles for presentation to a target tissue. For example, endothelial progenitor cells (EPCs) are believed to be a rare population of mononuclear cells present in the systemic circulation (i.e., for example, approximately 1000 cells/nil). Vascular injury can dramatically increase the number of EPCs thereby participating in angiogenesis and endothelialization. Although it is not necessary to understand the mechanism of an invention, it is believed that EPCs participate in the endothelialization of prosthetic material that comes into direct contact with blood. EPCs also may possess a unique combination of CD markers including, but not limited to, VEGFR2, CD34, or CD133). Under some circumstances EPCs may also modulate specific integrin expression.

Currently, methods available that attempt to deliver EPCs to cardiovascular systems (i.e., for example, a vascular segment) are largely unproven. For example, one technology attempts to stimulate rapid stent endothelialization using a stent covered with CD34 antibodies (Genous, Orbus-Neich) are still in European clinical trials. Even so, it is expected that these stents will incur significant problems associated with restenosis (i.e., the re-narrowing a vascular segment following stent implantation). Although it is not necessary to understand the mechanism of an invention, it is believed that the occurrence of restenosis negatively correlates with the number of local endothelial progenitor cells.

Endothelial progenitor cell (EPC) capture stents have been used in primary percutaneous intervention following ST-elevation myocardial infarction (STEMI). Ninety-five percent of patients responded with thrombolysis having cumulative major adverse cardiac event rates at: i) 1.6% in-hospital; ii) 4.2% at 30 days; iii) 5.8% at 6 months; iv) and 9.2% at 1 year. Co et al., "Use of endothelial progenitor cell capture stent (Genous Bio-Engineered R Stent) during primary percutaneous coronary intervention in acute myocardial infarction: intermediate-to-long term clinical follow-up" *Am Heart J.* 155:128-132 (2008).

In one embodiment, the present invention contemplates a system providing patient-tailored therapy (i.e., for example, 'personalized' EPC tagging of microbubbles) that utilize the patient's own progenitor cells to provide the therapeutic response. To maximize the amount of collected EPCs from any one person, additional blood can be processed and/or a longer treatment period can be applied. In one embodiment, the present invention contemplates a method having distinct and significant advantages over current antibody-coated stents in that EPC-coated stents (i.e., for example, personalized EPC-coated stents) result in a complete overgrowth of the stent struts in addition to stimulating the growth of the adjacent (injured) artery wall. In other words, the stent acts as scaffold, and when the stent is deployed, the metal coverage represents only 10-20% of the stented segment.

In one embodiment, the present invention contemplates a method for specific cell-based therapy of a particular vascular segment. Although it is not necessary to understand the mechanism of an invention, it is believed that this embodiment draws from emerging insights into the biology of EPC-mediated vascular repair, and uniquely combines principles of acoustic physics, microbubble engineering and molecular targeting, to therapeutically enhance that repair. Using progenitor cell-microbubble complexes, this method combines selection of a cell of interest (i.e., for example, a progenitor cell), with a microbubble delivery system having a potential for real time monitoring of the delivery. Such real time monitoring can be accomplished by IVUS imaging of the microbubble-cell complexes deposition on the arterial wall. These methods find use for the treatment of medical conditions including, but not limited to, coronary or peripheral lesions with percutaneous catheter based technology, stent thrombosis and/or an alternative for antiplatelet therapy. In particular, one embodiment of the present invention contemplates treating stented blood vessel segments following an index procedure, independent of the stent used.

II. Cell-Based Therapy Tissue Regeneration

Many disease states and tissue injury depend upon tissue regeneration for complete recovery. Such therapeutic approaches has not been successfully treated with drug and/or pharmacological therapies. For example, the failure of the normal protective functions of the vascular endothelium is the hallmark of atherosclerotic cardiovascular disease, leading to the formation of arterial plaques as well as insufficient repair of sites of arterial injury. Ross R., "The Arterial Wall And Atherosclerosis" *Annu Rev Med.* 30:1-15 (1979). Whereas normal endothelium is inherently antithrombotic, dysfunctional coronary endothelium facilitates thrombosis, which leads to the acute coronary syndromes. As such, restoration of the functional and structural integrity of coronary endothelium in the setting of coronary artery disease is a therapeutic technique that could have significant impact on morbidity and mortality from coronary heart disease.

The data presented herein describes a method for delivering a specific cell-based therapy of a particular vascular segment. Emerging insights into the biology of EPC and MSC-mediated vascular repair, combined with principles of acoustic physics, microbubble engineering and molecular targeting, have all been integrated to develop a superior and advantageous therapeutic method using cell:microbubble complex compositions. In some embodiments, the method is capable of treating coronary or peripheral arterial lesions with percutaneous catheter-based technology, and high risk patients for stent thrombosis or who cannot tolerate antiplatelet therapy. Furthermore, the disclosed method allows for treatment of stented segments after the index procedure, independent of the stent used, if an increased risk for stent thrombosis is a concern (for instance if antiplatelet therapy has to be discontinued).

RF catheter-based technology, as disclosed herein, has numerous applications:

a. Stent or vascular graft endothelialization, vulnerable plaques, modulate the thickness of a fibrotic cap, or to attenuate lesion inflammatory responses.

b. Microbubbles loaded with drugs or gene therapy may be delivered to a vessel wall. RF-based targeting of paclitaxel-loaded microbubbles to tumors has been already demonstrated. Dayton et al., "Application of ultrasound to selectively localize nanodroplets for targeted imaging and therapy" *Mol Imaging* (3):160-174 (2006). A similar approach could be employed to deliver antirestenotic drugs to the vessel wall as a drug delivery platform.

c. Combined RF targeted microbubbles delivery with IVUS imaging catheters following microbubble interaction with a vessel wall (i.e., for example, stent endothelialization imaging).

In one embodiment, the present invention contemplates a method to treat endothelial dysfunction by directly promoting coronary re-endothelialization. In one embodiment, diseased and/or injured tissues are actively repopulated with endothelial progenitor cells (EPCs). Although it is not necessary to understand the mechanism of an invention, it is believed that EPCs are bone marrow derived cells that share surface markers and a common progenitor with the hematopoetic stem cells (HSCs). EPCs are believed to: i) represent 0.1-2% of the circulating mononuclear cells (MNCs); ii) mobilized in blood in response to vascular injury; and iii) contribute to neovascularization, both directly and via local paracrine mechanisms. Rafii et al, "Therapeutic stem and progenitor cell transplantation for organ vascularization and regeneration" *Nat Med.* 9:702-712 (2003); and Kawamoto et al., "Role of progenitor endothelial cells in cardiovascular disease and upcoming therapies" *Catheter Cardiovasc Interv.* 70:477-484 (2007). EPCs can also be mobilized by a variety of cytokines such as GM-CSF and erythropoietin, as well as statins. Llevadot et al., "HMG-CoA reductase inhibitor mobilizes bone marrow-derived endothelial progenitor cells" *J Clin Invest* 108:399-405 (2001). Systemic mobilization of the EPCs or intravenous administration leads to successful re-endothelialization of denuded arterial segments. He et al., "Transplantation of circulating endothelial progenitor cells restores endothelial function of denuded rabbit carotid arteries" *Stroke* 35:2378-2384 (2004); however, this strategy may have unwanted systemic angiogenic effects, as well as potential dual-edge effects resulting in plaque growth from vasa vasorum angiogenesis. Versari et al., "The importance of reendothelialization after arterial injury" *Curr Pharm Des.* 13:1811-1124 (2007).

In contrast to current technologies that attempt to systemically mobilize EPCs (i.e., for example, capture antibody stents), some embodiments described herein comprise methods that enhance restoration of functional endothelium by enhancing the physical interaction of naturally occurring circulating EPCs with the vessel wall. One signification problem that has prevented successful cell-based therapies is that EPCs have to overcome significant hydrodynamic forces of blood flow to find, and adhere to, the vessel wall. In some embodiments, the present invention contemplates new technologies that combine ultrasound energy in conjunction with gas-filled microspheres to achieve local luminal delivery of cells to a biological target tissue (i.e., for example, a vascular tissue segment).

B. Drug Eluting Stents

The introduction of drug-eluting stents (DES) is considered one of the major advancements in cardiac care in this past decade, with dramatic reduction in restenosis rates. One of problems emerging with the wide clinical application of DES is the potential for increased stent thrombosis, sometimes occurring very late following the index procedure, with devastating clinical sequelae. This is thought to be due to delayed healing of the vessel wall, possibly related to the effects of the drug or the eluting polymer, resulting in incomplete coverage of the stents struts by functional endothelium. Takano et al., "Serial long-term evaluation of neointimal stent coverage and thrombus after sirolimus-eluting stent implantation by use of coronary angioscopy" *Heart* 93:1353-1356 (2007). Moreover, in clinical practice many patients are not candidates for the prolonged dual antiplatelet therapy that has been advocated to reduce the risk of stent thrombosis. Popma et al., "FDA advisory panel on the safety and efficacy of drug-eluting stents: summary of findings and recommendations" *J Interv Cardiol.* 20:425-446 (2007). Alternative technologies are being developed, geared towards accelerated stent endothelialization using CD34 antibody or RGD peptide coated stents, designed to capture circulating endothelial progenitor cells (EPCs) from the circulation. Aoki et al., "Endothelial progenitor cell capture by stents coated with antibody against CD34: the HEALING-FM (Healthy Endothelial Accelerated Lining Inhibits Neointimal Growth-First In Man) Registry" *J Am Coll Cardiol.* 45:1574-1579 (2005); and Blindt et al., "A novel drug-eluting stent coated with an integrin-binding cyclic Arg-Gly-Asp peptide inhibits neointimal hyperplasia by recruiting endothelial progenitor cells" *J Am Coll Cardiol.* 47:1786-1795 (2006). The combination of a drug eluting stent with EPCs mobilization results in accelerated healing. Cho et al., "The effect of stem cell mobilization by granulocyte-colony stimulating factor on neointimal hyperplasia and endothelial healing after vascular injury with bare-metal versus paclitaxel-eluting stents" *J Am Coll Cardiol.* 48:366-374 (2006). In one embodiment, the present invention contemplates a method comprising a cell-based therapy for the accelerating endothelialization of the stented arterial wall. Although it is not necessary to understand the mechanism of an invention, it is believed that that such a method can have a significant impact for patients at risk for stent thrombosis.

C. Endothelial Tissue Regeneration

In some embodiments, the present invention couples principles of acoustic physics with state-of-the-art concepts in reparative cell therapy, along with new technology design, to enhance vascular healing in atherosclerotic disease (i.e., for example, heart disease). For example, these embodiments can improve percutaneous coronary intervention outcomes by reducing thrombotic complications, which lead to additional morbidity and mortality in patients with coronary artery disease. Furthermore, the concepts and technology established through this invention can be extended to other therapeutic applications both within and outside of cardiovascular medicine The technology for treating symptomatic atherosclerotic plaque has progressed from simple balloon angioplasty to intracoronary placement of bare metal stents (BMS) and more recently, to the usage of drug eluting stents (DES). However, problems are emerging, resulting from the delayed healing of the coronary artery at the site of the lesion, leading to stent thrombosis, sometimes late after the index procedure.

Specifically, percutaneous intervention (PCI) with drug eluting stents has been used to treat symptomatic atherosclerotic blockages in the coronary arteries. Current problems with these vascular scaffold stents include, but are not limited to, slow healing, slow tissue integration, and prolonged treatment with blood thinners to prevent thrombosis. The data presented herein demonstrate progenitor cell paving on the inside of a stent-treated artery. Further, acoustic energy may be generated by a catheter inside the vessel, that selectively drives the progenitor cells towards an preselected target (i.e., for example, injured endothelial tissue). Although it is not necessary to understand the mechanism of an invention, it is believed that once the progenitor cells bind to the endothelial tissue, a regeneration of normal endothelial lining occurs resulting in the creation of healthy arteries.

In one embodiment, the present invention contemplates a method comprising an endoluminal cellular paving of a stented surface with cells capable of regenerating functional endothelium. In one embodiment, the paving comprises using acoustic radiation force to direct the cells to the endothelial surface. Although it is not necessary to understand the mechanism of an invention, it is believed that acoustic radiation force technology displaces compressible objects within an ultrasound field away from an energy source due to absorption of a sound wave momentum (i.e., for example, Bjerkens force). In one embodiment, the cell paving comprises using gas-filled lipid microbubbles that are also capable of being used as ultrasound contrast agents. In one embodiment, a centrally placed intravascular US catheter comprise progenitor cells coated with microbubbles. In one embodiment, the catheter releases the microbubble-coated cells for interaction with an endothelial margin, wherein the margin comprises an injured arterial surface.

Atherosclerosis initiation and progression may result from a dysfunctional endothelium, allowing for increased permeability and deposition of macrophages in the subintimal space. Ross R., "The arterial wall and atherosclerosis" *Annu Rev Med* 30:1-15 (1979). It has been proposed that circulating EPCs actively engraft and help replace damaged endothelium, but this mechanism diminishes with age and becomes insufficiently protective. Versari et al., "The importance of reendothelialization after arterial injury" *Curr Pharm Des.* 13:1811-1824 (2007). Administering exogenous EPCs in ApoE deficient mice results in remarkable reduction in: i) aortic atherosclerotic plaques. Dong et al., "Endothelial progenitor cells: a promising therapeutic alternative for cardiovascular disease" *J Interv Cardiol.* 20:93-99 (2007); and ii) neo-intimal formation after injury. Zeng et al., "HDAC3 is crucial in shear- and VEGF-induced stem cell differentiation toward endothelial cells" *J Cell Biol.* 174:1059-1069 (2006). Major efforts have been directed at identifying plaque vulnerability, with current technology being able to identify thin-cap fibroatheromas with a rich lipid core that are prone to rupture. Young et al., "Vulnerable plaque intervention: State of the art" *Catheter Cardiovasc Interv.* 15:71(3):367-374 (2008). Nonetheless, there are no currently available conventional drug therapies to treat this condition.

Although it is not necessary to understand the mechanism of an invention, it is believed that a luminal cell-based restoration of a functional endothelium on these lesions may lead to plaque regression and stabilization and significantly reduce the incidence of acute coronary syndromes. In one embodiment, the present invention contemplates a method comprising a cell-based approach for treatment of atherosclerotic disease. In one embodiment, the atherosclerotic disease comprises rupture-prone plaques ("vulnerable plaques"). In one embodiment, the plaques are in the coronary arteries.

The data presented herein indicate that cell displacement using acoustic radiation force is possible. For example, such cell displacement is demonstrated in a vessel phantom at physiologic rates of flow. In one embodiment, the present invention contemplates using mesenchymal stem cells (MSCs) as a target progenitor cell and electrostatic interaction for cell:bubble association. Various microbubble compositions may be tested to determine optimal conditions for delivery of MSCs to the wall of a vascular phantom under physiologic flow conditions. For example, such optimization may be determined by the character and quantity of an association between MSCs and cationic microbubbles using flow cytometry, using a modified method that increases incident light side scatter (SSC) by the bubble-coated MSCs. A determination of optimal cell-microbubble association and ultrasound parameters for luminal delivery of cells in vitro, and in a coronary artery segment ex-vivo are also tested.

In one embodiment, the present invention contemplates a method comprising in vivo coronary stenting, using ultrasound-based radiation force for localized delivery of cell:microbubble complexes to an injured vascular segment in vivo. In one embodiment, the present invention contemplates a method for delivering MSCs using RF to a coronary artery. In one embodiment, the MSCs lead to accelerated healing and re-endothelialization following coronary stenting. Previous reports suggest that both endothelial progenitor cells (EPCs) or mesenchymal stem cells (MSCs) can participate in restoration of functional endothelium following vascular injury. He et al., "Transplantation of circulating endothelial progenitor cells restores endothelial function of denuded rabbit carotid arteries" *Stroke* 35:2378-2384 (2004); Cho et al., "The effect of stem cell mobilization by granulocyte-colony stimulating factor on neointimal hyperplasia and endothelial healing after vascular injury with bare-metal versus paclitaxel-eluting stents" *J Am Coll Cardiol.* 48(2):366-374 (2006); Conti et al, "Insulin-like growth factor-1 as a vascular protective factor" *Circulation* 110(15):2260-2265. (2004); Yue et al, "Mesenchymal stem cells differentiate into an endothelial phenotype, reduce neointimal formation, and enhance endothelial function in a rat vein grafting model" *Stem Cells Dev.* 17(4):785-793 (2008); Forte et al., "Mesenchymal stem cells effectively reduce surgically induced stenosis in rat carotids" *J Cell Physiol* 217(3):789-799 (2008); and Wang et al., "Late outgrowth endothelial cells derived from Wharton jelly in human umbilical cord reduce neointimal formation after vascular injury: involvement of pigment epithelium-derived factor" *Arterioscler Thromb Vasc Biol.* 29(6):816-822 (2009), respectively.

In one embodiment, the present invention contemplates a method comprising applying acoustic RF orthogonal to coronary flow thereby selectively displacing reparative cells from a catheter surface such that the cells become concentrated along an injured arterial wall. Although it is not necessary to understand the mechanism of an invention, it is believed that this method is advantageous and superior to delivery of cells by intra-arterial injection, because such systemically delivered cells would have to overcome significant hydrodynamic forces to adhere to the luminal surface of epicardial coronary arteries under physiologic flow conditions.

In one embodiment, the present invention contemplates a composition comprising cells of interest attached to a plurality of gas-filled microbubbles, wherein the microbubbles act as "sails" driven by acoustic energy. It is believed that the cell:microbubble complexes can be selectively driven with ultrasound energy to a preselected target tissue site. In one embodiment, the composition is coated upon an implantable stent. In one embodiment, the stent is bare. In one embodiment, the stent is drug-eluting.

In one embodiment, the present invention contemplates a method comprising EPCs and/or MSCs attached to microbubbles for endoluminal cellular paving of a stented area. Although it is not necessary to understand the mechanism of an invention, it is believed that the EPC's and/or MSCs will accelerate healing and restoration of injured endothelium. Alternative embodiments include cell-microbubbles further comprising drugs and/or genes for simultaneous treatment of a specific vascular segment.

1. Conditions for Proper Re-Endothelialization

Although it is not necessary to understand the mechanism of an invention, it is believed that endothelial cell coverage of a stented segment (i.e., for example, cellular paving) prevents stent thrombosis. Following coronary angioplasty and stenting, it is believed that significant injury to a arterial wall has occurred, with loss of endothelial coverage and local inflammation. Antiplatelet therapy has been reported to reduce the incidence of stent thrombosis following this procedure. Leon et al, "A clinical trial comparing three antithrombotic-drug regimens after coronary-artery stenting: Stent Anticoagulation Restenosis Study Investigators" *N Engl J Med.* 339(23): 1665-1671 (1998). While gradual re-endothelialization and healing of a stented segment may occur, this process is significantly delayed after placement of a DES in animal models. Joner et al., "Endothelial cell recovery between comparator polymer-based drug-eluting stents" *J Am Coll Cardiol.* 52(5): 333-342 (2009). Further, autopsy studies in patients with DES-induced thrombosis demonstrated substantial impairment in arterial healing, characterized by incomplete re-endothelialization and persistence of fibrin when compared with BMS. Finn et al., "Vascular responses to drug eluting stents: importance of delayed healing" *Arterioscler Thromb Vasc Biol* 27:1500-1510. (2007). Such impairments are also observed following DES use for the treatment of acute myocardial infarction. Nakazawa et al., "Delayed arterial healing and increased late stent thrombosis at culprit sites after drug-eluting stent placement for acute myocardial infarction patients: an autopsy study" *Circulation* 118(11):1138-1145 (2008).

Deleterious stent effects may also be related to cytotoxic effects of a coated drug and/or eluting polymer which, while therapeutically preventing re-stenosis, adversely inhibits reendothelialization. DES have been reported to induce endothelial dysfunction in the adjacent vascular segment, further suggesting deleterious effects on endothelial cells in the vascular segment adjacent to the stent. Hamilos et al., "NOBORI CORE Investigators. Differential effects of drug-eluting stents on local endothelium-dependent coronary vasomotion" *J Am Coll Cardiol.* 51(22):2123-2129 (2008). As yet unproven, new generation DESs are designed to circumvent some of these problems using biocompatible polymers and different drug eluting strategies. Other technologies under development are designed to accelerate stent endothelialization by coating stents with CD34 antibody or RGD peptide to capture circulating endothelial progenitor cells (EPCs) from the circulation. Aoki et al., "Endothelial progenitor cell capture by stents coated with antibody against CD34: the HEALING-FIM (Healthy Endothelial Accelerated Lining Inhibits Neointimal Growth-First In Man) Registry" *J Am Coll Cardiol* 45(10):1574-1579 (2005); and Blindt et al., "A novel drug-eluting stent coated with an integrin-binding cyclic Arg-Gly-Asp peptide inhibits neointimal hyperplasia by recruiting endothelial progenitor cells" *J Am Coll Cardiol* 47(9): 1786-1795 (2006). However, as yet, none of the technologies have been shown to prevent and/or treat post-stent or angioplasty procedure tissue injury.

2. Prevention of Re-Stenosis

Although it is not necessary to understand the mechanism of an invention, it is believed that restoration of functional endothelium prevents re-stenosis. Re-stenosis following PCI may result from a combination of negative arterial remodeling and neointimal hyperplasia, resulting from migration and proliferation of vascular smooth muscle cells from the arterial media. Smooth muscle migration and proliferation is believed to result in restenosis following stenting, wherein antiproliferative drugs including, but not limited to sirolimus and derivatives of paclitaxel, are coated on DES in an attempt to inhibit this process. Functional endothelium has been reported to be inherently antithrombotic, and may be responsible for remodeling of a vascular wall. Behrendt et al., "Endothelial function: From vascular biology to clinical applications" *Am J Cardiol* 90(10C):40L-48L (2002). In rabbit models of balloon injury, seeding the injured segment with endothelial cells or EPCs has been reported to prevent thrombosis, but also may reduce restenosis due to neo-intimal hyperplasia. Kong et al., "Enhanced Inhibition of Neointimal Hyperplasia by Genetically Engineered Endothelial Progenitor Cells" *Circulation* 109(14):1769-1775 (2004); and Conte et al., "Efficient repopulation of denuded rabbit arteries with autologous genetically modified endothelial cells" *Circulation* 89:2161-2169 (1994). A similar effect was observed in pigs when EPC-capturing stents were used. Blindt et al., "A novel drug-eluting stent coated with an integrin-binding cyclic Arg-Gly-Asp peptide inhibits neointimal hyperplasia by recruiting endothelial progenitor cells" *J Am Coll Cardiol* 47(9):1786-1795 (2006); and Kutryk et al., "In vivo endothelial progenitor cell seeding for the accelerated endothelialization of endovascular devices" *Am J Cardiol* 92:94 (2003).

3. Endoluminal Cellular Paving

In one embodiment, the present invention contemplates a method comprising cellular paving thereby accelerating vascular healing. The data presented herein indicate that timely restoration of functional endothelium promotes vascular healing following PCI-induced injury. Although it is not necessary to understand the mechanism of an invention, it is believed that endothelial dysfunction may be treated by directly promoting vascular re-endothelialization wherein injured vascular segments are actively repopulated with progenitor cells (i.e., for example, by cellular paving). In one embodiment, the present invention contemplates a method comprising endoluminal cellular paving to promote vascular re-endothelialization. In one embodiment, epithelial progenitor cells (EPCs) are delivered to an injured vascular site. In one embodiment, circulating epithelial cells (CECs) are delivered to an injured vascular site. In one embodiment, mesenchymal stem cells (MSCs) are delivered to an injured vascular site.

ECPs and CECs are believed to comprise a small fraction of mononuclear cells present in the blood, representing up to 0.2% and 6%, respectively, of the mononuclear cell fraction. Duda et al., "A protocol for phenotypic detection and enumeration of circulating endothelial cells and circulating progenitor cells in human blood" *Nat Protoc.* 2(4):805-810 (2007). EPCs may be bone marrow-derived cells that share surface markers and a common progenitor with the hematopoetic stem cells. EPCs can be mobilized in blood in response to vascular injury, including following angioplasty. Barsotti et al., "Role of endothelial progenitor cell mobilization after percutaneous angioplasty procedure" *Curr Pharm Des.* 15(10):1107-1122 (2009). Further, EPCs can contribute to neo-vascularization, both directly and via local paracrine mechanisms. Rafii et al, "Therapeutic stem and progenitor cell transplantation for organ vascularization and regeneration" *Nat Med.* 9(6):702-712 (2003); and Kawamoto et al., "Role of progenitor endothelial cells in cardiovascular disease and upcoming therapies" *Catheter Cardiovasc Interv.* 70(4):477-484 (2007). Also, EPCs can be mobilized by a variety of cytokines such as GM-CSF and erythropoietin, as well as HMG-coA reductase inhibitors. Llevadot et al., "HMG-CoA reductase inhibitor mobilizes bone marrow—derived endothelial progenitor cells" *J Clin Invest* 108:399-405 (2001). Systemic mobilization of the EPCs or intravenous administration leads to re-endothelialization of denuded arterial segments or stented arteries. He et al., "Transplantation of circulating endothelial progenitor cells restores endothelial function of denuded rabbit carotid arteries" *Stroke* 35:2378-2384 (2004); and Cho et al., "The effect of stem cell mobilization by granulocyte-colony stimulating factor on neointimal hyperplasia and endothelial healing after vascular injury with bare-metal versus paclitaxel-eluting stents" *J Am Coll Cardiol.* 48(2):366-374 (2006), respectively. However, this strategy may have unwanted systemic angiogenic effects, as well as a potential dual-edge effect resulting in plaque growth from vasa vasorum angiogenesis. Versari et al., "The importance of reendothelialization after arterial injury" *Curr Pharm Des.* 13(17):1811-1824 (2007).

Mesenchymal stem cells (MSCs) are believed to represent a less explored alternative cell candidate than EPCs or CECs for promoting vascular healing. MSCs are also reported to represent a small subset of the nucleated cell fraction in the bone marrow (about 1 in 10,000 nucleated cells), that can be readily isolated and expanded based on their capacity to adhere on tissue culture plastic and which are able to differentiate into other mesodermal lineages. Pittenger et al., "Multilineage potential of adult human mesenchymal stem cells" *Science* 284(5411):143-147 (1999); Toma et al., "Human mesenchymal stem cells differentiate to a cardiomyocyte phenotype in the adult murine heart" *Circulation* 105(1):93-98 (2002); and Ucelli et al., "Mesenchymal stem cells in health and disease" *Nat Rev Immunol.* 8(9):726-736 (2008). MCs have already been used in humans primarily for their indirect regenerative and anti-inflammatory properties, in particular for graft-vs-host disease. Le Blanc et al., "Mesenchymal stem cells for treatment of steroid-resistant, severe, acute graft-versus-host disease: a phase II study. Developmental Committee of the European Group for Blood and Marrow Transplantation" *Lancet* 371(9624):1579-1586 (2008).

MSCs may have properties that are suitable for effective repair of the vascular endothelium. For example, MSCs have been reported to secrete an abundant array of proangiogenic cytokines, and may promote local angiogenesis. Kinnaird et al., "Bone-marrow-derived cells for enhancing collateral development: mechanisms, animal data, and initial clinical experiences" *Circ Res.* 95(4):354-363 (2004). MSCs may also be immuno-tolerated to support allotransplantation, and unlike EPCs, can be potentially used as an off-the-shelf product. Aggarwal et al., "Human mesenchymal stem cells modulate allogeneic immune cell responses" *Blood* 105(4):1815-1822 (2005). It has been suggested that there might be interplay between MSCs and the immune system, which could potentially decrease the local vascular inflammatory response to PCI. MSC-like cells exist in most organs as pericytes, raising the possibility that MSCs may play a role in vascular development. Crisan et al., "A perivascular origin for mesenchymal stem cells in multiple human organs" *Cell Stem Cell.* 3(3):301-313 (2008). Indeed, recent data indicate that MSCs restore functional endothelium and reduce neointimal formation in rodents following: i) vein grafting (Yue et al, "Mesenchymal stem cells differentiate into an endothelial phenotype, reduce neointimal formation, and enhance endothelial function in a rat vein grafting model" *Stem Cells Dev.* 17(4):785-793 (2008)); ii) surgical injury of the carotids (Forte et al., "Mesenchymal stem cells effectively reduce surgically induced stenosis in rat carotids" *J Cell Physiol* 217(3):789-799 (2008)), or iii) wire-injury of the endothelium (Wang et al., "Late outgrowth endothelial cells derived from Wharton jelly in human umbilical cord reduce neointimal formation after vascular injury: involvement of pigment epithelium-derived factor" *Arterioscler Thromb Vasc Biol.* 29(6):816-822 (2009)). MSCs attenuate the late smooth muscle growth associated with restenosis. Wu et al., "Effect of paclitaxel and mesenchymal stem cells seeding on ex vivo vascular endothelial repair and smooth muscle cells growth" *J Cardiovasc Pharmacol.* 46(6):779-786 (2005).

Clinically, systemic delivery of MSCs to address a local vascular injury may be disadvantageous and not effective, due to a limited capacity of these cells to freely circulate, as well as the potential for microembolism when large numbers of cells are systemically administered. Toma et al., "Fate of culture-expanded mesenchymal stem cells in the microvasculature: in vivo observations of cell kinetics" *Circ Res.* 104 (3):398-402 (2009). In some embodiments, the present invention contemplates several cell-based methods for repairing vascular injury (i.e., for example, following PCI). In one embodiment, a targeted delivery of a relatively small number of cells without the potential side effects of a systemic delivery would clearly be advantageous over the currently known systemic delivery methods (i.e., for example, intravenous injection).

III. Acoustic Models for Cell-Based Tissue Delivery

Effective forms of re-endothelialization therapy have been held back by a lack of technology providing a luminal delivery of a cell-based therapy to a specific arterial segment. In some embodiments, the present invention has solved those problems. In one embodiment, the present invention contemplates a method comprising using ultrasound to locally deliver a cell-based therapy to an injured arterial segment. In one embodiment, the cell-based therapy comprises vascular endoluminal cellular paving delivered by an acoustic radiation force. In one embodiment, the present invention contemplates a stent coated with a composition comprising a microbubble attached to an EPC, wherein the EPC comprises specific targeting ligands. In one embodiment, the composition is attached to the stent struts.

Systemically administered balloon-based drug delivery systems carrying cells on the surface of the balloon may not be applicable for cell delivery, as they may negatively impact cell viability. Similarly, injection of free cells upstream of a segment of interest is likely to be inefficient due to the limited physical interaction between the cells and the arterial wall due to circulatory currents and shear stress. Consequently, the cells will have to overcome significant hydrodynamic forces of blood flow to 'home in' and adhere to the vessel wall. Further disadvantages may result from a systemic circulation of free cells having potential unwanted systemic pro-angiogenic effects at distal tissue sites.

In one embodiment, the present invention contemplates a method for delivering cells including, but not limited to, CECs, EPCs, or MSCs, to a preselected vascular segment that avoids many of the above limitations to cell therapy for vascular healing. In one embodiment, the method comprises using acoustic radiation force. Although it is not necessary to understand the mechanism of an invention, it is believed that RF results from absorption of the incident wave momentum by particles leading to their displacement away from the ultrasound source. Leighton, The Acoustic Bubble. Academic Press, San Diego. 341:367.(1994); Chen et al., "Radiation force on a spherical object in an axisymmetric wave field and its application to the calibration of high-frequency transducers" *J Acoust Soc Am.* 99(2):713-724 (1996); Dayton et al., "The magnitude of radiation force on ultrasound contrast agents" *J Acoust Soc Am.* 112(5 Pt 1):2183-2192 (2002); and Zhao et al., "Radiation-force assisted targeting facilitates ultrasonic molecular imaging" *Mol Imaging* 3(3):135-148 (2004). RF effects are believed optimized when used to drive compressible objects, thereby greatly enhancing pressure placed upon gas-filled lipid microbubbles, and less on fluid filled particles, such as blood cells. Secondary Bjerkens forces are related to the interaction between bubbles in an ultrasonic field, and results in weak bubble attraction to each other.

Existing technology allows for microbubbles, which are 1-3 μm in diameter, to bear specific ligands, thus allowing targeted physical attachment of a microbubble to a cell of interest (i.e., for example, an MSC). Gas-filled microbubbles attached to a progenitor cell surface acts as a "sail" that allows movement of the cells in a direction dictated by the location of the ultrasound source. For example, a centrally placed ultrasound catheter in a coronary artery, may emit radially applied RF to force marginalization of microbubble:cell complexes passing in the vicinity of the catheter, facilitating cell adhesion to an injured and/or denuded vascular surface. See, FIG. 8. Such RF targeted delivery of microbubbles to a specific location has been reported for molecular imaging but not for solving the present problems of re-endothelialization. Dayton et al., "Application of ultrasound to selectively localize nanodroplets for targeted imaging and therapy" *Mol Imaging* 5(3): 160-174 (2006).

There are distinct advantages to employing acoustic radiation force to spatially manipulate cell movement. Theoretically, an ultrasound system can be configured to move cells precisely to a site determined by an acoustic focus, conferring an ability to achieve a high local density of therapeutic cells at a target site (i.e., for example, cellular paving). In addition to optimizing therapeutic effect, such spatial selectivity and enhanced local accumulation of delivered cells should decrease the number of systemically recirculating cells and associated untoward systemic effects (e.g. unwanted angiogenesis), as well as decrease distal microembolism resulting from non-adhesion of cells. Furthermore, ultrasound offers a potential not only for spatially deflecting cells towards a vessel wall, but also allows simultaneous imaging of this phenomenon, thus enabling concurrent visualization of the therapeutic intervention in real time. In one embodiment, cell:gas-filled microbubble complexes respond to acoustic RF and are acoustically visible. In one embodiment, acoustic visibility of the cell:gas-filled microbubble complex can be imaged using two dimensional ultrasound imaging. This capability allows for post-treatment assessment of treatment success, spatial extent of endoluminal paving, and whether additional RF treatments may optimize cell coverage of an injured vascular segment. In some embodiments, a distinct advantage of current treatments is that endoluminal paving combines a cell-based therapy with a simultaneous assessment of treatment efficacy simultaneously and using the same technology platform.

In one embodiment, the present invention contemplates a system comprising providing a cell, a microbubble, and an ultrasound catheter. In one embodiment, the system comprises at least one of many types of progenitor cells (supra). The data presented herein demonstrated RF-driven endoluminal cellular paving using MSC progenitor cells. Although it is not necessary to understand the mechanism of an invention, it is believed that culture expanded MSCs associate strongly with cationic lipid microbubbles based on an electrostatic interaction between microbubbles and the MSCs extracellular matrix. Clinical safety of autologous MSC administration has been demonstrated in humans, wherein MSCs are the only stem cell therapeutic currently designated by FDA as both as Orphan Drug and Fast Track product for graft-versus-host disease (osiris.com/clinical_trials.php).

In one embodiment, the system comprises a gas-filled microbubble comprising lipid-based ultrasound contrast agents such as those having been clinically used for ultrasound imaging. In some embodiments, the methods contemplated herein have a distinct advantages over those currently known by utilizing a minimal cationic microbubble dose as compared to much larger microbubble doses required for routine diagnostic ultrasound imaging methods. In one embodiment, the system comprises an ultrasound (US) catheter, wherein an acoustic force is maximal at frequencies near the resonant frequencies of microbubbles (i.e., for example, within the 2 MHz range). The intravascular ultrasound probes (IVUS) currently used for coronary imaging are inappropriate for use in the present invention as IVUS catheters operate at much higher frequencies (20-40 MHz). IVUS devices are designed to achieve spatial resolution, and require probe rotation or having a multiarray unit that is capable of circumferentially covering the vessel wall with ultrasound. In some embodiments, the present invention comprises a specific advantage of IVUS imaging devices in that a simple radially emitting central probe operating at low frequencies is ideal. Such catheters are commercially available (i.e., for example, EkoSonic SV, Ekos Inc (Bothell, Wash.); 1.7 MHz, duty-cycles up to 8.5%) and are FDA approved for coronary use (i.e., for example, facilitated thrombolysis).

A. In Vitro Validation Model

One in vitro model as described in Example I provides evidence that progenitor cells can be labeled with a gas filled microbubble, and that they can be effectively displaced and directed to adhere to the target surface using acoustic radiation force. See, FIG. 1. This in vitro model mimics a vascular structure and allows direct observation of the cells with microscopy. The data demonstrate that radiation force can be used to increase specific marginalization of microbubble tagged-cells under physiologic flow conditions. The cells used in this testing model were human umbilical vein endothelial cells (HUVECs) and the microbubbles were lipid based and positively charged. As a result, the microbubbles non-specifically associate with the negatively charged HUVECs. Control studies utilized negatively charged microbubbles (data not shown).

Using the in vitro validation model, CMRA-labeled mesenchymal stem cells (MSC) or human umbilical vein endothelial cells (HUVEC) were mixed with cationic microbubbles at different ratios (ratio of MSC to microbubbles 1:12, 1:40, and 1:400). Control experiments were performed with negatively charged microbubbles at 1:400 ratio. Mb-MSC complexes ($5 \times 10^4$ cells) were diluted in PBS and advanced through the vessel phantom at flow rates resulting in wall shear stress of 0.53 and 4.27 Pa, approximating the coronary wall shear stress during systole and diastole, respectively. The sidewall of the phantom opposite to the ultrasound transducer was continuously microscopically observed for 15 s during simultaneous perfusion with mb-MSCs, with ultrasound being turned on for the middle 5 s of the experimental run. The number of cells adhering or intermittently adherent to the wall (adherent+rolling fraction), as well as the number of cells persistently adherent 5 sec after ultrasound was turned off (retained fraction) were counted offline by an operator blinded to experimental conditions.

Figure 2:
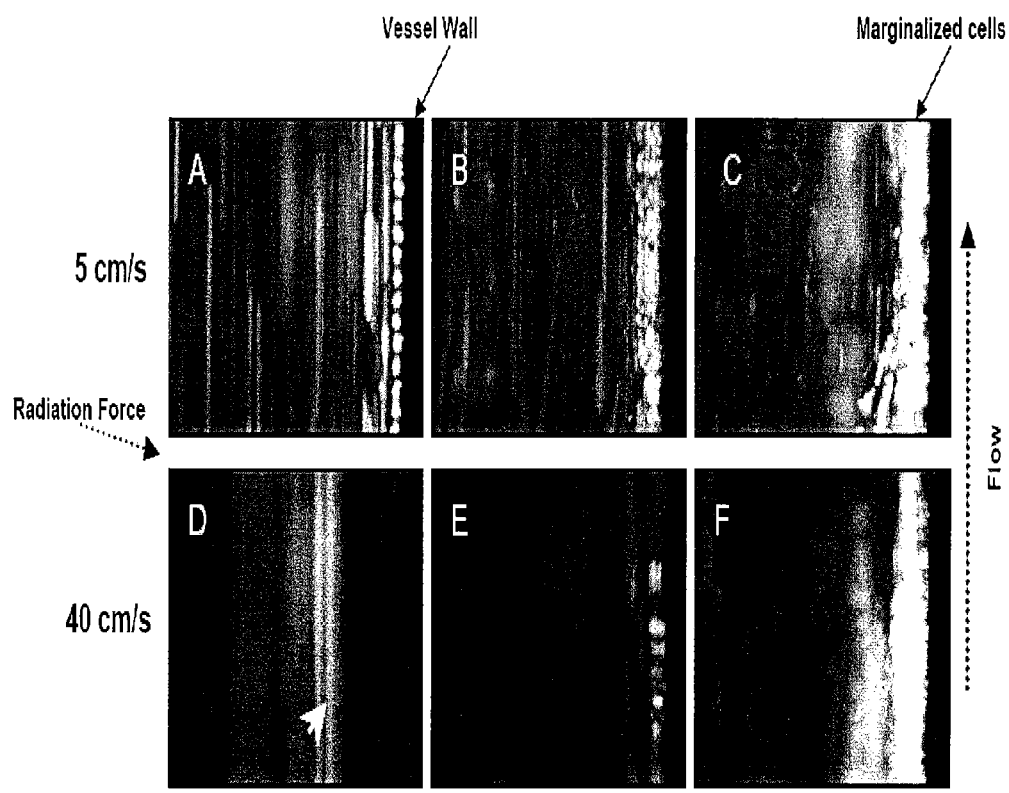
FIG. 2 presents exemplary data collected using the testing model in accordance with FIG. 1. Maximum intensity projections showing directed cell marginalization using radiation force under physiologic flow conditions. The HUVECS were labeled with a fluorescent dye (CMRA), then advanced through the silastic tube alone (A, D), after mixing with negatively charged bubbles (negative control, B, E) and after mixing with positively charged bubbles (C, F). The images are obtained by overlapping the frames of a 15 s videoclip, with radiation force being applied for 5 s. The border of the silastic tube is to the right in each frame. The flow velocity in the top row is 5 cm/s, and in the bottom row is 40 cm/s (approximating systolic and diastolic coronary flow velocities respectively). Note that under flow the cells have a tendency to stay away from the vessel wall border (white arrow, D).
Figure 3:
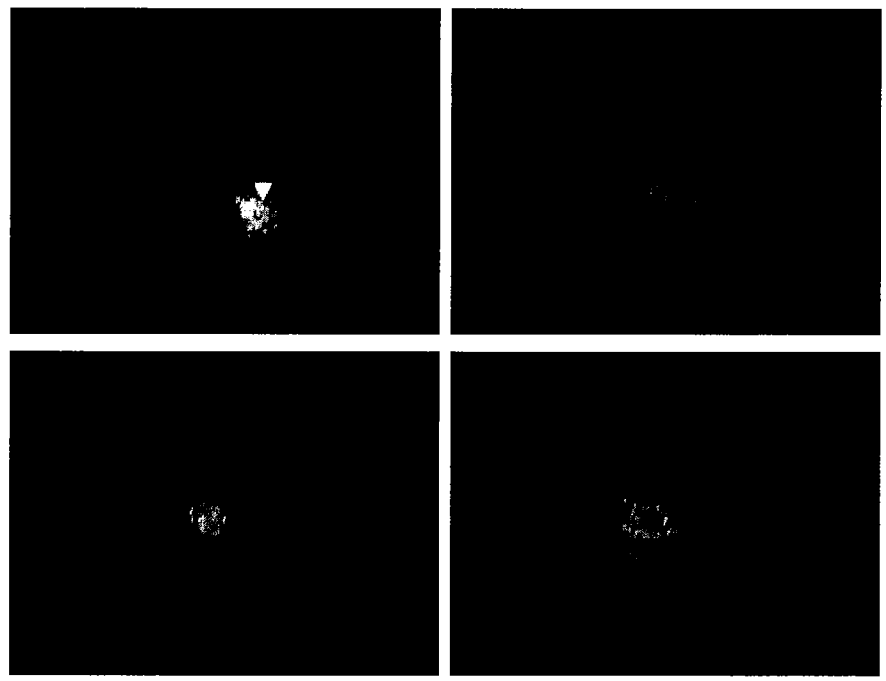
FIG. 3 presents exemplary data showing an electrostatic progenitor cell:microbubble association by demonstrating progenitor cell coated with cationic microbubbles. The fluorescent labeled HUVECs subsequent to positively charged microbubble attachment in accordance with the testing model of FIG. 1. Fluorescent imaging of the cells used in the experiments depicted in FIG. 2 was performed after mixing with the positively charged microbubbles. The HUVECs were labeled with CMRA (orange), and were mixed with cationic microbubbles labeled with fluorescein (green). Cell-bubble association is evident even in the red channel alone, due to the light scatter from the brightly fluorescent cells (white arrows).

The results presented herein demonstrate that electrostatic interactions between positively charged microbubble and predominantly negatively charged human umbilical vein endothelial cells (HUVECs) produce non-specific cell-microbubble associations. See, FIG. 2. Furthermore, it has been observed that these microbubbles are affected by radiation force under flow conditions. See, FIG. 3.

Figure 4:
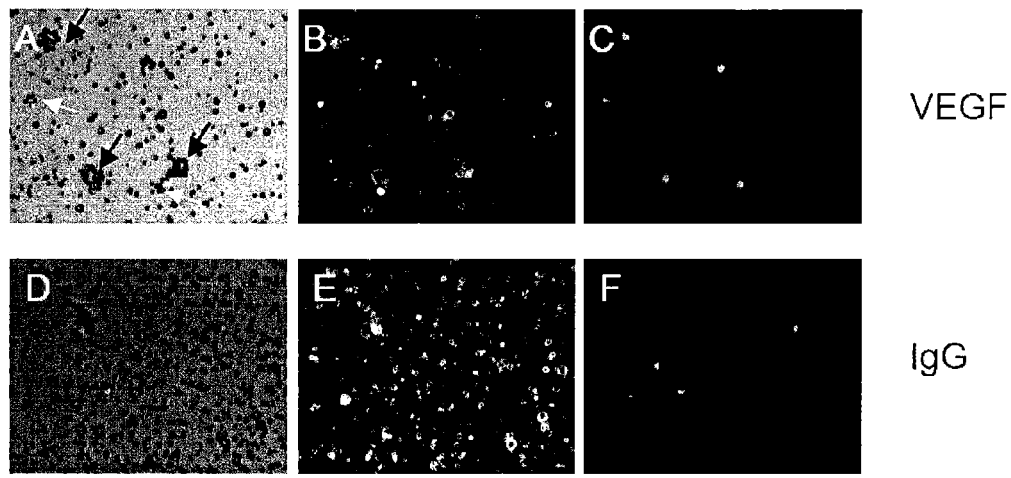
FIG. 4 presents exemplary data showing a ligand-specific progenitor cell:microbubble association by demonstrating VEGF-microbubbles associating with EPCs. Brightfield images are shown in panels A, D; rat bone marrow mononuclear cells (BM-MNCs) were labeled with CMRA (orange, panels C, F), while the microbubbles were loaded with fluorescein (green, panels B and E). Top row (A-C) shows BM-MNCs mixed with VEGF-microbubbles, while the bottom row shows the same cells mixed with IgG-microbubbles (negative control).

Freshly-prepared rat mononuclear bone marrow cells (BM-MNC) were used as a source of EPCs and studied in the testing model. See, FIG. 4. Vascular endothelial growth factor (VEGF) was used as a cell-specific ligand for EPC and the VEGF molecule was attached to the microbubble surface using a biotin-streptavidin bridge. Similar results were observed whether the microbubble was derived from a commercially available polymer bubble (Point Biomedical) or a lipid based bubble. Microbubble-EPC association is noted with the VEGF-microbubbles (FIG. 4A, black arrows), but as expected this heterogeneous cell population (i.e., BM-MNCs) contains cells not binding the VEGF-microbubbles (FIG. 4A, white arrows). No microbubble-EPC association was observed for the control IgG-microbubbles.

Figure 5:
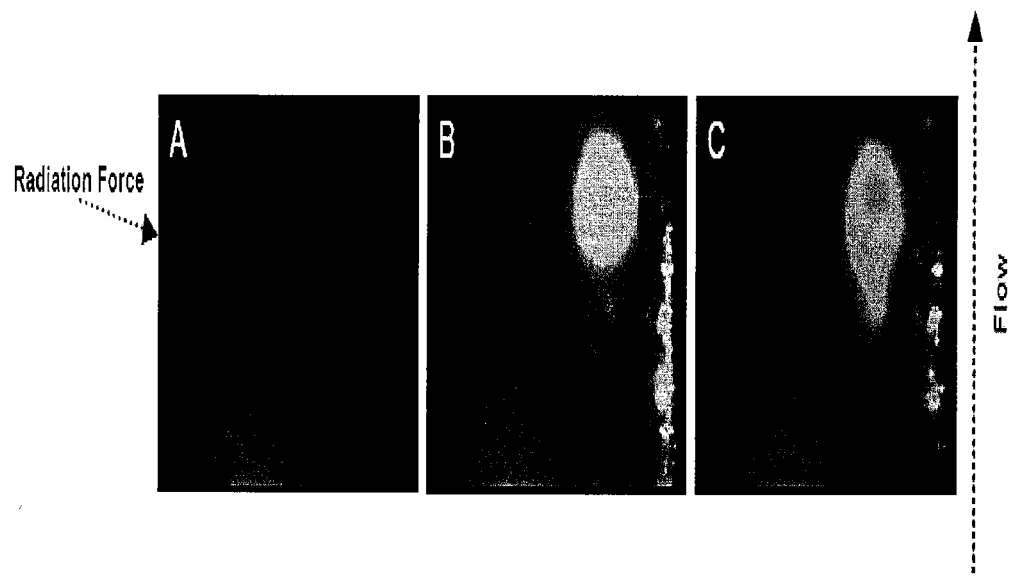
FIG. 5 presents exemplary data showing that EPC-microbubble complexes adhere to a vessel wall using radiation force under fluid flow conditions. EPC-microbubbles were produced by mixing BM-MNCs with VEGF-lipid microbubbles. The images represent time-average projections of 5 second intervals: Panel A: Absence of radiation force; Panel B: Presence of radiation force; Panel C: After radiation force is turned off.

Adherence of EPC-microbubble complexes to a "vessel wall" (comprising HUVECs attached to the silastic tubing) using acoustic radiation force under coronary artery flow conditions (5 cm/second) has also been demonstrated. See, FIG. 5. Specifically, exposure to 10 MHz US of acoustic radiation force demonstrated significant marginalization at shear stress levels comparable to coronary flow. In the absence of a acoustic radiation force no binding of an EPC-microbubble is observed (i.e., for example, no spontaneous EPC-microbubble adherence to the HUVECs). See, FIG. 4A. However, during and after exposure to acoustic radiation force, the EPC-microbubble complexes can be seen attached to the vessel wall. No marginalization was observed using HUVECs alone, while minimal marginalization was observed with HUVECs attached to negatively charged microbubble. These data document that a subset of the BM-MNCs adhere to the vessel wall (i.e., for example, a subset comprising endothelial progenitor cells (EPCs).

These data demonstrate that cells can be vectored in space specifically by association with "gas-filled lipid microbubbles" by using acoustic radiation force. Although it is not necessary to understand the mechanism of an invention, it is believed that these microbubbles are used as a "sail" for the attached cell, wherein ultrasound energy is used to direct the cell motion.

Overall, the number of microbubbles per cell that resulted in the highest number of MSCs adhering to the wall of the vessel phantom was approximately 7±1. A paradoxical observation indicated that at higher degrees of microbubble coating, cell adhesion decreased. Although it is not necessary to understand the mechanism of an invention, it is believed that this decrease in adhesion may be due to the fact that, when a threshold number of attached microbubbles is exceeded, the microbubbles themselves interfere with the contact needed between the MSC surface and the tube wall to establish adhesion. It should be recalled that there was no significant adhesion to the tube wall by MSCs mixed with negatively charged (i.e., for example, anionic) control microbubbles. Although it is not necessary to understand the mechanism of an invention, it is believed that when MSCs and anionic control microbubbles are mixed, no mb:MSC complexes are formed. This is an important finding, indicating that the above-described cell paving effect is specific for cell attachment and/or binding to cationic microbubbles (i.e., for example, positively charged), and not due to microbubbles transferring kinetic energy to the MSCs simply by colliding with them (i.e., for example, a "cue-ball" effect). Alternatively, it is believed that despite the fact that the cells were exposed to ultrasound for only a short time, the MSCs remained adherent to the tube wall even after the ultrasound force was removed. This was unexpected and unpredictable, given that the inner surface of the PVC tube used was not coated with any adherence-enhancing substrate; indeed, no MSC adhesion was observed in the in vitro experiments prior to the application of radiation force. One possible explanation may be that cell adhesiveness itself may be directly affected by ultrasound.

B. MSC-Microbubble Association: Flow Cytometry

The data presented herein assess the degree of association of cells (i.e., for example, MSCs) with cationic microbubbles using flow cytometry with respect to number of cells with attached bubbles, as well as average number of bubbles/cell. Such a method is capable of defining the number of bubbles/cell to achieve maximal kinetic energy applied to each cell in the acoustic field, and can quantify the cell-microbubble association. While microscopic evaluation of the cells is reliable, it is time consuming and may only reflect on a small proportion of cells. In vitro and in vivo data can show that microbubble presence on a cell surface alters the side-scatter (SSC) properties of a cell.

Although it is not necessary to understand the mechanism of an invention, it is believed that for a given acoustic waveform, there is an optimal number of microbubbles attached to each cell which results in maximum adhesion to the vessel wall. For example, a lower number of microbubbles per cell would be expect to result in less RF thereby resulting less cell movement. Clearly, higher microbubble numbers attached to a cell would ultimately interfere with the physical capacity of a cell to adhere to a target.

Associations between a strongly cationic lipid particle and a cell has been reported to result in cellular toxicity, in part due to the diffusion of the cation lipid into the cell membrane. Soenen et al., "Addressing the problem of cationic lipid-mediated toxicity: the magnetoliposome model" *Biomaterials* 30(22):3691-3701 (2009). However, preliminary data related to some embodiments of the present invention indicate cell toxicity associated with the cationic microbubbles is not occurring. The microbubbles contemplated herein comprise a strong polyethylene glycol (PEG) lipid backbone, rendering a stable microbubble attached to a cell surface.

The data presented herein is representative of either rat MSCs or human umbilical vein endothelial cells (HUVECs) in association with gas-filled microbubbles (i.e., for example, either cationic microbubbles or anionic microbubbles). Optimal cell:microbubble associations designed for RF-based delivery were examined by flow cytometry. Cell:microbubble complexes comprise multiple reflective surfaces that lead to a significant increase in the amount of orthogonal scattered light (side-scatter; SSC) as compared to a microbubble alone.

Flow cytometry data were performed that compares: i) forward scatter (FSC)/side scatter (SSC) profiles of MSCs alone; ii) MSCs mixed with cationic bubbles at a 1:40 and 1:400 cell:microbubble ratios; and iii) MSCs mixed with control non-cationic microbubbles (i.e., for example, anionic) at 1:400 ratio. MSCs were labeled with a fluorescent dye (i.e., for example, CMRA). The data shows the resultant fluorescently gated events in green.

The average electrostatic charge for the cationic microbubbles was +55.2 mV (average diameter 2.7 µm), while the control microbubbles had a charge of −18.6 mV (average diameter 2.3 µm). The rat MSCs had a surface charge of −23.6 mV. The addition of cationic microbubbles to a concentrated suspension of freshly trypsinized rat MSCs in PBS led to virtually instantaneous coating of the MSCs with bubbles. See, FIG. 1, Inset. In contrast, control (non-charged) microbubbles did not adhere to MSCs. Cell-microbubble association was analyzed by microscopy, allowing for quantification of the proportion of MSCs coated with bubbles (%), as well as the average number of bubbles/cell (n=6 different batches of MSC and microbubble).

For each of the in vitro flow experiments, samples of the CMRA-labeled mb-MSC complexes were also analyzed by flow cytometry. Rat MSC:microbubble complexes were also observed under DIC microscopy, and the proportion of cell with microbubbles (% cells positive), as well as the average number of microbubbles per cell were quantified (n=5 different experiments, with at least 20 cells analyzed in each group). The proportion of cells with increased side-scatter correlated well with the % cell positive as determined microscopically. See, FIG. 9A; $r^2=0.8$). Similarly, a strong linear correlation was found between the average number of microbubbles/cell and an average value of SSC (both parameters measured exclusively for the cells that have microbubbles on their surface. See, FIG. 9B; $r^2=0.81$). With an increasing ratio of the number of cationic bubbles added to the number of MSCs in suspension, the amount of MSC sidescatter (SSC) increased relative to MSCs alone. Compare, FIGS. 9B and 9C with FIG. 9A. This MSC sidescatter increase was not observed when using the slightly negatively charged control microbubbles. See, FIG. 9D. In fact, MSC: control microbubble SSC data was practically identical to MSC alone. Compare, FIG. 9A with FIG. 9D.

A linear correlation was observed between the percentage of cells with increased side-scatter, defined as based on the upper limit of control MSCs not exposed to bubbles, and the number of cells coated with bubbles as identified by microscopy ($p<0.001$, $r^2=0.81$). See, FIG. 9E. In addition, there was a linear correlation between the geometric mean SSC intensity of the MSCs with increased SSC (i.e., the MSCs coated with cationic microbubbles) and the average number of microbubbles per cell as quantified by microscopy ($p<0.001$, $r^2=0.81$). See, FIG. 9F. Thus, the side scatter properties of the mb-MSCs as determined by flow-cytometry can be used to quantify cell:microbubble interaction both in terms of the proportion of cells with microbubbles on their surface, as well as the average number of microbubbles per coated cell. The data show that SSC increased approximately 70.0% when using MSC:cationic microbubble complexes as compared to approximately 12% when measuring cationic microbubbles alone. SSC in MSC:cationic microbubbles was also greater than that seen in the MSC:anionic control bubbles, despite that 10× more bubbles were used in control experiments.

This data confirms that side scatter properties of MSC:microbubble complexes, as determined by flow-cytometry, can be used to quantify and compare cell:microbubble complex interactions. It is generally believed that cationic charges may be toxic to cells due to detrimental effects on cell membrane integrity. Consequently, other control experiments were performed to ensure MSC viability was not influenced by microbubble associations. For example, MSCs were suspended in calcium/magnesium free phosphate buffered saline (PBS) at room temperature and either mixed with cationic bubbles at a 1:40 or a 1:120 ratio. Both ratio mixtures were either left alone (negative control) or incubated with 10 mM $H_2O_2$ (positive control). Ethidium homodimer-1, a red-fluorescent nucleic acid stain, was used to detect cell viability in that only membranes of dead cells are permeable to this compound. After a two hour incubation with the dye, microscopic analysis determined a similar proportion of nuclear red fluorescence stained cells were observed in control (16.6%), MSC+cationic bubbles 1:40 and 1:120 (17.4% and 15.2% respectively) without $H_2O_2$ exposure. $H_2O_2$ exposure did increase the overall percentage of cell death but did not change the relative proportions between the groups. (avg 56.8%, n=2). Consequently, the effect of the association of microbubbles to MSCs on cell viability was tested. The data show that in the presence of microbubbles as contemplated herein, apoptosis was detected in 13.1±0.9% of the MSCs, higher than that in control conditions (MSCs alone, 7.7±0.6%, p<0.005), but less than that observed with $H_2O_2$ (28.1±2.7%, n=3, p<0.005) as a positive control.

The flow-cytometry derived parameters were then validated against microscopy data. Associations between MSCs and microbubbles were confirmed by differential interference contrast (DIC) microscopy. Specifically, it was found that 87.9±5.4% of MSCs had surface-attached cationic microbubbles, while 8.9±3.7% of MSCs had surface-attached anionic control microbubbles, even at a 10× higher ratio. High affinity between cationic microbubbles and MSCs were cell specific. For example, when using human umbilical vein endothelial cells (HUVECs), a 1:40 cell:cationic microbubble ratio resulted in 15.9±8.4% cells having surface attached microbubbles on their surface by microscopy (data not shown: n=4 experiments, with at least 30 cells randomly analyzed).

C. In Vitro RF-Driven Cell-Microbubble Complex Adherence

Figure 13:
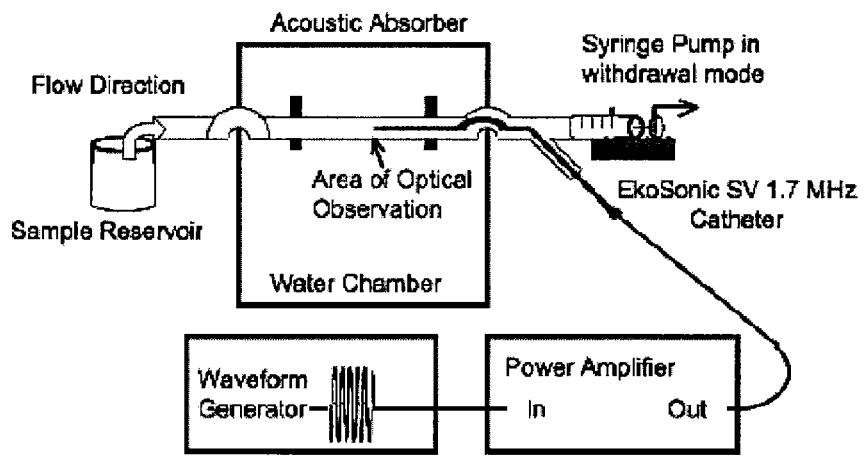
FIG. 13 presents a schematic of one embodiment of an in vitro experiment equipment setup. A cell:microbubble mixture is aspirated through a vessel phantom (silastic or polyvinylchloride tube; pink) using a precision syringe pump. A catheter (i.e., for example, EkoSonic SV; blue) is placed inside the vessel phantom using a Tuhoy connector. The region adjacent to the active element of the catheter is over an objective of an inverted fluorescent microscope (i.e., for example, Olympus IX81).

The data presented herein demonstrate an ability to drive cell-microbubble complexes to a vessel wall while under relevant physiological flow conditions. For example, an in vitro blood vessel model comprising a transparent polyvinyl chloride (PVC) tube was viewed with an upright fluorescence microscope (i.e., for example, an Olympus BX51). An external 0.75 inch 5 MHz transducer (i.e., for example, an Olympus NDT) was placed at a slight angle to the solution flow direction within a PVC tube, wherein ultrasound energy was focused in the same spot as the microscope optical focus. See, FIG. 13.

In these tests, MSCs were mixed with cationic microbubbles at ratios between 1:12-1:400, which resulted in 100% of MSCs carrying microbubbles on their surface. In contrast, mixing cells with anionic control microbubbles up to 1:400 showed less than a 5% association between the microbubbles and the MSCs. Solution flow rates within the PVC tube were selected to create a wall shear stress (WSS) of approximately between 0.4-0.5 Pa, comparable to an average WSS in human coronaries and accounts for the decreased viscosity of the PBS used in our system compared to blood. Doriot et al., "In-vivo measurements of wall shear stress in human coronary arteries" *Coron Artery Dis* 11:495-502 (2000).

Figure 10:
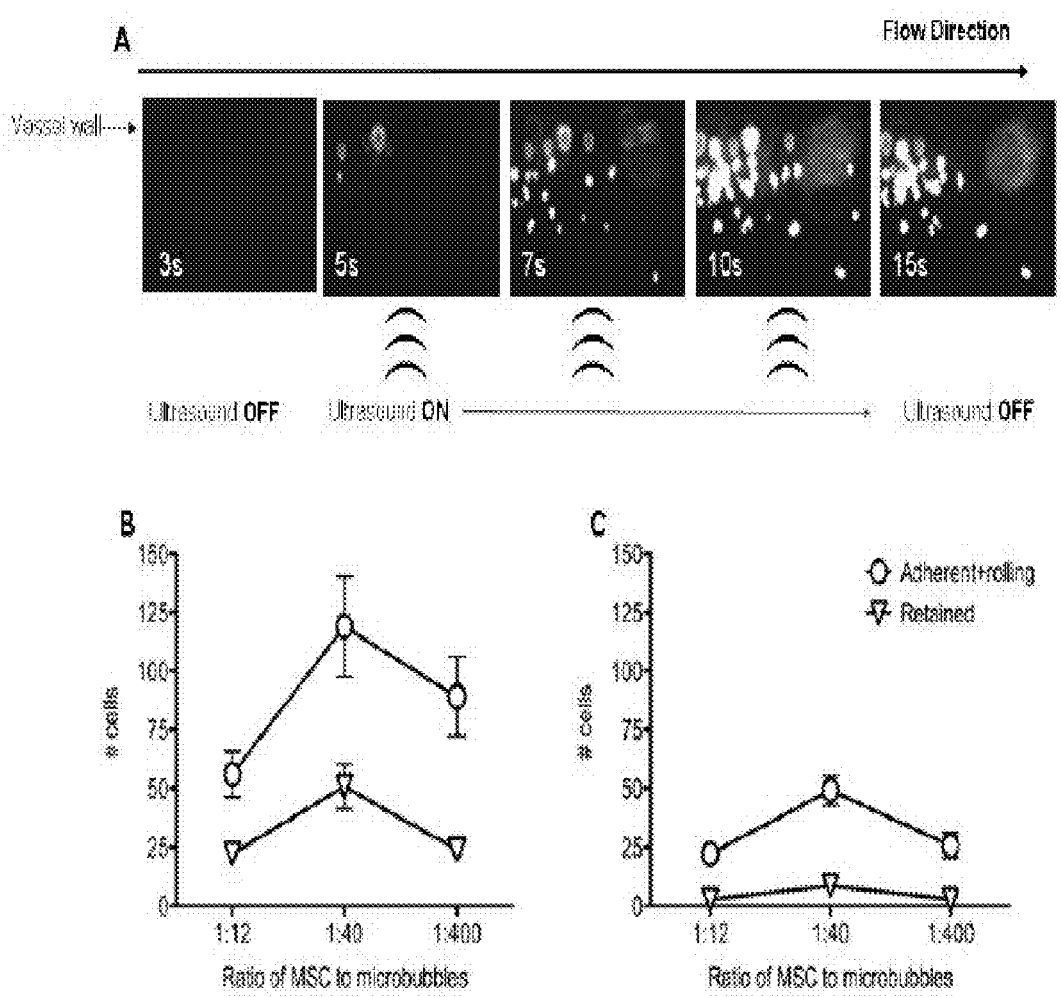
FIG. 10 presents exemplary data showing the feasibility of acoustic radiation force mediated cell delivery in vitro-results. A. Selected microscopic images of the vessel phantom depicting acoustic radiation force-induced displacement of mb-MSC complexes during 15 sec of flow (wall shear stress 0.53 Pa).). The wall of the vessel phantom away from the ultrasound source is at the top of the images. No cell adhesion is observed during the first 5 s without ultrasound (left frame). Application of ultrasound leads to immediate cell rolling and adhesion (middle 3 frames). Some MSCs remain adherent even after the ultrasound is turned off (right frame). The number of cells rolling and adhering (circles) and persistently attached (retained, triangles) under low (B) and high flow conditions (C) was quantified at different MSC to microbubble mixture ratios.

This experimental set-up provided a time-lapse imaging of the displacement of mb-MSCs using acoustic radiation force under flow conditions in the vessel phantom (i.e., for example, at a wall shear stress (WSS) ~0.53 Pa). This in vitro experimental design determined an optimal cell:microbubble association by testing increasing MSC:microbubble ratios. Specifically, the data was compared for the # of cells rolling, the # of cells adhering, and the # of cells that remained adherent after the ultrasound was turned off (n=6). The data show that an optimal MSC:microbubble ratio is approximately 1:40, which based on FACS and microscopy data and corresponds, on average, to approximately 71 microbubbles per MSC. See, FIG. 10. Further, the data demonstrates that microbubble:cell ratios in excess of 40:1 may have a detrimental effect on RF-targeting efficiency. Although it is not necessary to understand the mechanism of an invention, it is believed that excess microbubble attachment to a single cell can act as an "airbag", thereby preventing the adherence of the cells to the vessel wall (i.e., for example, by steric hindrance).

There was virtually no cell marginalization in the absence of acoustic energy during the first 5 s of exposure. Selected microscopic images of a vessel phantom depicting the displacement of mb-MSC complexes due to ultrasound-generated radiation force during a 15 s in vitro run at a wall shear stress of approximately 0.53 Pa. The wall of the vessel phantom away from the ultrasound source is at the top of the images. MSCs appear as white circular targets under fluorescent microscopy, with fluorescence coming from several focal planes resulting in apparent large differences in MSC size. No cell adhesion is observed during the first 5 s (left frame), while application of ultrasound leads to immediate cell rolling and adhesion (middle 3 frames), with a number of MSCs remaining adherent even after the ultrasound is turned off (right frame). See, FIG. 10A. Low and high flow conditions mimicking systolic coronary shear stress quantified at different MSC to microbubble mixture ratios. Circles: The number of cells rolling and adhering. Triangles: The number of retained cells (i.e., persistently attached). FIG. 10B: Low and high flow conditions mimicking diastolic coronary shear stress quantified at different MSC to microbubble mixture ratios. Circles: The number of cells rolling and adhering. Triangles: The number of retained cells (i.e., persistently attached). FIG. 10C.

The number of adherent MSCs, either for the duration of ultrasound exposure, or temporarily as rolling cells, as well as the number of cells retained on the tube surface after the ultrasound was turned off was quantified under fluid flow corresponding to low and high shear stress (i.e., for example, WSS 0.53 Pa vs 4.2 Pa) believed equivalent to coronary systole or coronary diastole. See, FIGS. 10B and 10C, respectively. For low flow conditions (e.g., WSS 0.53 Pa), there was a significant difference in the number of adherent and retained MSCs as a function of cell to microbubble ratio (Kurskall Wallis p<0.05). On post hoc testing, there was a significant increase in the number of retained MSCs with increasing cell:microbubble ratio from 1:12 to 1:40 (p<0.05). However, as this ratio was increased further to 1:400, the number of retained cells decreased relative to 1:40 (<0.05 for retained cells). Thus, the acoustic power effect in increasing mb-MSC adhesion to the vessel phantom was maximal when the ratio of MSC to microbubbles was 1:40, which based on the microscopy data presented above corresponds to 88±5% of MSCs being coated by microbubbles and an average of 7±1 microbubble/cell (n=6). Further, increasing the wall shear stress to values corresponding to diastolic coronary flow led to a significant decrease in the number of retained cells. See, FIG. 10C; WSS ~4.2 Pa, p<0.001 for each mixing ratio.

D. In Vivo RF-Driven Cell:Microbubble Complex Adherence

The data presented herein demonstrate that RF is effective in moving cells despite potential interference from in vivo circulating blood cells. Using anesthetized, intubated adult New Zealand rabbits, an angioplasty balloon was inserted retrogradely through a sheath placed in the right iliac artery thereby injuring and/or de-endothelializing the thoracic aorta. Upstream vascular access was established by passing a PE50 cannula to the top of the aortic arch via left carotid artery insertion. An Ekos small vessel catheter modified for this application (infra) was then advanced retrogradely via the femoral artery to the balloon-denuded area under fluoroscopic guidance.

In some embodiments, in vivo cell:microbubble complex delivery was practiced in a rabbit model of aortic endothelial injury. Although it is not necessary to understand the mechanism of an invention, it is believed that rabbit aortas comprise both the size of the vessel as well as the occurrence of endothelial damage are pertinent to human coronary atherosclerotic disease. For example, a denuded surface of the balloon-injured rabbit aorta represents an appropriate substrate for MSC adhesion. Although only approximately 1% of the injected mb-MSCs were identified in vivo 20 min after restoration of aortic flow, this nevertheless represented up to 150 fold enrichment over control conditions in which no ultrasound was applied. Further, 24 hours after the treatment, there was evidence of engraftment and spreading out of the MSCs on the aortic wall, indicating viability of the adherent cells.

It has been reported that endoluminal seeding of EPCs loaded with supermagnetic iron oxide nanoparticles using an external magnetic field to only 5.4 fold over control. Kyrtatos et al., "Magnetic tagging increases delivery of circulating progenitors in vascular injury" *JACC Cardiovasc Interv.* 2:794-802 (2009). Similarly, iron-loaded EPCs were found to adhere to magnetized stents, with a similar 6 fold enrichment on average over controls. Pislaru et al., "Magnetically targeted endothelial cell localization in stented vessels" *J Am Coll Cardiol.* 48:1839-1845 (2006). Thus, acoustic methods described herein offer a significant increase in the magnitude of achievable endoluminal paving with cells than heretofore reported using other methods.

Figure 12:
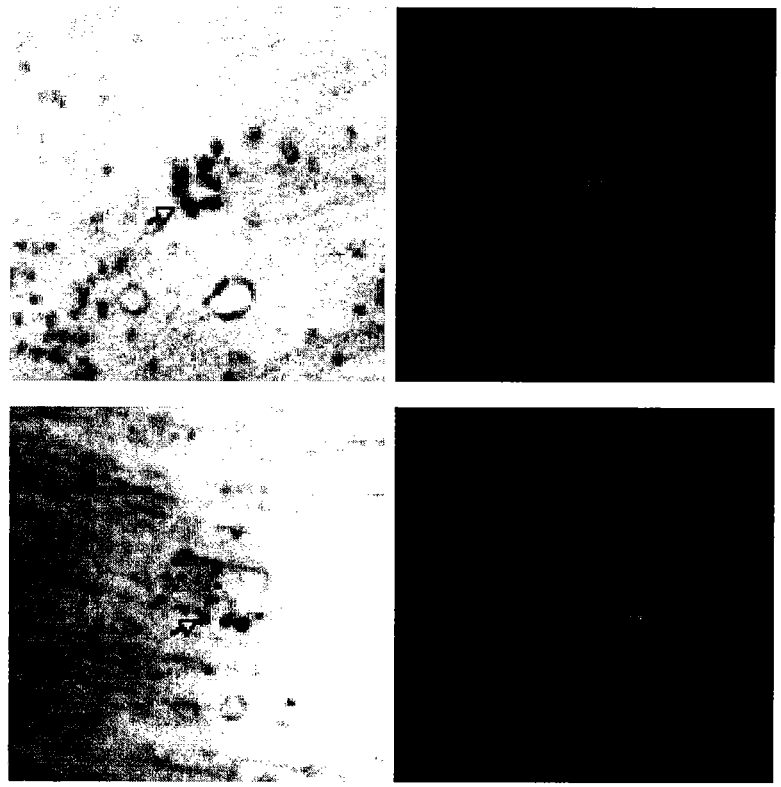
FIG. 12 presents exemplary in vivo data showing cell: microbubble complex adherence to blood vessel endothelia. Microbubble labeled MSCs were identified on the aortic wall of rabbits after in vivo RF mediated cellular paving (left column, arrows pointing at bubbles). These were confirmed as being the injected CMRA labeled MSCs by their red fluorescence

Rabbit MSCs were labeled with a fluorescent dye (i.e., for example, CMRA, Molecular Probes), mixed with cationic microbubbles at 1:100 cell:microbubble ratio, and slowly injected through the carotid cannula. This injection was performed upstream of the Ekos catheter while operating with a custom wave form/cycle length at 1.7 MHz with an 8% duty cycle. After twenty minutes the rabbit was euthanized, and the thoracic aorta was perfused with saline to remove the blood, followed by 10% formalin for in-situ fixation. The vessel was then dissected, cut open longitudinally and examined en-face using an inverted microscope. Adherent MSCs to the vessel surface were identified based on detection of red fluorescence signals. See, FIG. 12, right panels. These fluorescent spots were co-located with the identification of microbubbles (arrows) on the large majority of the adherent cells as seen using DIC microscopy. See, FIG. 12, left panels. Thus, these data show that RF may direct cell-based therapies to preselected in vivo tissues, resulting in a stable adhesion of the cells to the tissue.

Ultrasound-mediated displacement of mb-MSC complexes were also evaluated in an in vivo setting. In this embodiment, mb-MSC progenitor cell complexes were delivered to a vascular segment following balloon-injury of the rabbit aorta. Following balloon denudation, of the central segment of a thoracic/abdominal aorta, an inflated occlusion balloon is shown located above the damaged area. Microbubble:cell complexes (mb:MSC) were injected anterogradely into the aorta through the central lumen of this balloon. Ultrasound was delivered exclusively to the more distal descending aorta as exemplified by an Ekosonic SV catheter advanced retrogradely through the femoral artery. See, FIG. 15A. Cationic microbubbles had a similar affinity for rabbit MSCs as for the rat MSCs by FACS analysis (data not shown). Histological examination of the aortic segments 20 min following the treatment revealed minimal cell adhesion in the control segments that were exposed only to mb-MSCs, without radiation force. Specifically, a low magnification en face microscopic imaging of the endoluminal side of an aortic segment 20 min after delivery of mb-MSCs, showing only occasional single fluorescent MSC adhesion in the control proximal segment not exposed to ultrasound (Control, Inset: B1), whereas numerous MSCs (arrowheads) adhered to the ultrasound-treated areas (Ultrasound, Inset: B2). Scale bar 200 μm. Although it is not necessary to understand the mechanism of an invention, it is believed that the distribution of adherent MSCs was not uniform, possibly due to an asymmetric positioning of the catheter relative to the vessel wall. Microscopic examination revealed that the microbubbles were no longer present on the MSCs adherent to the endoluminal surface of the aorta (not shown). There was more than 100 fold and 150 fold increase in MSCs adhesion to aortic segments treated with low (p<0.05) and high acoustic power ($p_< 0.01$), respectively, when compared to the control lesions. Quantification of the density of MSC retained for control conditions (black circles), low (0.5 MPa, blue squares) and high (1 MPa, red triangles) acoustic radiation force. *p<0.05, **p<0.01 vs control, n=6-7. See, FIG. 15C.

Figure 16:
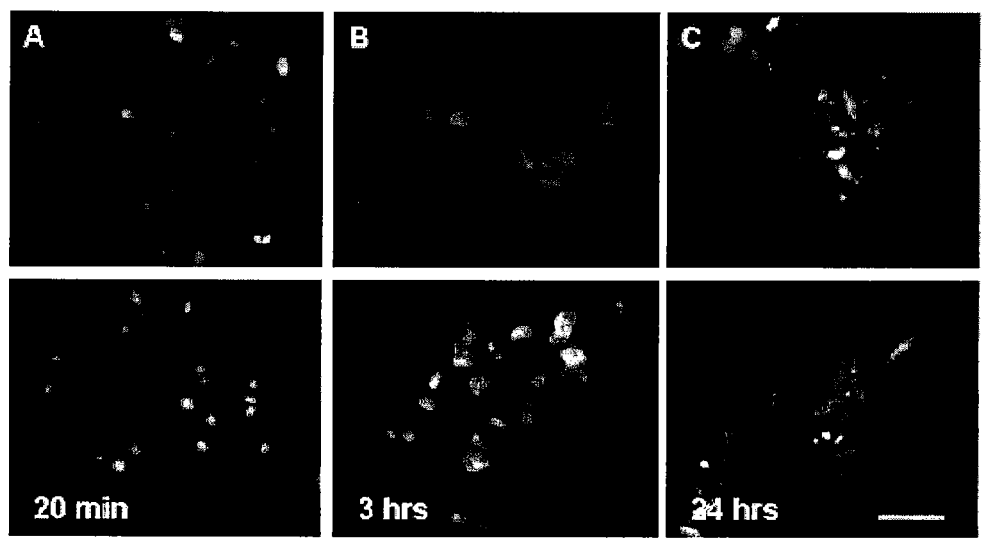
FIG. 16 presents exemplary data showing that delivered progenitor cells survive on a denuded arterial surface. The MSCs adherent to the aortic endoluminal surface following ultrasound mediated delivery survive and undergo morphological changes, between immediate (2 examples in A) 3 hrs (B), and 24 hrs (C) post delivery Scale bar 100 mm.

The data presented herein shows microscopic images of treated aortic segments demonstrating longer term fate of MSCs after ultrasound-mediated delivery. MSCs adherent to the endoluminal surface of the aorta following low RF or high RF ultrasound mediated delivery survive and undergo morphological changes. At 24 hrs after ultrasound treatment, surviving MSCs were clearly identified on the endoluminal surface of the treatment area. See, FIG. 16. The engrafted cell morphology changed gradually after delivery: i) round at 20 min after delivery (See, FIG. 16A); ii) progressively flattened at 3 hrs after delivery (See, FIG. 16B); and iii) a spread out morphological appearance (similar to cell culture) at approximately 24 hrs after delivery with a MSC morphology similar to that observed in cell culture (See, FIG. 16C). Scale bar 100 μm.

Figure 17:
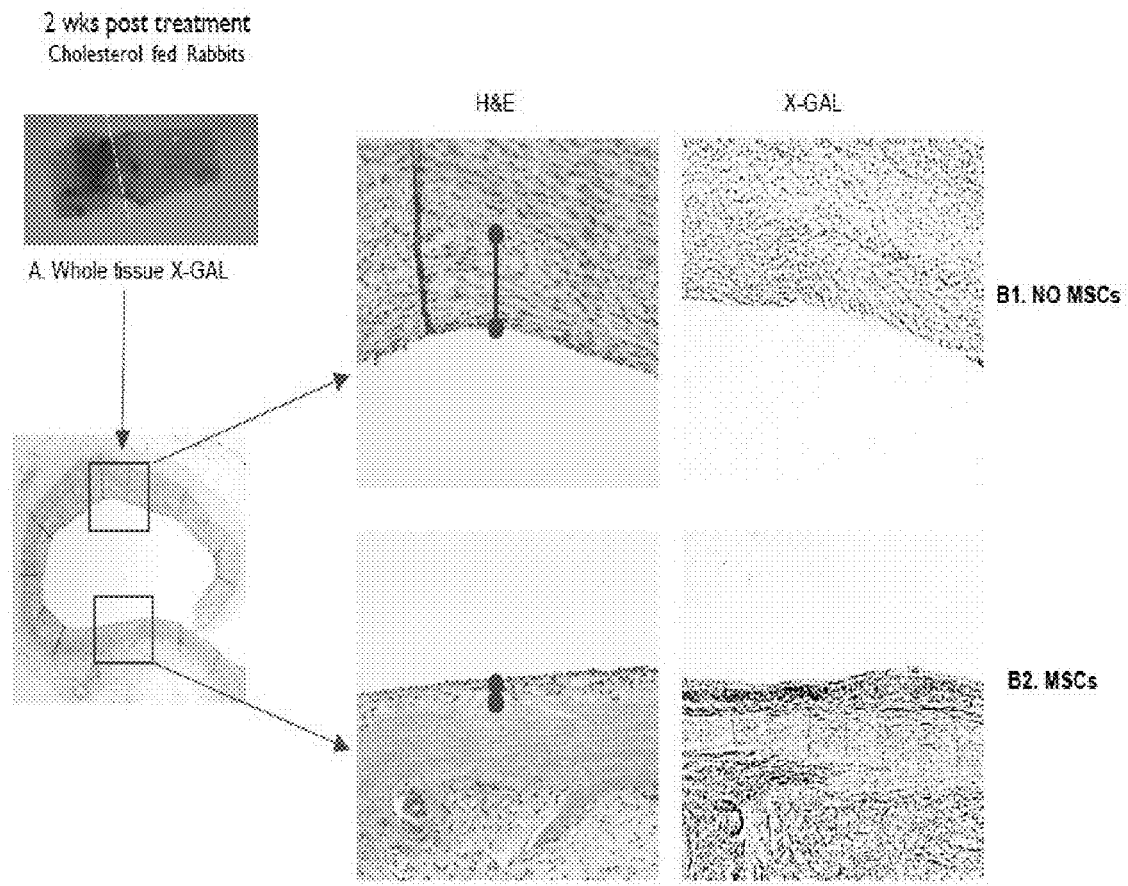
FIG. 17 presents exemplary data showing long-term survival of the progenitor cells delivered using acoustic radiation force. MSCs were delivered using an acoustic radiation force that resulted in an accelerated vascular endothelialization. MSC genetically labeled with lacZ were electrostatically coated with cationic microbubbles. A balloon injury was created in hypercholesterolemic rabbits in the intrarenal aorta, followed by acoustic radiation force mediated delivery of the mb:MSCs to the injured area. A. At 2 weeks, there was significant coverage of the treated segment by lacZ labeled MSCs (the entire arterial segment is shown after X-gal staining, rendering the labeled MSCs blue). B. Histological analysis of the treated area indicates that the regions covered by MSCs (B1) have a decreased neointimal formation compared to the areas not seeded by cells (B2).

Data presented herein show a long-term survival of progenitor cells delivered using acoustic radiation force. For example, MSCs were delivered using an acoustic radiation force that resulted in an accelerated vascular endothelialization. These MSCs were genetically labeled with lacZ and electrostatically coated with cationic microbubbles. In these experiments, a balloon injury was created in hypercholesterolemic rabbits in the intrarenal aorta, followed by acoustic radiation force mediated delivery of the mb:MSCs to the injured area. At 2 weeks after treatment, there was significant coverage of the injured area by lacZ labeled MSCs (i.e., for example, the entire arterial segment is shown after X-gal staining, rendering the labeled MSCs blue). See, FIG. 17A. Histological analysis of the treated area indicates that the regions covered by MSCs have a decreased neointimal formation as compared to the areas not seeded by cells. See, FIGS. 17B1 and 17B2, respectively.

III. Optimization of Cell:Microbubble Complex Adherence

In some embodiments, the present invention contemplates optimal parameter combinations capable of providing a maximal in vivo delivery and adherence of cell:microbubble complexes to a preselected target tissue. In one embodiment, an optimized parameter comprises a cell:microbubble ratio that yields a maximal acoustic radiation force. Although it is not necessary to understand the mechanism of an invention, it is believed that there is an optimal number of microbubbles per cell at which marginalization and adherence of cells to the vessel wall is maximal. Based on acoustic physical principles, a lesser number of microbubbles per cell may result in less radiation force applied to each cell, resulting in reduced movement of the cells towards the vessel wall. However, while increasing the number of bubbles attached per cell will augment the achievable acoustic radiation force, data suggest that there is a maximum microbubble per cell value, beyond which, more microbubbles per cell can paradoxically lead to less attachment to the vessel wall; i.e. an excessive number of microbubbles per cell can lead to an "airbag" effect, thereby physically preventing an interaction between the cell surface and the vascular wall, presumable by steric interference. Such a situation would thus impair cell adherence to a target.

In one embodiment, an optimized parameter comprises ultrasound transmission frequencies that most effectively drive a cell:microbubble complex. In one embodiment, an optimized parameter comprises an ultrasound acoustic pressure (power) that elicits the most effective microbubble oscillations. Although it is not necessary to understand the mechanism of an invention, it is believed that the transmission frequency and acoustic pressure are selected to maximize the acoustic radiation force generated by the interaction of microbubbles with the ultrasound. In one embodiment, an optimized parameter maximizes movement of acoustic force driven cell-microbubble complexes in flowing blood.

In one embodiment, the present invention contemplates a method for determining an optimal cell:microbubble delivery in an ex vivo porcine coronary artery. In one embodiment, the method provides acoustic RF using an intravascular catheter thereby enhancing target cell adhesion to the surface of a denuded coronary artery in the presence of blood under physiologic wall shear rate.

Although it is not necessary to understand the mechanism of an invention, it is believed that acoustic radiation force-induced translational motion of a cell:microbubble complex in a viscous fluid (i.e., for example, blood) may occur. Theoretically, this induced translation may interfere with using RF to drive MSCs to a preselected tissue target resulting in cell adhesion. To overcome such a translation interference the use of sufficient acoustic energy to cause a large portion of the cell/bubble complex to transit to the vessel wall should be considered.

Depending on the blood flow velocity, this transit time can be on the order of 1 ms. As a terminal velocity of the cell:microbubble complex in response to the acoustical force is expected, an acoustic pulse train optimization results in minimal acoustic energy balanced with a maximal translational motion of a cell:microbubble complex. Dynamic behavior of microbubbles in ultrasound fields has been reported as theoretical models. For example, some believe that radiation force on the microbubble can be derived from microbubble dynamics. It has been shown that the RF required for translation is heavily influenced by the size of the bubble and the frequency of the ultrasound wave. For a microbubble of a particular size, the RF is maximal near its resonance frequency, wherein the RF is nearly proportional to the geometrical cross-sectional area of the microbubble. At the same time, excessive acoustic power can lead to bubble destruction and thermal injury. While these theoretical considerations are useful for future designs of ultrasound delivery systems, systematic empirical testing will need to be performed to determine the overall ability of the delivery scheme to spatially manipulate cells under physiologic flow conditions.

Although it is not necessary to understand the mechanism of an invention, it is believed that an RF effect in marginalizing the MSCs may be reduced in the presence of blood as compared to equivalent exposure parameters used when collecting the PBS in vitro data (supra). Alternatively, longer exposure times to the RF in a targeted segment, or modulating the RF signal may successfully maximize cell:microbubble complex marginalization. In addition, circulating blood cells (i.e., for example, leukocytes or platelets) may adhere to cells via bubble-mediated interactions. Florescence microscopy may be used to identify multicellular agglomerates forming around a fluorescently label MSC.

IV. In Vivo Delivery Using Ultrasound Based Radiation Force

In one embodiment, the present invention contemplates a method for delivering cells to vascular segments using acoustic RF in vivo. In one embodiment, the acoustic RF drives the cells to injured vascular endothelium in vivo, such that the cells attach to the endothelium. In one embodiment, the cell delivery to the injured endothelium enhances long term endothelial repair. In one embodiment, the injured endothelium results from coronary stenting. In one embodiment, the cells comprise any type of cells including, but not limited to progenitor cells (i.e., for example, EPCs or CECs).

The data presented herein is a first description of targeted delivery of microbubble-coated cells using acoustic radiation force. The method is based upon a previously reported capacity to impart kinetic energy to gas-filled microbubbles. Dayton et al., "Acoustic radiation force in vivo: a mechanism to assist targeting of microbubbles" *Ultrasound Med Biol.* 25:1195-1201 (1999); and Dayton et al., "The magnitude of radiation force on ultrasound contrast agents" *J Acoust Soc Am.* 112:2183-2192 (2002). Acoustic microbubble delivery has been proposed to be useful in modulating microbubble adhesion to endothelial epitopes for molecular imaging, or to deliver a cytotoxic drug to tumor cells Zhao et al., "Radiation-force assisted targeting facilitates ultrasonic molecular imaging" *Mol Imaging.* 3:135-148 (2004); Borden et al., "Ultrasound radiation force modulates ligand availability on targeted contrast agents" *Mol Imaging.* 5:139-147 (2006); and Dayton et al., "Application of ultrasound to selectively localize nanodroplets for targeted imaging and therapy" Mol Imaging. 5:160-174 (2006), respectively. Although it is not necessary to understand the mechanism of an invention, it is believed that radiation force on a given microbubble is maximal when the incident ultrasound is at the natural resonance frequency of the microbubble, which in turn is a function of the microbubble resting diameter and shell composition.

For the lipid-shelled microbubbles as described herein, the average resonance frequency is close to 2.2 MHz. The FDA-approved ultrasound catheter used in this study (Ekosonic S V, 1.7 MHz), has been primarily employed to facilitate clot dissolution in patients with stroke and deep vein thrombosis, and has been demonstrated to have minimal detrimental biological effects even when used for prolonged periods of time. Soltani et al., "Absence of biological damage from prolonged exposure to intravascular ultrasound: a swine model" *Ultrasonics* 46:60-67 (2007). In some embodiments, an ultrasound pulse sequence was utilized that is different than that required for sonothrombolysis: for example, a long duty cycle (i.e., for example 20%) may be practiced while maintaining a short pulse length to minimize bubble destruction while achieving maximal radiation force.

While the present invention can successfully deliver any cell type, the MSC was chosen as the representative cell type for illustration because:
  i) MSCs have angiogenic and anti-inflammatory properties that make them attractive for vascular repair immediately following injury. Schinköthe et al., "In vitro secreting profile of human mesenchymal stem cells" *Stem Cells Dev.* 17(1):199-206 (2008); Kinnaird et al., "Bone-marrow-derived cells for enhancing collateral development: mechanisms, animal data, and initial clinical experiences" *Circ Res.* 95(4):354-363 (2004); Wu et al., "Effect of paclitaxel and mesenchymal stem cells seeding on ex vivo vascular endothelial repair and smooth muscle cells growth" *J Cardiovasc Pharmacol.* 46(6): 779-786 (2005); Yue et al, "Mesenchymal stem cells differentiate into an endothelial phenotype, reduce neointimal formation, and enhance endothelial function in a rat vein grafting model" *Stem Cells Dev.* 17(4):785-793 (2008); Forte et al., "Mesenchymal stem cells effectively reduce surgically induced stenosis in rat carotids" *J Cell Physiol* 217(3):789-799 (2008); and Wang et al., "Late outgrowth endothelial cells derived from Wharton jelly in human umbilical cord reduce neointimal formation after vascular injury: involvement of pigment epithelium-derived factor" *Arterioscler Thromb Vasc Biol.* 29(6):816-822 (2009).
  ii) MSCs have been shown to support endothelial cells growth. Sorrell et al., "Influence of Adult Mesenchymal Stem Cells on In Vitro Vascular Formation" *Tissue Eng Part A. Jan.* 14 (2009); and Potapova et al., "Mesenchymal stem cells support migration, extracellular matrix invasion, proliferation, and survival of endothelial cells in vitro" *Stem Cells* 25(7):1761-1768 (2007).
  iii) MSCs can be readily isolated, expanded, and characterized. Pittenger et al., "Multilineage potential of adult human mesenchymal stem cells" *Science* 284(5411): 143-147 (1999).
  iv) MSCs interact strongly with cationic lipid microbubbles by an order of magnitude higher compared to HUVECs (data not shown).
  v) MSCs are highly adhesive to exposed collagen and fibronectin. Wang et al, "Late-outgrowth endothelial cells attenuate intimal hyperplasia contributed by mesenchymal stem cells after vascular injury" *Arterioscler Thromb Vasc Biol* 28(1):54-60 (2008).

While the present invention can successfully treat any animal species. The data presented herein illustrates that embodiments using either rat or rabbit species may be successfully practiced. However, in other embodiments, the present invention contemplates swine species are preferable as a representative test animal for demonstration feasibility applicable to humans because:
  i) Swine coronary arteries are approximately of the same size as human arteries.
  ii) Swine coronary stenting has been reported, with standard assays for assessing the delayed healing of the vessel wall. Schwartz et al., "Drug-eluting stents in preclinical studies; updated consensus recommendations for preclinical evaluation" *Circulation Cardiovasc Interv* 1:143-153 (2008).
  iii) Cardiac percutaneous interventions in pigs is a reliable model of vascular injury. Toma et al., "Positive effect of darbepoetin on peri-infarction remodeling in a porcine model of myocardial ischemia-reperfusion" *J Mol Cell Cardiol.* 43(2):130-136 (2007).

A. In Vivo Delivery and Retention of MSCs

The data presented herein demonstrates that acoustic RF applied to microbubble-labeled cells using an intravascular catheter is superior to cell injection alone in promoting acute adhesion of arterially delivered MSCs to a denuded coronary arterial surface. These experiments were performed using porcine MSCs grown to confluence and labeled with the cytoplasmic dye CMRA prior to administration. The cells are tagged with microbubbles synthesized from optimal formulations and at cell:bubble ratios yielding the greatest adhesion in the in vitro studies (supra).

Based upon in vitro data, in the presence of low shear stress, up to 30% of MSC:microbubble complexes can be attached to a wall opposite to an RF source. See, FIG. 10. In the experiments described in accordance with Example III, cell adhesion (i.e., for example, the number of MSCs per surface area as measured using microscopy) will be compared between an ultrasound treated segment (LAD) vs. a segment not receiving ultrasound (LCX) using paired t-testing (two tailed). Assuming that the cell delivery process is at least 10% effective, and delivery of approximately 1 million cells for a 10 mm lesion would be expected in a coronary with a diameter of approximately 3 mm, thereby leading to about 1000 cells/mm$^2$ Although it is not necessary to understand the mechanism of an invention, it is believed that 1000 cells/mm$^2$ may be sufficient to provide coverage of an injured segment to support self-generating re-endothelialization.

In one embodiment, the present invention contemplates delivering cells to a target tissue efficiently by acoustical RF in the presence of in vivo blood and coronary flow conditions. The in vitro data presented herein, emulate coronary wall shear rates and test adhesion in the presence of blood cells. Consequently, an optimization of the present cell:microbubble complex delivery method with an RF catheter has been performed in a milieu that approximates the in vivo setting. In one embodiment, the present method may be further improved by utilizing a saline flush, thereby temporarily replacing the blood during RF application. Alternatively, occluding coronary flow during RF application may also improve the efficiency of cell delivery to the endothelial wall.

In one embodiment, cell delivery to a target tissue may be improved by modulating the ultrasound signal. For example, pulse configurations may be modified and/or reconfigured within an ultrasound beam from any transducer. In one embodiment, a endovascular catheter-based ultrasound system wherein a center frequency of the ultrasound element on the catheter is approximately 1.7 MHz, corresponds to resonance frequencies of a large portion of microbubble populations contemplated herein. In one embodiment, an acoustic pressure is approximately 1 MPa, wherein a low mechanical index prevents bubble destruction. In one embodiment, a catheter design comprises an ultrasound source delivering various wave trains including, but not limited to, narrow-band tone bursts, chirp excitation, various burst durations, or pulse repetition frequencies.

Although it is not necessary to understand the mechanism of an invention, it is believed that since the microbubble population is heterogeneous in size, a wider frequency band may maximize the overall RF effect by exciting bubbles closer to their resonating frequency. Hu et al., "Chirp excitation technique to enhance microbubble displacement induced by ultrasound radiation force" *J. Acoust. Soc. Am.* 125(3): 1410-1415 (2009).

B. Coronary Re-Endothelialization

In one embodiment, the present invention contemplates a method comprising delivering targeted MSCs using acoustic RF following stenting leading accelerated endothelialization and decreased inflammation of an injured tissue.

The data presented herein utilizes domestic pigs for chronic survival studies of intracoronary stenting. Coronary stenting in pigs is an established, standardized translational model for interventional cardiology for the study of vascular response to coronary stents. Suzuki et al., "The Pre-Clinical Animal Model in the Translational Research of Interventional Cardiology" *Am. Coll. Cardiol. Intv.* 2:373-383 (2009); and Schwartz et al., "Drug-eluting stents in preclinical studies; updated consensus recommendations for preclinical evaluation" *Circulation Cardiovasc Intery* 1:143-153 (2008). Although the vascular wall injury in healthy pig coronaries differs from what is seen when treating atherosclerotic plaques, the dramatic reduction in restenosis with DES in this model has translated into practice well, while delayed endothelialization and active inflammation similar to that seen in humans have been observed. Pendyala et al., "Endothelium-Dependent Vasomotor Dysfunction in Pig Coronary Arteries With Paclitaxel-Eluting Stents Is Associated With Inflammation and Oxidative Stress" *J. Am. Coll. Cardiol. Intv.* 2:253-262 (2009).

Quantitative coronary angiography may be performed to measure the degree of stenosis (expressed as % of luminal diameter) at endoluminally paved and control stented sites. In one embodiment, the present invention contemplates achieving a near complete coverage of the injured segment with endothelium by 2 weeks, with a significant difference relative to the control lesions. Associated with this re-endothelialization is a lesser degree of inflammatory infiltration and necrosis in the subintimal space in the treated segments. The 2-week evaluation was chosen based on existing data wherein there is maximum differentiation between the treated and MSC-paved stents. Longer follow-ups (i.e., for example 1-2 months) can lead to a reduction in the potential to detect a difference due to the gradual endothelial recovery in the control lesions as well. Based on existing data, an experimental design using 8 animals results in a 90% power to detect a 30% difference in the degree of endothelialization above the stent struts. Joner et al., "Endothelial cell recovery between comparator polymer-based drug-eluting stents" *J Am Coll Cardiol.* 52(5):333-342 (2008).

It should be noted that a dose of MSCs may be varied to optimize the almost complete cellular coverage (i.e., for example, cellular paving) of a stented vascular segment following the cell delivery. Although it is not necessary to understand the mechanism of an invention, it is believed that the delivery of MSCs may result in a therapeutic effect as data from several different models support the capacity of MSCs to support re-endothelialization, likely through indirect paracrine mechanisms. Kinnaird et al., "Bone-marrow-derived cells for enhancing collateral development: mechanisms, animal data, and initial clinical experiences" *Circ Res.* 95(4): 354-363 (2004); Wu et al., "Effect of paclitaxel and mesenchymal stem cells seeding on ex vivo vascular endothelial repair and smooth muscle cells growth" *J Cardiovasc Pharmacol.* 46(6):779-786 (2005); Yue et al, "Mesenchymal stem cells differentiate into an endothelial phenotype, reduce neointimal formation, and enhance endothelial function in a rat vein grafting model" *Stem Cells Dev.* 17(4):785-793 (2008); Forte et al., "Mesenchymal stem cells effectively reduce surgically induced stenosis in rat carotids" *J Cell Physiol* 217(3):789-799 (2008); and Wang et al., "Late outgrowth endothelial cells derived from Wharton jelly in human umbilical cord reduce neointimal formation after vascular injury: involvement of pigment epithelium-derived factor" *Arterioscler Thromb Vasc Biol.* 29(6):816-822 (2009). It is further believed that MSCs may differentiate towards an endothelial phenotype. Liu et al., "Characterization of endothelial-like cells derived from human mesenchymal stem cells" *J Thromb Haemost.* 5(4):826-834 (2007); and Dong et al., "Response of mesenchymal stem cells to shear stress in tissue-engineered vascular grafts" *Acta Pharmacol Sin.* 30(5):530-536 (2009).

C. Overall Clinical Application

Cell delivery using acoustic radiation force as described herein can potentially be used for endoluminal seeding of any cell type (i.e., for example, progenitor cells, epithelial progenitor cells, mesenchymal stem cells, etc.). For example, in clinical applications MSCs have been demonstrated herein as a successful embodiment. These data are surprising over previous reports suggesting that MSCs undergo limited endothelial differentiation. Tögel et al., "Vasculotropic paracrine actions of infused mesenchymal stem cells are important to the recovery from acute kidney injury" *Am J Physiol Renal Physiol.* 292:F1626-1635 (2007); and Quevedo et al., "Allogeneic mesenchymal stem cells restore cardiac function in chronic ischemic cardiomyopathy via trilineage differentiating capacity" *Proc Natl Acad Sci USA.* 106:14022-14027 (2009).

Previous reports suggested that systemic delivery of MSCs in vivo leads to retention of a limited number of cells in the perivascular space, and that this retention is likely a natural niche of MSC-like cells in most organs. Toma et al., "Fate of culture expanded mesenchymal stem cells in the microvasculature: in vivo observations of cell kinetics" *Circ Res.* 104: 398-402 (2009); and Crisan et al., "A perivascular origin for mesenchymal stem cells in multiple human organs" *Cell Stem Cell.* 3:301-313 (2008), respectively. As such, the MSCs are more likely to contribute in vivo to vascular repair indirectly, possibly via a paracrine mechanism. Indeed, it has been reported that MSCs secrete VEGF, IGF and HGF 21, stimulate angiogenesis and may have a positive effect on the endothelium. Tögel et al., "Vasculotropic paracrine actions of infused mesenchymal stem cells are important to the recovery from acute kidney injury" *Am J Physiol Renal Physiol.* 292: F1626-1635 (2007). For example, this potential MSC paracrine effect has been shown in vascular prostheses, where MSC seeding facilitates endothelialization and prevents neointimal proliferation within the graft after implantation, resulting increased graft patency. Hashi et al., "Antithrombogenic property of bone marrow mesenchymal stem cells in nanofibrous vascular grafts" *Proc Natl Acad Sci USA.* 104: 11915-11920 (2007); and Mirza et al., "Undifferentiated mesenchymal stem cells seeded on a vascular prosthesis contribute to the restoration of a physiologic vascular wall" *J Vasc Surg.* 47:1313-1321 (2008). Lastly, MSCs have been already used for clinical applications in an allogeneic fashion primarily for their indirect regenerative and anti-inflammatory properties, and thus can be readily available to the clinician. Le Blanc et al., "Mesenchymal stem cells for treatment of steroid-resistant, severe, acute graft-versus-host disease: a phase II study" *Lancet* 371:1579-1586 (2008); and Hare et al., "A randomized, double-blind, placebo-controlled, dose escalation study of intravenous adult human mesenchymal stem cells after acute myocardial infarction" *J Am Coll Cardiol.* 54:2277-2278 (2009).

The reported toxicity of microbubbles observed in in vitro testing may not be indicative of in vivo toxicity. For example, in the data presented herein an extended exposure of cationic microbubbles to MSCs in vitro led to a 5% excess cell death. This observation is consistent with the reported toxicity of cationic lipids and may be partially related to membrane destabilization. Soenen et al., "Addressing the problem of cationic lipid mediated toxicity: the magnetoliposome model" *Biomaterials* 30:3691-3701 (2009). In contrast, for in vivo clinical applications MSC exposure to cationic microbubbles is limited to the time frame of cell delivery. Although it is not necessary to understand the mechanism of an invention, it is believed that the cationic microbubbles dissociate from the MSCs following delivery, possibly due to microbubble charge neutralization and/or high hydrodynamic stress. For example, data provided herein collected at approximately 24 hr after mb:MSC complex delivery clearly demonstrated survival and spreading of the MSCs on the luminal surface of the treated artery. An alternative approach would be to attach microbubbles to MSCs by modifying the microbubble shell to bear specific targeting ligands that would enable microbubble attachment via specific ligand-receptor interactions.

In conclusion, the data provided herein successfully demonstrates that acoustic radiation force can successfully target therapeutic cells to a tissue treatment site. Other embodiments may comprise longer follow-up periods and/or other cells types, such as EPCs. Alternatively, such therapeutic cells may also serve as a potential paracrine nidus for accelerated restoration of endothelium. In some embodiments, the presently disclosed methods provide for vascular repair following angioplasty and stenting, as well as therapies to alter development of atherosclerotic plaque.

V. Microbubble Compositions

Microbubbles may be encapsulated by shells of varying chemical compositions. The composition of a microbubble shell and ligand attachment chemistry can be varied, with resulting differences in acoustic behavior and/or affinity of the microbubble for binding to a biological cell. Currently, those in the art have attempted to improve the use of microbubbles to deliver incorporated and/or encapsulated drugs. In one embodiment, the present invention contemplates the attachment of a progenitor cell on the outside surface of a microbubble in order to facilitate contact with a target tissue. Although it is not necessary to understand the mechanism of an invention, it is believed that using a biological progenitor cell will actively participate in stimulating biological pathways in ways not possible by conventional therapeutic drugs.

In some embodiments, acoustic radiation force mediated cell delivery employed cationic microbubbles that readily associated with the slightly negatively-charged MSCs. That data presented herein confirm cationic microbubble attachment to the MSCs by both microscopic and flow cytometric means, as exemplified by an increased side-scatter of mb-MSC complexes. This optical property of the mb-MSCs was exploited to characterize the association between MSCs and microbubbles by quantitating the number of cells coated with microbubbles, as well as the number of microbubbles per cell. These data provide a useful metric to evaluate the efficacy of alternative methods for coating cells with microbubbles in the effort to maximize the ultimate therapeutic effects.

In some embodiments, the present invention contemplates compositions comprising microbubbles that are acoustically active attached to progenitor cells that are therapeutically active. Microbubbles compatible with the present invention may be selected without undue experimentation as representative examples of useful compositions are described below.

Commercial sources of microbubbles are exemplified by Optison (General Electric), DMP-115 (Lantheus Imaging), Acusphere, and BR1 (Bracco Diagnostics); as well as the acoustically active liposomes composed of small nongaseous multilamellar lipid vesicles. Alkan-Onyuksel, et al., *J. Pharm. Sci* 85:486-490 (1996) (incorporated herein by reference in its entirety for all purposes), and acoustically active lipospheres (ImaRx Therapeutics).

Microbubbles may also be created by microencapsulating a solid core of ammonium carbonate which is then removed by decomposition and freeze-drying. Suitable polymers preferably are FDA approved and susceptible to in vivo degradation such as, e.g., poly D,L(lactide-co-glycolide) (PLGA). Spray drying, coacervation and solvent extraction methods may be used. Ideally, the resulting particles have a mean particle size on the order of less than or equal to 10 µm. Compounds may be loaded onto the capsules by adsorption. Wheatley et al., *Mat. Res. Soc. Symp. Proc.* 550:113-118 (1999)(the entire disclosure of which is hereby incorporated by reference for all purposes)

Procedures to adjust particle size have been reported and include but are not limited to, extrusion, filtration, sonication, homogenization, employing a laminar stream of a core of liquid introduced into an immiscible sheath of liquid, extrusion under pressure through pores of defined size, and similar methods. Unger, et al., U.S. Patent Publication No. US 2003/0039613 A1 (incorporated herein by reference in its entirety for all purposes). Particle sizes useful for practice of the present invention will vary depending on microbubble composition. In general, the present invention contemplates microbubbles approximately 10 µm or less in diameter. Alternatively, models exist that are useful for guiding the skilled practitioner on electing frequencies, pressures, and other parameters, based on the size and physical properties of the carriers. Particle size may be determined using, e.g., a Model 770A Accusizer particle sizer (Particle Sizing Systems, Santa Barbara, Calif.). Especially useful for practice of the invention are particles that comprise an oil having a kinematic viscosity at 37° C. between about 1 $mm^2$/sec and about 100 $mm^2$/sec, or between about 10 $mm^2$/sec and about 80 $mm^2$/sec, or between about 20 $mm^2$/sec and 60 $mm^2$/sec. Kinematic viscosity can be measured using a device such as a KV5000 Kinematic Viscosity Bath available from Koehler Instrument Co., Inc. (Bohemia, N.Y.).

VI. Acoustically Active Microbubbles

A. Acoustically-Mediated Drug Release

Acoustically active microbubbles have been used to transport and deliver incorporated and/or encapsulated drugs. These references rely upon the application of an acoustic pressure force to rupture the microbubble (i.e., not move the microbubble) in order to release the drug to the biological target.

Unilammelar phospholipid microspheres that are sensitive to acoustically-induced rupture have been used for delivery and release of therapeutic compounds. These microspheres comprise an encapsulated gas (i.e., for example, perfluorocarbon) that expands when exposed to an acoustical pressure. The gas expansion then induces rupture of the microsphere shell, thereby releasing the encapsulated contents. These microspheres may also include a targeting ligand, such as steroid prodrugs, lipids, proteins, polymers and/or auxiliary stabilizing materials. These ligands allow for a microsphere to attach to a specific biological target before the acoustical pressure is applied. Upon administration to a patient, the microsphere is induced to rupture by application of ultrasound, thereby resulting in release of the therapeutic compound(s). This reference does not disclose moving, transporting, or directing gas-filled stable microbubbles using an acoustic radiation force. Unger et al. "Acoustically Active Drug Delivery Systems," U.S. Pat. No. 6,416,740 (issued Jul. 9, 2002)(herein incorporated by reference).

Acoustically active lipid-coated microspheres have been used for diagnostic imaging and site-specific drug delivery. In particular, microspheres bearing specific ligands for disease detection and targeted gene delivery were described. This reference does not disclose applications related to stents or delivery of endothelial progenitor cells. Unger et al. (2004) Therapeutic Applications Of Lipid-Coated Microbubbles, Advanced Drug Delivery Reviews 56(9): 1291-1314. Additionally, the delivery of diagnostic and/or therapeutically active agents comprising gas-filled targetable microbubbles stabilized by monolayers of film-forming surfactants have been reported. Klaveness et al., U.S. Patent Application Publication US 2002/0102215 A1 (incorporated herein by reference in its entirety).

B. Acoustically-Mediated Movement

Ultrasound radiation forces were reported to direct drug delivery capsules to a target site. Additional acoustic pressure was then used to fragment the localized capsules. However, as with the conventionally administered microbubble technology (supra) such microbubbles incorporate and/or encapsulate drugs and do not attach progenitor cells on the surface of the microbubbles. Dayton et al. "Ultrasonic Concentration Of Drug Delivery Capsules," U.S. Pat. No. 7,358,226 (herein incorporated by reference). As the data herein demonstrates, such progenitor cell attachment results in therapeutic responses (i.e., for example, stent endothelialization) not possible with any known conventional drug or pharmacologic compound.

Methods for selectively slowing and stopping acoustically active particles (including gas-filled bubbles) in a flowing fluid have been reported by using ultrasonic waves to force the particles against a surface (such as a blood vessel). Ultrasonic energy were then be used to break apart, shrink or dissolve these particles. Katz et al. "Method And Apparatus For Stopping And Dissolving Acoustically Active Particles In Fluid," United States Patent Application Number 20050220711 (herein incorporated by reference).

Other uses of acoustic radiation forces involve an acoustically-driven cell transfer and mixing system that combines the laminar flow properties of micro-scale fluidics with ultrasonic forces was reported. The disclosed procedure can be used to either separate samples as they pass through a low power ultrasound field or mix samples as they pass through a high power ultrasound field. Hawkes et al. "Continuous Cell Washing And Mixing Driven By An Ultrasound Standing Wave Within a Microfluidic Channel" *Lab Chip* 4: 446-452 (2004). Further, "Acoustic tweezers" using ultrasound waves (i.e., for example, pulsed laser light) was disclosed to generate high-frequency vibrations that heat and expand a polymer surface. Cells may be transported along this polymer surface by moving the laser. Massachusetts Institute of Technology, "Moving Cells With Sound" *Technology Review*, (November 2004).

Basic acoustical relationships defining microbubble movement include, but are not limited to, center frequency, pressure, pulse length and fundamental or resonance frequencies. Dayton, et al. *J. Acoust. Soc. Am.* 112 (5):2183-2192 (November 2002) (incorporated herein by reference in its entirety for all purposes). Ultrasound systems useful for practicing the invention include, but are not limited to, a phased system array (HDI c000cv, Advanced Technologies Laboratories), the system described in U.S. Pat. No. 5,558,092, to Unger, et al., and may include, but are not limited to, external applications (i.e., for example, skin and other superficial tissues) and deep biological structures, wherein the application of sonic energy may be delivered via interstitial probes and/or intravascular ultrasound catheters.

The present progenitor cell-tagged microbubbles comprise an acoustically active gas, such as an inert gas. Suitable gases are inert and biocompatible, and include, for example, air, noble gases, such as helium, rubidium, hyperpolarized xenon, hyperpolarized argon, hyperpolarized helium, neon, argon, xenon, carbon dioxide, nitrogen, fluorine, oxygen, sulfur-based gases, such as sulfur hexafluoride and sulfur tetrafluoride, fluorinated gases, including, for example, partially fluorinated gases or completely fluorinated gases, and mixtures thereof. Exemplary fluorinated gases include fluorocarbon gases, such as perfluorocarbon gases and mixtures thereof. Paramagnetic gases, such as, $^{17}O_2$ may also be used in the stabilizing materials and vesicles.

In some embodiments, the acoustically active gas comprises a fluorinated gas, which includes gases containing one or more than one fluorine atom. For example, such gases may contain more than one fluorine atom (i.e., for example, perfluorocarbons; fully fluorinated fluorocarbons). The perfluorocarbon gas may be saturated, unsaturated or cyclic, including, for example, perfluoromethane, perfluoroethane, perfluoropropane, perfluorocyclopropane, perfluorobutane, perfluorocyclobutane, perfluoropentane, perfluorocylcopentane, perfluorohexane, perfluoroheptane, perfluorooctane, perfluorononane, and mixtures thereof Alternatively, the perfluorocarbon gas is perfluoropropane or perfluorobutane. Sulfur hexafluoride may also be used. In other embodiments, heptafluoropropane, including 1,1,1,2,3,3,3-heptafluoropropane and its isomer, 1,1,2,2,3,3,3-heptafluoropropane are suitable for the present invention. Mixtures of different types of gases, such as mixtures of a perfluorocarbon gas and another type of gas, such as, for example, air or nitrogen, can also be used in the compositions of the present invention. Other gases, including the gases exemplified above, would be apparent to one skilled in the art in view of the present disclosure.

VII. Acoustic Radiation Forces

Acoustic radiation force (RF), also termed Bjerken's force, refers to a displacement of a deformable object resulting from the object's absorption of sound wave energy. Chen et al., "Radiation force on a spherical object in an axisymmetric wave field and its application to the calibration of high-frequency transducers" *J Acoust Soc Am.* 99(2):713-724 (1996). Microbubble contrast agents, which are gas-filled, highly compressible micron-sized particles, are particularly susceptible to the effects of RF exerted by ultrasound, as the RF effect is substantially larger with compressible objects.

The RF is maximal when the transmitted ultrasound frequency corresponds to the natural resonance frequency of the particle. Leighton, The Acoustic Bubble. Academic Press, San Diego. 341:367 (1994). If a resonating frequency of microbubbles falls within the frequency of clinical ultrasound systems, it may be possible control microbubble motion (i.e., for example, direction and velocity) for therapeutic purposes by using clinically available ultrasound imaging systems. Zhao et al., "Radiation-force assisted targeting facilitates ultrasonic molecular imaging" *Mol Imaging.* 3(3):135-148 (2004). This effect was proposed to be useful in increasing the interaction between the targeted microbubble contrast agents and their substrate, as well as in targeted drug delivery. Dayton et al., "Acoustic radiation force in vivo: a mechanism to assist targeting of microbubbles" *Ultrasound Med Biol.*

25(8):1195-1201 (1999); Tarns et al., "Therapeutic effects of paclitaxel-containing ultrasound contrast agents" *Ultrasound Med Biol.* 32(11):1771-1780 (2006); and Dayton et al., "Application of ultrasound to selectively localize nanodroplets for targeted imaging and therapy" *Mol Imaging* 5(3):160-174 (2006).

In one embodiment, the present invention contemplates an acoustically active microbubble capable of providing cell-based therapy to prevent and/or treat cardiovascular disease. In one embodiment, the cardiovascular disease comprises a vascular injury. In one embodiment, the vascular injury occurs as a result of percutaneous coronary interventions. Other known clinical treatments including, but not limited to, balloon angioplasty and/or stent placement, also results in arterial injury and tissue denudation which lead to vascular thromboses (i.e., for example, coronary thrombosis). In one embodiment, the method comprises treating the development of late thrombosis within coronary stents. Late thrombosis is emerging as a significant complication of drug eluting stent placement, and thought to be due to incomplete re-endothelialization of the stented arterial segment.

The physics governing gaseous microbubble movement, transport, directing, or steering (as by, e.g., radiation force) involve the interaction of microbubbles with incident ultrasound energy upon the microbubbles For example, some emissions useful for microbubble movement have a peak resonant frequency of between about 0.5 MHz and about 10 MHz. Of course, the peak frequency of a gas-filled microsphere will vary depending on the diameter and, to some extent, the elasticity of the microspheres, with the larger and more flexible microspheres having a lower frequency than the smaller and less flexible microspheres.

The peak frequency can be determined by an ordinary skilled practitioner either in vivo or in vitro, but preferably in vivo, by exposing the microsphere carriers to ultrasound, receiving the reflected frequency signals and analyzing the spectrum of signals using conventional means. The peak, as so determined, corresponds to the peak frequency.

Gas-filled microbubbles will rupture if exposed to frequency ultrasound of high intensity (wattage) and duration (time). This higher energy, however, may result in heating and/or rupture at their peak frequency, which may, or may not, be desirable.

Acoustical radiation has been used for both diagnostic and therapeutic purposes. A therapeutic ultrasound device may be used which employs tone bursts at narrow frequency bands. For example, two frequencies of ultrasound may be employed. The first frequency may be x, and the second frequency may be y. In one embodiment, the device would be designed such that the focal zones of the first and second frequencies converge to a single focal zone. The focal zone of the device may then be directed to the microbubble compositions, for example, microbubble-tagged EPCs, within the tissue of interest. An ultrasound device may provide superior therapy with simultaneous application of the x and y frequencies of ultrasound energy. It is contemplated that, in the case of ultrasound involving microbubble movement, this implementation may provide improved movement of microbubbles as compared to ultrasound energy involving a single frequency. Lower peak energy but longer duration ultrasound may also be used with an ultrasound device to direct microbubbles. An ultrasound device which may be employed in connection with the aforementioned dual frequency technique, for example, in Kawabata, et al., *Ultrasonics Sonochemistry,* 3:1-5 (1996), the disclosure of which is hereby incorporated by reference herein in its entirety.

Others have used various types of diagnostic ultrasound imaging devices, the particular type or model of the device not being critical to the method of the invention. Also suitable are devices designed for administering ultrasonic hyperthermia. U.S. Pat. Nos. 4,620,546, 4,658,828, and 4,586,512 (all incorporated herein by reference). Preferably, the device employs a resonant frequency (RF) spectral analyzer. The transducer probes may be applied externally or may be implanted.

Although application of the various principles will be readily apparent to one skilled in the art, in view of the present disclosure, by way of general guidance, for gas filled vesicles of about 1.5 to about 10 µm in mean outside diameter, the frequency required to move the microbubbles will generally be in the range of about 1 to about 10 MHz. By adjusting the focal zone to the center of the target tissue (i.e., for example, an arterial segment) the gas filled microbubbles can be visualized under real time ultrasound as they accumulate within the target tissue. For larger diameter gas filled vesicles, e.g., greater than 3 µm in mean outside diameter, a lower frequency transducer may be more effective in accomplishing microbubble movement. For example, a lower frequency transducer of 3.5 MHz (20 mm curved array model) may be selected.

The table below shows the ranges of energies transmitted to tissues from diagnostic ultrasound on commonly used instruments such as the Piconics Inc. (Tyngsboro, Mass.) Portascan general purpose scanner with receiver pulser 1966 Model 661; the Picker (Cleveland, Ohio) Echoview 8L Scanner including 80C System or the Medisonics (Mountain View, Calif.) Model D-9 Versatone Bidirectional Doppler. In general, these ranges of energies employed in pulse repetition are useful for diagnosis and monitoring gas-filled liposomes.

TABLE 6

Power and Intensities Produced by Diagnostic Equipment*

| Pulse repetition rate (Hz) | Total ultrasonic power output (mW) | Average intensity at transducer face (W/m$^2$) |
| --- | --- | --- |
| 520 | 4.2 | 32 |
| 676 | 9.4 | 71 |
| 806 | 6.8 | 24 |
| 1000 | 14.4 | 51 |
| 1538 | 2.4 | 8.5 |

*Values obtained from Carson et al., Ultrasound in Med. & Biol., 3:341-350 (1978), the disclosure of which is hereby incorporated herein by reference in its entirety.

Either fixed frequency or modulated frequency ultrasound may be used. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Unfocused, fixed frequency, low energy ultrasound may stabilize microbubble gaseous expansion and be useful for microbubble-induced movement.

Ultrasound may produce a radiation force that is exerted upon objects (i.e., for example, a microbubble) in a medium (i.e., for example, blood) with an acoustic impedance different than that of the medium. The ability of a radiation force to concentrate microbubbles in-vitro and in-vivo has been shown. Dayton et al., *Ultrasound in Med. & Biol.,* 25(8): 1195-1201(1999). An ultrasound transducer pulsing at 5 MHz center frequency, 10 kHz pulse repetition frequency ("PRF"), and 800 kPa peak pressure, has been shown to concentrate microbubbles against a vessel wall in-vivo, and reduce the velocity of these flowing agents an order of magnitude.

However, to this date, the application of acoustic radiation to concentrate a microbubble-tagged progenitor cell (i.e., for example, an endothelial progenitor cell) has not been demonstrated, nor have the combined effects of radiation force-induced concentration and accelerated biological pathway acceleration (i.e., for example, endothelial proliferation). Ultrasonically-directed microbubble movement is a new idea, which is still in research trials. Initial results suggest that this technology has the potential for significant clinical impact. Although it is not necessary to understand the mechanism of an invention, it is believed that acoustic radiation force acts on particles in a fluid, thereby allowing post-administration manipulation of the carriers within a biological system (i.e., for example, a cardiovascular system). One advantage of the present invention contemplates that the microbubbles remain stable while exposed to acoustic pressure. Microbubble stability allows a more complete displacement of the microbubbles to the intended biological target without rupturing. The potential to concentrate microbubbles at the site of interest before disruption, as described by this invention, provides a significant increase in the therapeutic efficacy of progenitor cell-mediated biological effects. In some embodiments, the present invention contemplates using microbubbles in regards to cell transport and concentration as opposed to incorporating and/or encapsulating drugs and/or pharmacologic compounds for release at or near a biological target.

In one embodiment, the invention contemplates an ultrasound radiation force to enhance effectiveness of microbubbles such as acoustically active microbubbles and other particles useful as carriers in the practice of the invention. Radiation force is used to "push" or concentrate carriers along the wall of a vessel. In small blood vessels, particles such as cells or carriers tend to flow along the center of the vessel, rather than along the sides. By concentrating the carriers along the vessel wall, a larger percentage of a microbubble-tagged progenitor cell (i.e., for example, an endothelial progenitor cell) is delivered to its biological target (i.e., for example, vascular endothelium). Although it is not necessary to understand the mechanism of an invention, it is believed that the concentrated delivery of a progenitor cell to its biological target results in an accelerated, improved, and superior target response when compared to an administration of the progenitor cell with being tagged to a microbubble.

In one embodiment, the present invention contemplates methods of using ultrasound and a microbubble to enhance delivery of a progenitor cell at an intended biological target including, but not limited to:

1. Ultrasound e.g., at center frequencies about 0.1 MHz-40 MHz, and at an acoustic pressure of approximately 20 kPa-6 MPa, and a long pulse length (e.g., about >10 cycles) or a short pulse length (e.g., about <10 cycles) and high pulse repetition frequency (e.g., about >500 Hz) to produce radiation force and initiate and/or maintain microbubble movement. The specific parameters will depend on the choice of microbubble, as detailed further below, and can be readily determined by ordinarily skilled artisans having the benefit of this disclosure.
2. Ultrasound e.g., at about 0.1 MHz-40 MHz, and at an acoustic pressure of approximately 20 kPa-6 MPa and a long cycle length (e.g., about >10 cycles) or a short cycle length (e.g., about <10 cycles) and high pulse repetition frequency (e.g., about >500 Hz) to produce radiation force and reduce and/or stop microbubble movement. Again, the specific parameters chosen depend on the choice of carrier, as detailed further below, and can be readily determined by ordinarily skilled artisans having the benefit of this disclosure.
3. A combination of ultrasonic transducers, specifically designed for production of acoustic radiation force according to the description of 1 or 2, supra or any combination.
4. A single ultrasonic transducer specifically designed for production of acoustic radiation force according to the description of 1 or 2, supra or any combination.
5. Any combination of the above techniques.

A related technique involves a technology designated as free flow acoustophoresis (FFA). FFA is capable of continuously separating mixed particle suspensions into multiple outlet fractions. Acoustic forces are utilized, but separate particles based on their size and density. For example, microfluidic separation chips may be fabricated using conventional microfabrication methods. Particle separation can be accomplished by combining laminar flow with the axial acoustic primary radiation force in an ultrasonic standing wave field. Dissimilar suspended particles are laterally translated to different regions of the laminar flow profile, which was split into multiple outlets. Petersson et al., "Free flow acoustophoresis: microfluidic-based mode of particle and cell separation" *Anal Chem.* 79:5117-5123 (2007).

The use of ultrasound radiation force to manipulate microbubbles in blood vessels has attracted recent interest as a method to increase the efficiency of ultrasonic molecular imaging and drug delivery. However, recent studies indicate that microbubble oscillation is diminished within small blood vessels. For example, when using a 0.1- to 1-MPa ultrasound pulse, microbubbles (radius of 1, 1.5 and 2 micron) within 12 micron tubes translate 5 to 10 times less than those within 200 micron tubes. Application of a pulse train with a high pulse repetition frequency displaces microbubbles to the wall of 12- and 200-micron tubes within an interval (approximately 1 s) that is reasonable for clinical translation. Such observations suggested that microbubbles may be useful for contrast-assisted ultrasound. Zheng et al., "Ultrasound-driven microbubble oscillation and translation within small phantom vessels" *Ultrasound Med Biol.* 33:1978-1987 (2007).

A. Intravascular Ultrasound (IVUS)

The application of acoustic RF has different requirements as compared to ultrasound imaging. For effective acoustic RF application, the ultrasound power and duty-cycle have to be higher. For instance, preliminary data presented herein were obtained with 10 MHz, 40% duty-cycle and 1.2 MPa peak amplitude. In contrast, to achieve spatial resolution a standard IVUS imaging catheter emits at 20-40 MHz, with duty-cycle of less than 0.4%. However, the RF-IVUS application does not need the spatial resolution of an imaging catheter, such that the time lost for the crystal rotation and the image processing can be translated into a significantly longer duty cycle. Adaptation of an existing single element or multiarray solid-state catheter for RF thus appears theoretically feasible. The alternative is to use a single, non-rotating cylindrical crystal than can emit ultrasound radially. Nonetheless, it is believed that the ultrasound power required to effectively displace progenitor cell-microbubble complexes is well within the safety guidelines limits for ultrasound imaging.

The present invention solves a significant problem that has previously prevented an effective form of cell-based therapy. This problem was especially prevalent for the intravascular luminal delivery of cell-based therapies to a specific arterial segment. For example, drug delivery balloon based catheter systems may not be applicable for cell delivery, as the delivery system itself may affect cell viability (i.e., intravascular cell abrasion and injury is known to occur during balloon-based techniques). Further, a simple systemic injection (i.e., for example, an intravenous injection) of the cells upstream of the segment of interest is likely to be inefficient, due to the limited physical interaction between the cells and the arterial wall. Further, such systemic injections are prone to side effects, such as, potential unwanted systemic pro-angiogenic effects. Even techniques that implant pre-coated stents with specific ligands for EPCs (i.e., for example, a CD34 antibody) have limitations. For example, these pre-coated stents have space between the struts (representing most of the surface of the stented segment) that remains untreated (i.e., is devoid of attached antibody).

In some embodiments, the present invention contemplates taking advantage of recent advances in intravascular ultrasound (IVUS). IVUS has become a reliable imaging method for quantitative and qualitative exploration of the coronary anatomy using percutaneous interventions (PCIs). Currently, phase-array and mechanical high-frequency transducers are available, as well as algorithms for tissue composition analysis. In the setting of PCI, IVUS is a safe procedure with minimal additional risks involved. IVUS is capable of defining coronary anatomy, evaluating stent deployment, and/or identifying related complications.

In some embodiments, the present invention contemplates using IVUS for therapeutic purposes. Although it is not necessary to understand the mechanism of an invention, it is believed that based upon the principle of acoustic radiation force (RF; also known as primary Bjerknes force) a gas filled microbubble exposed to an ultrasound energy field will be displaced away from the energy source. It is further believed that this displacement occurs because of relatively large amplitude bubble oscillations in response to each ultrasound pulse. The displacement (i.e., for example, movement) is proportional to the compressibility of the particle, which is why the RF effect is significantly enhanced on gas-filled lipid microbubbles. Zheng et al., "Ultrasound-driven microbubble oscillation and translation within small phantom vessels" *Ultrasound Med Biol.* 33:1978-1987 (2007); and Dayton et al., "Acoustic radiation force in vivo: a mechanism to assist targeting of microbubbles" *Ultrasound Med Biol.* 25:1195-1201 (1999). A microbubble displacement movement also takes advantage of secondary Bjerkens forces that are related to interactions between bubbles in an ultrasonic field, resulting in weak bubble attraction to each other.

Figure 6:
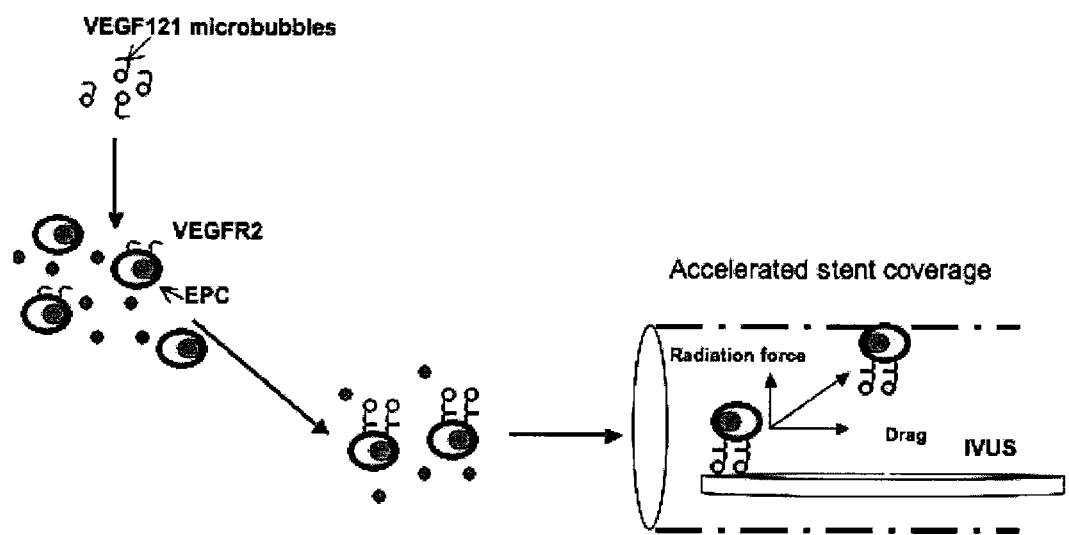
FIG. 6 illustrates a schematic showing a testing platform for using acoustically active progenitor cell-microbubble complexes to contact a vessel wall with an intravascular ultrasonic system (IVUS).

In the present invention, acoustically active microbubbles are utilized as 'an engine' that provides directional movement of the progenitor cells to which the microbubbles are attached. In one embodiment, an IVUS catheter is centrally placed in a coronary artery, wherein radial RF directs (i.e., moves) microbubbles passing in the vicinity of the catheter to the periphery of the vessel lumen. In one embodiment, the peripheral movement of the microbubbles facilitates contact of the progenitor cells with the endothelial tissue. In one embodiment, the microbubbles are approximately 1-3 microns in diameter, wherein the microbubbles remain in the intravascular spaces. In one embodiment, the microbubbles, display cell-specific ligands, thereby allowing attachment to specific progenitor cells (i.e., for example, EPCs). Such design, synthesis, and acoustic characterization of cell-based microbubble technology has been developed at the University of Pittsburgh Center for Ultrasound Molecular Imaging and Therapeutics in the Cardiovascular Institute. Villanueva et al., "Myocardial ischemic memory imaging with molecular echocardiography" *Circulation* 115:345-352 (2007). See, FIG. 6. For example, by using vascular endothelial growth factor 121 (VEGF 121) as the cell-specific ligand on the microbubble outer surface, native EPCs can be collected, isolated and attached to the microbubbles using an in vivo process. Alternatively, the microbubble-cell ligand can be injected in vivo, thereby allowing attachment of EPCs within a patients circulatory system. In either the in vitro or in vivo embodiment, the present invention contemplates personalized cell-based therapy, wherein the cells presented to the target tissue may be patient-derived cells. Thereafter, radiation force (i.e., acoustical radiation force) may be applied using IVUS thereby resulting in a forced circumferential marginalization of these cell-microbubble complexes. Although it is not necessary to understand the mechanism of an invention, it is believed that such marginalization increasing the cell's physical interaction with an arterial tissue segment of interest and the tissue's natural ligands, thereby accelerating endothelial cell proliferation. It is further believed that this method essentially accelerates the participation of the circulating EPCs in the restoration of a functional endothelial layer in the denuded arterial segment, thereby promoting tissue regeneration and healing.

Preliminary in vitro testing reveals that at higher frequency there is minimal direct RF effect on progenitor cells alone, due to the much lower resonance frequency and the lesser compressibility of the cells as compared to the microbubbles (data not shown). A smaller transducer can be engineered for higher frequencies that would be useful to improve catheter-based technologies. Furthermore, such transducer improvements may allow for adaptation of existing IVUS technology to deliver more efficient RF.

Figure 7:
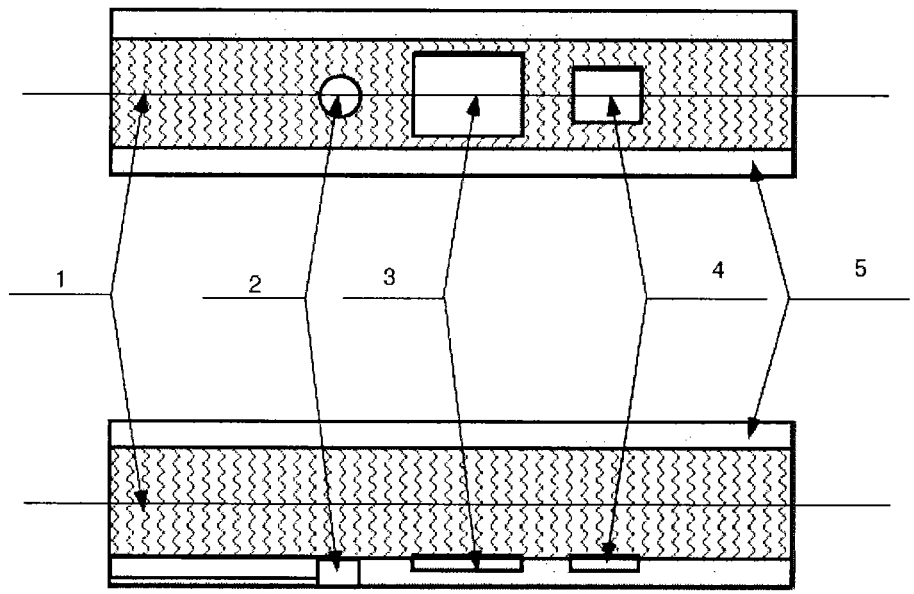
FIG. 7 illustrates a schematic showing a multi-port catheter tip capable of dispensing different compositions either sequentially or simultaneously.

In one embodiment, the present invention contemplates a device comprising a multifunctional intravascular catheter. In one embodiment, the catheter comprises a multiport tip, capable of dispensing different compositions from each tip, either sequentially or simultaneously. FIG. 7. In some embodiments, the catheter comprises:

(1) A shaft (item #1) that can perform mechanical rotation when necessary to perform imaging and radiation force treatment.

(2) An injection port (item #2) that allows local delivery of microbubbles, biological cells, and biological cells treated with microbubbles, and various drugs;

(3) An ultrasound transducer (item #3) that generate the radiation force to enhance and accelerate the local delivery of biological agent to the stent-covered blood vessel or vascular graft.

(4) An ultrasound transducer (item #4) that can perform high frequency IVUS ultrasound imaging when necessary.

(5) The same ultrasound transducer (item #4) that can be used to monitor the effectiveness of the cell/biological agent delivery by item #3.

(6) An electronic system (not shown) that generates custom-waveform to the transducer (item #3).

(7) A custom motor drive (not shown) that controls the rotation of the shaft (item #1) at appropriate and possible different speeds for to perform imaging by ultrasound transducer (item #4) and at to perform local delivery of stem cells and/or other biological agents by ultrasound transducer (item #3).

(8) The same motor drive that controls axial motion of the catheter (pulling) such that a length of stent/graft/vessel wall can be treated sequentially.

intravascular catheter is presented. Other possible implementations:

(9) The ultrasound transducer for imaging (Item #4) is realized with an array of transducer elements such that rotation is not necessary to perform imaging;

(10) The ultrasound transducer for radiation force generation is realized with a size that cover substantially all of the circumference of the shaft such that rotation is not necessary to complete the treatment of all directions of the stent/graft/vessel wall.

(11) The ultrasound transducer for radiation force generation is realized with a sparse array of 4-8 elements such that all or part of the stent/graft/vessel wall can be treated selectively without the need of rotation.

(12) The ultrasound transducer for radiation force generation is realized with a higher density of elements (approximately 8-32), such that the ultrasound beam pattern can be changed electronically.

B. Catheter-Based RF Delivery

In some embodiments, the present invention contemplates methods for driving gas-filled microbubbles providing an external single-element immersible transducer (i.e., for example, one having a 5 MHz center frequency). In one embodiment, the method comprises cellular endoluminal paving with cell-based therapies, wherein an immersible transducer (i.e., for example, an intravascular catheter) generates RF ultrasound comprising appropriate characteristics. Unlike imaging intravascular ultrasound (IVUS) catheters, the present invention contemplates ultrasound (US) devices emitting RF having longer duty cycles at lower frequencies.

Figure 11A:
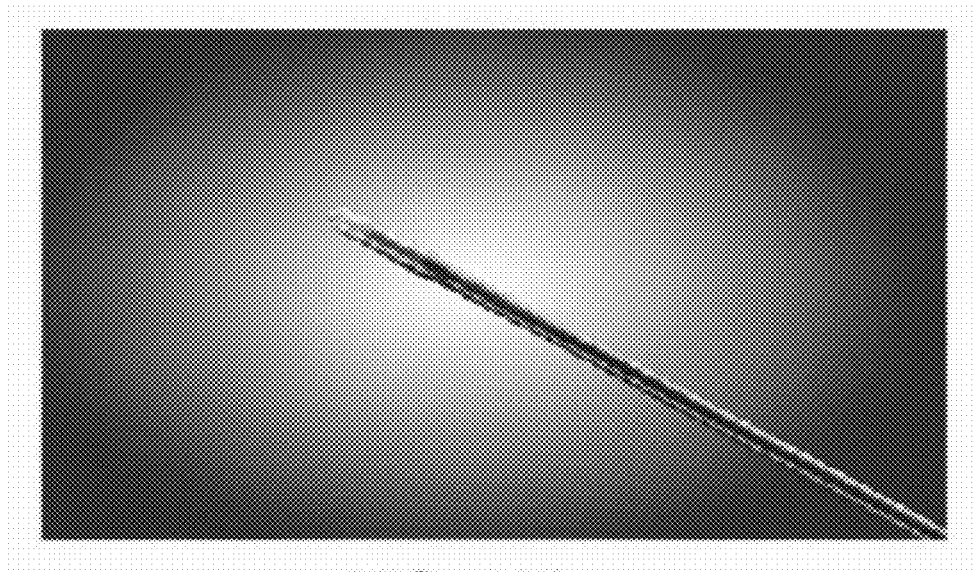
FIG. 11A.

One suitable intravenous catheter was initially designed for ultrasound-facilitated thrombolysis (i.e., for example, EkoSonic SV, Ekos Corp, Bothell Wash.). See, FIG. 11A. This particular catheter is rated 3F with an active element at the tip measuring 2 mm in length. It has been reported that this catheter delivers ultrasound at 1.7 MHz and tolerates duty cycles of up to 8.5% for 2 hrs without significant heating or deleterious biological effects. Soltani et al., "Absence of biological damage from prolonged exposure to intravascular ultrasound: a swine model" *Ultrasonics* 46(1):60-67 (2008). Further, this catheter is FDA-approved for coronary and neurological clot lysis and is currently being used clinically for stroke and critical limb ischemia. Tomsik et al., "Interventional Management of Stroke II Investigators. Revascularization results in the Interventional Management of Stroke II trial" *AJNR Am J Neuroradiol.* 29(3):582-587 (2008); and Wissgott et al., "Treatment of critical limb ischemia using ultrasound-enhanced thrombolysis (PARES Trial): final results" *Endovasc Ther.* 14(4):438-443 (2007), respectively.

The Ekos intravenous catheter was compared to a single element transducer by performing acoustic field characterizations and calibrations using a capsule hydrophone (i.e., for example, HGL-0200, ONDA Corporation, Sunnyvale, Calif.) and preamplifier (i.e., for example, AG2010, ONDA) connected to a digital oscilloscope (i.e., for example, Waverunner 6051A, LeCroy, N.Y.). Axial positioning from the transducer was achieved by measuring the time delay between signal generation by the arbitrary wave generator. Any time delay between the wave generator and transducer was negligible. Signal detection by performed using a hydrophone, and was converted to a distance unit using the speed of sound at room temperature. Two-dimensional scans with spatial resolutions of 0.5 mm or higher of the acoustic field (at a generated pressure of 20% of that used for experiments) were acquired with an Acoustic Intensity Measurement System (i.e., for example, AIMS4.2.13, ONDA) inside an AIMS Scanning Tank (i.e., for example, ASTS01, ONDA). The hydrophone was then positioned at the point of maximum acoustic intensity, and waveforms were captured for various driving voltages. The acquired voltage was converted to transmitted acoustic pressure using the frequency-specific hydrophone sensitivity coefficient.

Figure 11B:
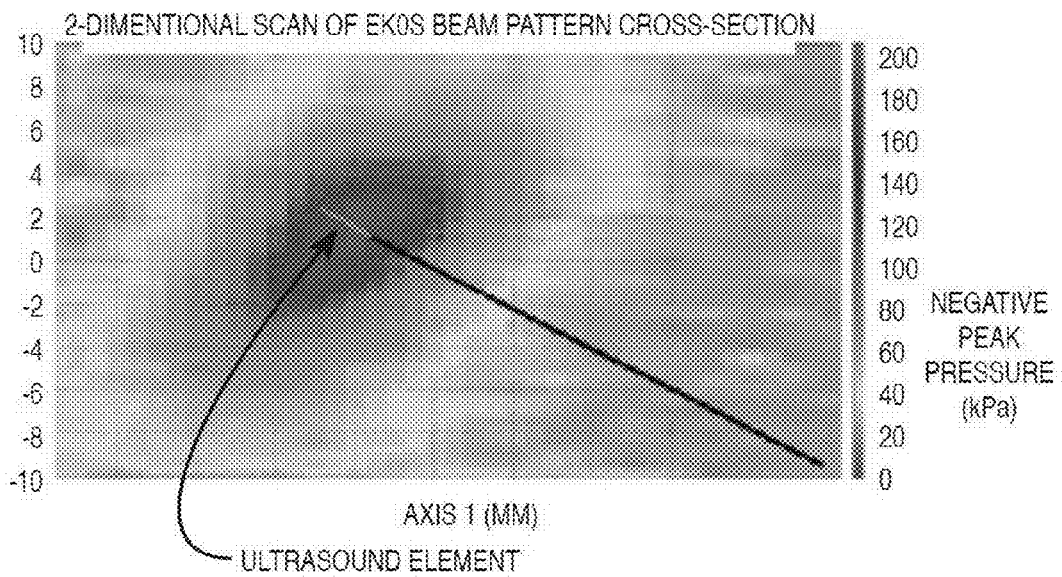
FIG. 11B presents exemplary data showing an acoustic power distribution for the catheter in FIG. 11A driven at 20% of maximal output at 2.1 mm from the active element.

A power map was derived where the hydrophone scanned in a plane located 2.1 mm from the catheter surface that simulated the distance of a coronary artery wall from an inserted catheter. See, FIG. 11B. The catheter was operated at 20% of the maximum voltage, generating up to 200 kPa directly opposite to the catheter. These data indicate that up to 1 MPa acoustic power can be applied at the level of the coronary artery wall if the catheter were to be inserted even in a relatively large 5 mm diameter artery (human coronaries are in the 2.5-5 mm range in diameter). It should be noted that the Ekos catheter operates at 1.7 MHz, which is close to the resonating frequency of the microbubbles used in our study (average radius 1.6±0.7 μm), maximizing the translation of acoustic energy to bubble motion.

VIII. Progenitor Cell-Tagged Microbubbles

In one embodiment, the present invention contemplates microbubbles that are tagged (i.e., for example, attached) with progenitor cells (i.e., for example, an endothelial progenitor cell) on the outside surface of the microbubble. The tagged progenitor cells are attached to the microbubble by a progenitor cell-specific ligand. In one embodiment, a microbubble outside surface displays a CD34 antibody as a progenitor cell-specific ligand. In one embodiment, the microbubble outside surface presents a CD133 antibody as a progenitor cell-specific ligand. In one embodiment, the microbubble outside surface presents a modified vascular endothelial growth factor (VEGF) as a progenitor cell-specific ligand. Although it is not necessary to understand the mechanism of an invention, it is believed that these ligands interact with their respective counterparts on the progenitor cell, thereby attaching the progenitor cell to the microbubble.

In one embodiment, the present invention contemplates a composition comprising an acoustically active microbubble tagged with an endothelial progenitor cells (EPCs), wherein the microbubbles display at least one EPC-specific ligand. In one embodiment, the EPC-specific ligand is selected from the group comprising a modified VEGF molecule, a monoclonal CD34 antibody, or a monoclonal CD133 antibody. In one embodiment, the microbubble encapsulates an acoustically active gas. Although it is not necessary to understand the mechanism of an invention, it is believed that the EPC-specific ligand provides an attachment point between the EPC and the microbubble. It is further believed that commercially available EPC-specific ligands provide sufficient affinity to attach personalized EPCs to microbubbles from any one of a number of patients.

In one embodiment, the present invention contemplates a method of making EPC tagged microbubbles comprising collecting a sample of blood from a patient and mixing the blood with the microbubbles comprising an EPC-specific ligand, wherein the microbubbles become attached to the EPCs. The microbubble-EPC complexes are then isolated by gravity sedimentation, while free floating (unattached) bubbles collect at the top of the sample. Alternatively, ultrasound radiation force can be used to separate the free-floating bubbles in a microfluidic chip (i.e., for example, by acustophoresis, supra).

Methods suitable for coupling progenitor cells to microbubbles have been reported. Hermanson, "Bioconjugate Techniques," Academic Press: New York, (1996); *In: Chemistry of Protein Conjugation and Cross-Linking* by S. S. Wong, CRC Press, (1993); and U.S. Patent Application Publication U.S. 2002/0102215 A1 to Klaveness et al., paragraphs 66 through 130; (the entire disclosures of which are incorporated herein by reference in their entirety for all purposes). Specific coupling methods include, but are not limited to, the use of bifunctional linkers, carbodiimide condensation, disulfide bond formation, and use of a specific binding pair, where one member of the pair is on the progenitor cell and the other is on the microbubble, e.g., a biotin-avidin interaction. Dayton et al., *J. Acoust. Soc. Am.* 112(5):2183-2192 (November 2002); and references 10 through 14 cited in the bibliography (Dayton et al., and internal references 10 through 14 are incorporated herein by reference in their entirety for all purposes). Alternatively, the use of charged phospholipids are advantageous in that they contain functional groups such as carboxyl or amino that permit linking of cell-specific ligands, if desired, by way of linking units.

A. Displacing Cell-Microbubble Complexes to Contact a Surface

The feasibility of using RF to displace cell-bubble complexes under relevant flow conditions was tested using an in vitro model having a transparent silastic tube placed under the objective of an upright fluorescence microscope. An external 10 MHz transducer was placed perpendicular to the flow direction, with the ultrasound energy focused in the same spot as the optical focus. The cells used in this study were human umbilical vein endothelial cells (HUVEC), labeled with a fluorescent cytoplasmic dye. Cationic microbubbles (zeta potential +80 mV) were used to non-specifically interact with the HUVECS, and cell-microbubble association was verified microscopically; negative-charged bubbles (zeta potential −90 mV) were used as controls. The passing of cells through the tube was recorded with a CCD camera. The cells were advanced through the vessel phantom at shear rates corresponding to systolic (low) and diastolic (high shear rate) coronary flow.

When applying RF (10 MHz, 1.2 MPa, 40% duty cycle for 5 sec), immediate marginalization and arrest of the circulating HUVECS was observed for both flow conditions when cationic microbubbles were mixed with the cells. See, FIG. 2C & FIG. 2F. No RF effect was obtained with cells alone. See, FIGS. 2A & 2D). Only a minimal effect was observed with negatively charged bubbles+HUVECs. See, FIGS. 2B & 2E. These data clearly show that RF can be effectively used to control cells motion under physiologic flow conditions.

B. Attaching Microbubble-Specific Cell Ligand Complexes to Progenitor Cells

In one embodiment, the present invention contemplates a method to isolate progenitor cells using microbubbles displaying progenitor cell-specific ligands. In one embodiment, the microbubble-ligand complexes isolate a specific progenitor cell (i.e., for example, an EPC) within a circulating fluid (i.e., for example, an in vivo cardiovascular system comprising blood). In one embodiment, a cell specific ligand VEGF 121 is displayed on the outer surface of a microbubble. VEGF 121 was been reported to bind to the EPC receptor, VEGFR2. (Rafii et al., "Therapeutic stem and progenitor cell transplantation for organ vascularization and regeneration" *Nat Med.* 9:702-712 (2003). VEGF 121 has less non-specific binding to heparin sulfates than other VEGF isoforms. VEGF 121-conjugated microbubbles were shown to specifically associate with a fraction of bone marrow mononuclear cells. See, FIG. 3.

VEGF microbubbles are expected to associate with circulating EPCs in vivo. To demonstrate such an association rats may be treated with subcutaneous GM-CSF to enrich the number of circulating EPCs. Subsequently, a suspension of fluorescently labeled VEGF-microbubbles can be injected via tail vein and allowed to circulate for 1 min. A sample of blood is then collected, and following RBC lysis, cell-microbubble association is determined. In vivo capture and delivery of progenitor cells, as contemplated in various embodiments of the present invention, provides tremendous advantages for therapeutics. For example, a simple injection of the microbubble-cell specific ligand complex into a patient will result in a therapeutic effect without administering a drug.

IX. Methods of Accelerating Biological Pathways

The present invention contemplates using acoustically active microbubbles and ultrasound radiation forces to facilitate progenitor cell contact with a target biological tissue. Further, the present invention contemplates methods providing acoustically directed delivery of personalized progenitor cell-microbubble complex to a biological tissue target. A personalized progenitor cell-microbubble complex comprises a progenitor cell that was collected and isolated from the same patient to which it is administered.

A stent or vascular graft coated with microspheres was reported that released biologically active agent(s) into the vessel wall to inhibit restenosis. This reference does not discuss the use of acoustic radiation forces or endothelial progenitor cells. Summers et al. "Compositions And Method For Making A Biodegradable Drug Delivery Stent," U.S. Pat. No. 5,980,551 (incorporated herein by reference).

The local delivery of blood-derived endothelial cells were observed to facilitate vascular healing. These results demonstrated that porcine endothelial cells labeled with endocytosed superparamagnetic iron oxide microbubbles are able to attach to magnetized stent struts implanted in porcine coronary and femoral arteries. The delivered cells were also distributed within the adjacent denuded vessel wall. Pislaru et al., "Magnetically Targeted Endothelial Cell Localization In Stented Vessels" *J. Am. Coll. Cardiol.* 48:1839-1845 (2006). This technology has the obvious disadvantages of extensive pre-therapy preparation and expense. In addition, the technology is inoperable when using non-magnetic stents that are very common in conventional medicine.

In one embodiment, the present invention contemplates a method providing a patient having undergone a stent implantation, an intravascular ultrasound (IVUS) probe, wherein the IVUS probe has been modified to emit quasi-continuous sonic energy at a frequency close to the resonating frequency of the bubbles, and microbubble-tagged EPCs. In one embodiment, the IVUS probe is placed at the site of the stent implantation. In one embodiment, the microbubble-tagged EPCs are released just proximal to the stented segment. In one embodiment, the microbubble-tagged EPCs are released through an IVUS probe port. In one embodiment, the microbubble-tagged EPCs are released from an over-the-wire angioplasty balloon. Although it is not necessary to understand the mechanism of an invention, it is believed that a circular field of radiation force is generated by the IVUS probe and directs the microbubble-tagged EPCs towards endothelial tissue. It is further believed that such a radiation force increases the likelihood of the microbubbles of contacting denuded endothelial tissue (i.e., for example, intimal tissue, or an injured artery wall). One distinct advantage of this embodiment over competing technologies (e.g., for example, a stent covered with CD34 antibodies) is that the released microbubble-tagged EPCs attach to the entire stent device in addition to the injured endothelial tissue (i.e., for example, an arterial vessel wall).

Although it is not necessary to understand the mechanism of an invention, it is believed that the coronary flow through a epicardial coronary vessel is about 30 ml/min. Upon making a conservative assumption that an exemplary procedure may provide an approximate 10% effectiveness, 5 minutes of IVUS treatment would be expected to seed a total of 15,000 EPCs on a stent surface. It is further believed that by extrapolating in vitro data showing that a seeding density of 5,000 cells/cm$^2$ of endothelial cells leads to a confluent cell culture in 5-7 days, this cell density should also be enough to seed a relatively large 3.5×30 mm stent (i.e., ~3 cm$^2$)

In one embodiment, the present invention contemplates a method comprising manipulating the location of microbubble-tagged EPCs in a fluid suspension. In one embodiment, the microbubble-tagged EPCs comprise gas-filled, acoustically active microbubbles, wherein the EPCs are attached to the microbubble surface by EPC-specific ligands. In one embodiment, acoustical forces (i.e., for example, ultrasonic radiation) direct the microbubble-tagged EPCs to contact an endothelial cell outer membrane. Although it is not necessary to understand the mechanism of an invention, it is believed that the EPC attached to the microbubble surface interacts with the endothelial cell outer membrane under conditions such that endothelialization is accelerated. Although it is not necessary to understand the mechanism of an invention, it is believed that the general concept is not limited to this therapeutic applications and may include other uses including, but not limited to, targeted drug delivery.

X. Cellular Therapy Delivery

In one embodiment, the present invention contemplates a method delivering a specific cell population to a biological tissue target (i.e., for example, a vascular tissue such as a myocardial) tissue. In one embodiment, the method provides an acoustically active microbubble comprising a stem cell specific ligand that is capable of attaching to a stem cell. In one embodiment, the method provides attaching the microbubble to the stem cell to form a stem cell-microbubble complex. In one embodiment, the method provides applying an acoustic radiation force to the stem cell-microbubble complex thereby increasing stem cell-microbubble contact with the myocardium tissue, wherein the stem cell retention is increased. In one embodiment, the stem cells are derived from a patient.

In one embodiment, the present invention contemplates a method for increasing the number of specific T-cell subsets at tumor sites. In one embodiment, the method provides an acoustically active microbubble comprising a specific T-cell ligand that is capable of attaching to a specific T-cell. In one embodiment, the method provides attaching the microbubble to the specific T-cell to form a specific T-cell-microbubble complex. In one embodiment, the method provides applying an acoustic radiation force to the specific T-cell-microbubble complex thereby increasing the specific T-cell-microbubble complex contact with a tumor site, wherein the number of specific T-cells increased at the tumor site. In one embodiment, the stem cells are derived from a patient.

XI. Cell Separation

In one embodiment, the present invention contemplates a method for separating different cell populations from a mixture. In one embodiment, the method provides an acoustically active microbubble comprising a cell-specific ligand that is capable of attaching to a specific cell population. In one embodiment, the method provides attaching the microbubble to the specific cell population to form a specific cell-microbubble complex. In one embodiment, the method provides applying an acoustic radiation force to the specific cell-microbubble complex wherein the specific cell-microbubble complex is separated from the mixture.

XII. Pharmaceutical Compositions

The present invention further provides pharmaceutical compositions comprising the microbubble embodiments described above. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Dosing is dependent on severity and responsiveness of the disease state to be treated, with the course of treatment lasting from several days to several months, or until a cure is effected or a diminution of the disease state is achieved. Optimal dosing schedules can be calculated from measurements of accumulation in the body of the patient. The administering physician can easily determine optimum dosages, dosing methodologies and repetition rates. Optimum dosages may vary depending on the relative potency and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations in bodily fluids or tissues. Following successful treatment, it may be desirable to have the subject undergo maintenance therapy to prevent the recurrence of the disease state, wherein maintenance doses can be administered, ranging from 0.01 µg to 100 g per kg of body weight, once or more daily, to once every 20 years.

XIII. Kits

In some embodiments, the present invention contemplates kits for the practice of the methods of this invention. The kits preferably include one or more containers containing a microbubble compatible with this invention. For example, the microbubble may have a cell-specific ligand attached to the outer shell. The kit can optionally include a medical device for the administration of the microbubble composition. Such medical devices include, but are not limited to, injection needles, catheters, and endoscopic devices. The kit can optionally include a pharmaceutically acceptable excipient and/or a delivery vehicle. The reagents may be provided suspended in the excipient and/or delivery vehicle or may be provided as a separate component which can be later combined with the excipient and/or delivery vehicle. The kit may optionally contain additional therapeutics to be co-administered with the microbubble complex.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in the preparation and administration of the microbubble complex. In particular the instructions provide how to obtain and isolate personalized progenitor cells from a patient for attachment to the provided microbubbles using the provided reagents. While the instructional materials typically comprise written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

EXPERIMENTAL

Example I

In Vitro Blood Vessel Phantom Model

An in vitro blood vessel phantom was made using a transparent poly(vinyl chloride) (PVC) tube (internal diameter 1 mm) placed in a water tank under the objective of a fluorescence microscope (BX51, Olympus) coupled to a CCD camera (ORCA, Hammamatsu). See, FIG. 1. The 5 MHz ultrasound transducer was immersed in the water nearly perpendicular to the flow direction, with the ultrasound energy focused in the same spot as the optical focus. MSCs were mixed with cationic microbubbles at different ratios (i.e., for example, MSC to microbubbles 1:12, 1:40, and 1:400). Control experiments were performed with MSCs mixed with neutrally charged microbubbles at 1:400 ratio. Mb-MSC complexes ($5 \times 10^4$) were diluted in PBS and advanced through the vessel phantom using a syringe pump (Harvard Apparatus) at flow rates resulting in wall shear stress of 0.53 and 4.27 Pa, approximating the coronary wall shear stress during systole and diastole, respectively. The sidewall of the vessel phantom opposite to the ultrasound transducer was continuously observed using fluorescence microscopy for 15 s while perfusing the phantom with mb-MSCs, with ultrasound being turned on for the middle 5 s of the experimental run. The number of cells adhering to the wall plus the number of cells slowing down or intermittently adherent (adherent+rolling fraction), as well as the number of cells still adherent 5 sec after the ultrasound was turned off (retained fraction) were counted off line, with the operator blinded to the MSC to microbubble mixture ratio.

Example II

Cell-Specific Microbubble Complexes and Tissue Imaging

VEGF 121 has been used for in vivo angiogenesis detection. (Lu et al., 2003). The present experiment tests whether cell-specific microbubble complexes can be used to image tissue in order to monitor healing and tissue regeneration.

Lipid microbubbles will be prepared from a lipid mixture consisting of distearoyl phosphocholine (PC), biotinylated distearoyl phosphoethanolamine (PE) tethered via polyethylene glycol (PEG), and PEG-stearate, dissolved in chloroform. The dried lipid mixture is re-hydrolyzed using saline and sonicated in the presence of perfluorobutane gas. The biotinylated PE in the bubble composition allows for the attachment of the ligand of interest via a streptavidin bridge. The bubble-cell association will be then tested using rat bone marrow derived EPCs expanded in culture to obtain a uniform cell preparation. Cell-bubble association will be quantified by microscopy by counting the number of microbubbles per cell. Variations in the microbubble composition will be tested, in particular the length of the PEG spacers in the microbubble lipids, to allow for optimal interaction between the VEGF and its ligand.

Once an optimal bubble composition is defined, the bubbles are tested with a suspension of freshly isolated rat mononuclear cells from the bone marrow and blood using a standard Ficoll gradient centrifugation. Bubble-cell complexes can be separated from the rest of the cells by their property to float due to the buoyancy of the microbubbles.

The isolated cells will be exposed to a brief ultrasound pulse at high mechanical index to destroy the bubbles, and then subjected to FACS analysis to explore the surface expression of CD34, CD133 and VEGFR2, markers specifically associated with EPCs.

Cell viability will be assessed by FACS after the cell-bubble mixture is exposed to the same RF energy to be used in vivo to detect possible detrimental effect of the acoustic energy on the cells.

Functional assays will be also conducted, where the cells will be plated and cultured in endothelium growth media on fibronectin surfaces and the number of EPC colonies counted after 2 week in culture.

The FACS and functional analysis will be compared to the unfractionated MNCs from the respective sources (blood and bone marrow). It is expected to obtain a significant enrichment of the EPCs using the VEGF-microbubble process described above.

Example III

Regeneration of Functional Endothelium Tissue

This example tests whether a cell-therapy improves endothelial coverage in an animal model of vascular injury.

A rat model of femoral injury is provided using a cutdown approach, wherein a small PE10 cannula is inserted via the femoral artery to the level of the iliacs in Wistar rats. Local vasoconstriction is induced with a high KCl solution. By advancing the catheter up and down a few times, effective de-endothelialization of the femoral segment is created without damage to the media (Lu et al., "A new method to denude the endothelium without damage to media: structural, functional, and biomechanical validation" *Am J Physiol Heart Circ Physiol.* 286:H1889-H1894 (2004). After the denudation, the cannula is removed and hemostasis obtained. The contralateral femoral is then cannulated using a 34 G microfill needle advanced to the level of the aortic bifurcation. This will serve as the cell injection port.

Microbubble-cell association will be performed ex vivo as described above. Subsequently, the microbubble-cell complex is then slowly injected into the rat while RF is applied to the denuded (i.e., injured) arterial segment. Cell adhesion to the injured segment can be verified at the end of the procedure using the same ultrasound setup in imaging mode. The cannula is then removed, and the animals allow to recover.

The rats will be sacrificed at 1 hr, 1 and 7 days, and the degree of endothelial coverage verified by histology and electron microscopy. Control studies will be performed to assess the normal endothelialization process and to set the appropriate follow up time points.

Several progenitor cell lines will be tested: In group A, cultured blood derived rat EPCs will be used. In group B, freshly isolated bone marrow derived MNCs will be tested. Importantly, both these cell lines will be used in an allogeneic fashion; it is believed that the small number of cells need to cover a short arterial segment will not induce a detrimental immune response. In these 2 groups, the cells will be allowed to associate with the VEGF-microbubbles in vitro prior to the injection. In group C, the VEGF microbubbles will be injected in the circulation and allowed to freely associate with circulating native EPCs.

Experiments will be divided into 4 subgroups, 1. control (no intervention following the arterial denudation). 2. microbubble control (using non-targeted bubbles only), 3. cells control, and 4. cells+microbubbles. RF treatment of the denuded femoral artery will be applied in subgroups 2, 3 and 4. Group C serves as VEGF bubbles-only control for groups A and B.

Example IV

Cell:Microbubble Associations by Flow Cytometry

Flow cytometry was performed to quantify microbubble-MSC association based on the observation that microbubble attachment to the MSC surface increases their side scatter as a consequence of the multiple reflective surfaces of the microbubbles present on the cells.

Rat MSC cells were washed and re-suspended in PBS at a concentration of $10^6$ cells/ml. Cationic microbubbles and control microbubbles (i.e., for example, anionic) were synthesized in accordance with Example XIII. The MSCs were fluorescently labeled with CMRA and mixed with increasing numbers of microbubbles. The cells were mixed with increasing ratios of cationic microbubbles (i.e., for example, 1:1, 1:40, and 1:400 microbubbles/cell). The mixtures were then analyzed using a flow cytometer (i.e., for example, BD FACSCalibur, Becton Dickinson) to characterize their SSC properties.

The photomultiplier amplification for each channel has been optimized in preliminary experiments. The microbubble-MSC complexes (mb-MSC) were gated in the forward side scatter/side scatter plot (FSC/SSC) based on their fluorescence, and their SSC was expressed relative to cell counts. The samples were placed on a microscopy slide, and DIC imaging using an inverted microscope (i.e., for example, Olympus IX81) was employed for direct quantification of the number of cells with bubbles, as well as the average number of bubbles per cell.

The number of cells with increased SSC (relative to MSCs alone) and the geometric mean of the SSC arbitrary units in this population were plotted against the proportion of MSCs with microbubbles on their surface and the average number of microbubbles per MSC, respectively, as quantified by microscopy. At least 20 cells were counted for each condition; data were analyzed with the operator blinded to the treatment assignment.

The proportion of cells with a change in SSC relative to baseline were plotted against the proportion of MSCs found to bear microbubbles by microscopy. A linear correlation between the two parameters was observed. The relative value of the SSC distribution was then used as a method to quantify the number of bubbles per cell. For example, a geometric average of the SSC signal was plotted against the average number of bubbles per MSCs as quantified by microscopy. A statistically significant linear correlation between the SSC characteristics and the cell:microbubble association was detected.

Further, it would be expected that the physical properties of MSCs are relatively preserved across species, as preliminary data indicate that rabbit and rat MSCs interact in a similar way with cationic bubbles.

Example V

Determination of Optimal Microbubble Number Per Cell

Cell:microbubble complexes were advanced through a 3 mm internal diameter vessel phantom (i.e., for example, a Silastic tube) and viewed under an Olympus IX81 inverted microscope coupled to a high sensitivity Hammamatsu EM CCD camera. See, FIG. 13.

MSC associations to a wall of the vessel phantom may be enhanced by coating the vessel with fibronectin. RF was applied using an EkoSonic SV 1.7 MHz transducer such that it is comparable to the preliminary in vivo data presented herein (supra). A Silastic tube was used because of its minimal echogenic properties. The optical focus of the microscope coincided with the ultrasound focus of the transducer. A long-working length low magnification objective (i.e., for example, an Olympus 4×) allowed for focused visualization of the middle portion of PVC tube opposite to the ultrasound transducer. The tube was connected to a Harvard Apparatus pump to allow for controlled flow of the cell:microbubble complexes through the vessel phantom.

MSCs was mixed with cationic microbubbles at increasing ratios (1:4, 1:12, 1:40, 1:120, 1:400), diluted to a concentration of $2.5 \times 10^3$ cells/ml and advanced through the tube using a Harvard pump at velocities chosen to simulate peak systolic and diastolic coronary shear stress respectively (0.5 and 4 Pa respectively). The parameters were comparable to the average shear rate in the human coronaries has been reported at 0.68 Pa. Doriot et al., "In-vivo measurements of wall shear stress in human coronary arteries" *Coron Artery Dis* 11:495-502 (2000). Controls comprised measuring MSCs alone, and MSCs mixed with neutrally charged bubbles at 1:400 cell:bubble ratio.

The pump causes the cells to flow through the vessel phantom while being visualized through the microscope and continuously recorded for 15 seconds. After 5 sec of microscopic observation during baseline flow, the RF was applied for 5 seconds, followed by 5 sec of observation post-ultrasound delivery. For each microbubble:cell complex mixture, a sample was analyzed using flow cytometry to determine the number of cells comprising bubbles, as well as the average number of bubbles per cell.

The number of adherent cells was quantified as the cells that adhere to a vessel wall surface during the RF application. Further, the number of cells that are still adherent to the vessel wall 5 sec after the RF was turned off was quantified (i.e., for example, fixed cells).

One embodiment of an experimental set-up schematic of the in vitro experiments is shown, wherein others are also possible. See, FIG. 13. The MSC:microbubble mixture is aspirated through the vessel phantom (pink) using a precision syringe pump. The EkoSonic SV catheter (blue) is placed inside the vessel phantom using a Tuhoy connector. The region adjacent to the active element of the catheter is over the objective of an inverted fluorescent microscope (Olympus IX81).

Each experiment was repeated 5 times. The adhered and fixed cells as quantified above were normalized to the number of cell bearing microbubbles passing by the area of interest in 5 sec and then plotted against the average number of bubbles per cell. An optimal concentration of bubbles per cell at which there is maximal cell adhesion to the vessel wall was determined.

Example VI

Determination of Cell:Microbubble Complex Toxicity

A systematic examination of cellular toxicity will be performed.

After mixing the cells with microbubbles, the cells may be incubated with Calcein AM (Invitrogen) at 1, 2 and 3 hrs to evaluate the number of viable cells. Calcein is internalized and becomes fluorescent only after hydrolysis by ubiquitous cellular enzymes present in live cells. The fluorescent cells (i.e., indicating the presence of live cells) will be counted and expressed as % of the total number of cells.

A more sensitive assay measuring lactate dehydrogenase (LDH) levels released by damaged cells can be performed using a CytoTox 96® Non-Radioactive Cytotoxicity Assay (Promega) according to the manufacturer instructions.

Functional assays will also be employed to also confirm that MSC manipulation using RF is not associated with significant toxicity. For these functional assays, cytometry flow experiments as described above will be performed under sterile conditions. A portion of the tube with adherent MSCs will be removed, submerged in a culture media (i.e., for example, 20% FBS alpha MEM), and incubated for 2 weeks at 37° C.

If significant cell toxicity is not present a confluent layer of cells is expected to form on the luminal surface of the tube. If significant cell toxicity is observed, the microbubble formulation can be altered. Microbubbles are synthesized at the University of Pittsburgh's Center for Ultrasound Molecular Imaging and Therapeutics and are capable of producing custom designed formulations based upon many parameters including, but not limited to, size, charge, acoustic responsiveness, or stability. For example, microbubbles comprising alternative lipids for the cationic moiety of the microbubble, such as 1,2-distearoyl-3-trimethylammonium propane (DSTAP) may be constructed. Soenen et al., "Addressing the problem of cationic lipid-mediated toxicity: the magnetoliposome model" *Biomaterials* 30(22):3691-3701 (2009). Alternatively, surface charges of a microbubble may be manipulated through choice of the cationic lipid and/or modulation of a cationic lipid concentration.

Further, if a microbubble charge interaction proves responsible for cell toxicity, specific targeting moieties can be attached to the cells. Custom designed targeted microbubbles that bind to cells through ligand-receptor interactions have been reported. Villanueva et al., "Myocardial ischemic memory imaging with molecular echocardiography" *Circulation* 115(3):345-352 (2007)

Example VII

Ex Vivo Measurement of Cell:Microbubble Adherence

Porcine coronary artery segments are used that have been isolated immediately ante-mortem. From each animal, a proximal 2 cm segment of the left anterior descending (LAD), left circumflex (LCx) and right coronary artery will be dissected free of adventitia; any visible branches will be ligated. The segments will be denuded by rolling them on an 18G needle.

The coronary segment will be then mounted in the perfusion setup. See, FIG. 13. The system will be perfused with heparinized blood obtained from the same animals at a fixed rate of 50 ml/min to emulate coronary flow rate; the outflow reservoir will be elevated to achieve a perfusion pressure of 100 mmHg. Rat MSCs will be fluorescently labeled and mixed with an optimal concentration of microbubbles as determined by methods described herein.

Three experimental groups (n=3-4 segments in each group) are designated for each animal: Group A: MSC alone; Group B: MSC-bubbles+RF; Group C: MSC-bubbles alone (no ultrasound). Even when RF is not used, the Ekos catheter will be left in place inside the coronary segment. The coronaries will be provided with 0.1 million cells over 1 min. Thereafter, the blood will be washed with warm MSC media, and the arterial segments will be incubated for 30 min at 37° C. to allow for stable cell adhesion to occur. Following this, the segments will be washed with PBS, perfusion fixed with 4% formalin, cut longitudinally and placed en-face on a microscopy slide.

Data Analysis and Expected Results

The number of fluorescent cells will be counted for each condition and reported as cell density per surface area. Comparisons among the 3 experimental groups will be performed using ANOVA, and if a significant difference is found ($p<0.05$), post hoc t-testing will be performed (two tailed) to determine where the difference resides, with appropriate corrections made for multiple comparisons.

Preliminary rabbit data indicate that RF facilitated cell adhesion is feasible in vivo in the presence of blood. See, FIG. 12. This set of experiments is expected to provide a quantitative measure of the effect of RF cell delivery relative to simply injecting the cells upstream in the circulation. MSCs are highly adherent cells, so a degree of MSC adhesion to the denuded arterial surface is expected to occur in the absence of RF. However, in vitro data using a PVC tube as a vessel phantom clearly demonstrate the superior efficacy of RF mediated cell delivery and adhesion, so at least a 10 fold increase in the delivery of cells to the vessel wall is expected using RF.

Example XIII

MSC Delivery in PCI-Induced Injured Swine

Domestic farm pigs (n=4) will be used in these acute experiments, with each animal serving as its own control. The animals will be anesthetized and intubated, and coronary angiography will performed as previously described. Toma et al., "Positive effect of darbepoetin on peri-infarction remodeling in a porcine model of myocardial ischemia-reperfusion" *J Mol Cell Cardiol.* 43(2):130-136 (2007). The animals will be pretreated with aspirin and anticoagulated with heparin for the duration of the procedure.

Figure 14:
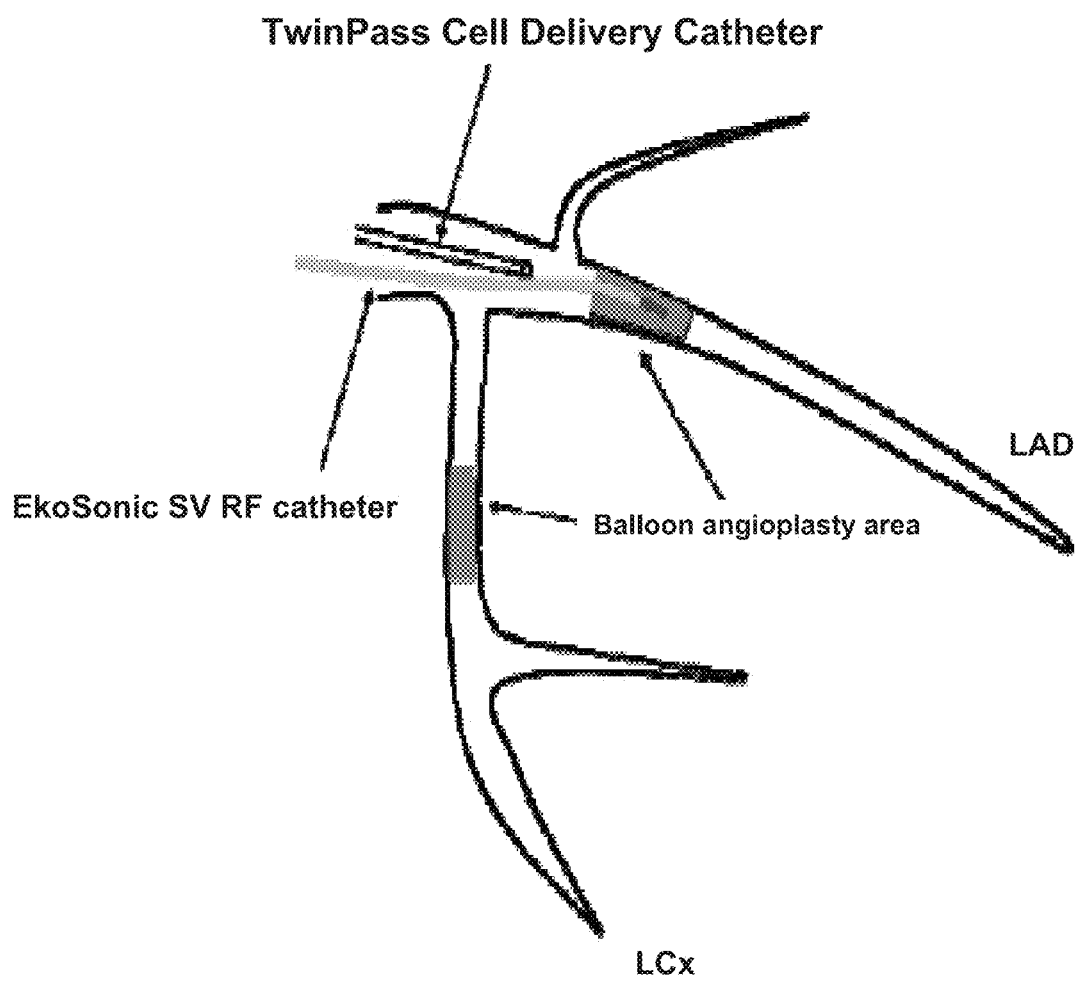
FIG. 14 presents one embodiment of an illustrative schematic for the in vivo delivery of cell-based therapies. For example, angioplasty arterial denuding may be performed in the LAD and the LCx. An EkoSonic SV catheter can be advanced to the level of an injured area in the LAD, and a cell:bubble mixture may be injected through a TwinPass catheter placed in the proximal LAD while applying RF. As a control, the same procedure may be repeated for the LCx, but without RF.

The experimental preparation is presented herein. See, FIG. 14. To denude the arterial endothelium, an angioplasty injury to the vessel wall will be created in the proximal circumflex artery (LCx) using a balloon inflated to 1.1 times the artery diameter 3 times for 30 seconds. A similar injury will be created in the mid section of the left anterior descending artery (LAD), using a diagonal branch as the proximal marker. The balloon catheter will be then removed and exchanged for an RF catheter transducer (i.e., for example, an EkoSonic SV™ endovascular catheter) which will be advanced to the distal end of the injured LAD segment. The guidewire will be removed.

A small dual lumen catheter (i.e., for example, a TwinPass catheter) will then be advanced to the proximal LAD for cell delivery. After priming this catheter, an optimized MSC: bubble suspension will be slowly injected into the LAD through the catheter at 0.1 million cells/ml/min for 10 min using an infusion pump. During the infusion, RF will be applied via the endovascular catheter using appropriate acoustic parameters, while the catheter is slowly manually withdrawn 1-2 mm every 1 min along the length of the angioplasty lesion.

Upon RF discontinuation, the endovascular catheter will be removed, and the infusion catheter repositioned in the LCx; the same number of bubble-labeled MSCs, taken from the same stock suspension used for the LAD infusion, will be injected in a similar manner directly into the LCx, but ultrasound will not be applied; this will serve as the control condition. The identical cells-microbubble preparation will be thus delivered in similar proportions to the LCx (which will serve as cell:bubble only control) and to the LAD, with only the LAD receiving ultrasound (RF plus cell:bubble).

Following the cell:bubble complex injections, the animals will remain sedated for 2 hrs to allow for the MSC to stabilize and adhere to the vessel surface. At the completion of the 2 hr period, the animals will be euthanized using pentobarbital overdose, the coronaries perfusion-fixed with 10% buffered formalin, and the injured segments dissected, cut longitudinally into 2 segments, and examined en face over the length of the lesion. One of the 2 segments will be placed face down on a slide and fluorescent cells will be counted and quantified per surface area. The second segment will be stained with an anti-CD45 antibody and a CD 14 antibody, using a FITC conjugated secondary antibody, to determine the number of leukocytes (CD45 positive cells) adhering to the vascular wall using routine indirect immunofluorescence techniques.

Example IX

Chronic Survival in Swine Treated with Acoustical RF Cell:Microbubble Therapy

Animal preparation and experimental design is in accordance with Example IX., with the main difference being that the animals will be recovered and followed for 2 weeks after stenting, and that a DES will be placed following angioplasty.

Pigs (n=8) will be prepared for coronary angiography as described. The animals will be treated with aspirin and heparin. Each animal will serve as its own control, with the LAD (n=4) or LCX (n=4) being the active vessel receiving RF+cells:bubbles in a given animal, and the opposite vessel being the control lesion representing the "standard of care" in the clinical setting (stent only).

Stenting will be performed in the LAD and the LCx using a 13-18 mm Taxus paclitaxel-eluting stent (Boston Scientific) with a stent/artery diameter ratio of 1.1; this is well established as a model of coronary injury in pigs. Schwartz et al., "Drug-eluting stents in preclinical studies; updated consensus recommendations for preclinical evaluation" *Circulation Cardiovasc Intern* 1:143-153 (2008). The stenting will be performed just distal to a first diagonal (or obtuse marginal) branches respectively, to allow for localization of the stented segment at autopsy. Following stent deployment, imaging IVUS will be performed to establish the baseline in vivo dimension of the vessel and lumen area in the injured segment on a standard 0.5 mm/s pullback.

Afterward, the IVUS catheter will be removed and the active lesion will receive direct selective infusion of MCS: bubble complexes into the appropriate coronary artery during simultaneous application of acoustic RF with an Ekos catheter. The dose of cells is optimized to provide at least a 50% coverage of the target area. The control stented lesion will receive neither cells nor ultrasound, emulating the routine clinical practice of coronary stenting with DES as the comparator experimental condition. Following the treatment, the sheath will be removed, hemostasis secured with direct manual pressure, and the animals allow to recover.

During recovery, the pigs will receive daily aspirin (81 mg daily) and clopidogrel (75 mg daily) for 2 weeks, and thereafter they will be returned to the fluoroscopy suite, anesthetized and intubated. A sheath will be percutaneously placed in the femoral artery, and coronary angiography will be performed to investigate the degree of restenosis. The treated segments will be re-examined next using intravascular ultrasound and again the vessel size and the luminal size will be measured according to clinical standards. Mintz et al., "American College of Cardiology Clinical Expert Consensus Document on Standards for Acquisition, Measurement and Reporting of Intravascular Ultrasound Studies (IVUS). A report of the American College of Cardiology Task Force on Clinical Expert Consensus Documents" *J Am Coll Cardiol.* 37(5):1478-1492 (2001).

Prior to euthanizing the animals, the coronaries will be perfused with Evans Blue, which stains the denuded area of the coronary artery. The animals will be quickly euthanized, and the coronaries will be perfused retrogradely at 100 mm Hg with saline to clear the blood, followed by fixation with formalin. The coronary segment containing the stent will be embedded in methyl-methacrylate to allow for preservation of the vessel morphology. The arteries will be cut transversely using a heavy-duty microtome, and the slides stained with hematoxylin-eosin and Movat-Pentachrome. At least 10 sections will be examined for each stent. The degree of inflammation, medial necrosis and thrombus presence will be quantified by an operator blinded to the treatment arm with a score of 1-3 assigned to each as previously described. Pendyala et al., "Endothelium-Dependent Vasomotor Dysfunction in Pig Coronary Arteries With Paclitaxel-Eluting Stents Is Associated With Inflammation and Oxidative Stress" *J. Am. Coll. Cardiol. Intv.* 2; 253-262 (2009). The presence and thickness of the neo-intima will be examined in relation to the stent struts (above struts and in-between struts).

In the last set of 3 animals from the group of 8, genetically modified MSCs expressing GFP will be used to allow for the tracking of the engrafted cells. For these experiments, a separate set of slides will be stained with rhodamine-tagged Griffonia Simplicifolia Lectin II (GSL II) at 1:100 dilution, which has previously been reported to label porcine endothelium. Toma et al., "Positive effect of darbepoetin on peri-infarction remodeling in a porcine model of myocardial ischemia-reperfusion" *J Mol Cell Cardiol.* 43(2):130-136 (2007). This will allow us to investigate whether the CMRA labeled surviving MSCs co-localize with the GSLII, thus demonstrating an endothelial phenotype differentiation of the MSCs.

Example X

Microbubble Synthesis

Cationic lipid microbubbles were made from a mixture of phosphatidylcholine, distearoyl-sn-glycero-3-ethylphosphocholine (DSEPC) and polyethylene glycerol stearate dissolved in chloroform. The solvent was evaporated by a stream of argon gas. Alternative polar lipids that may be used are 1,2-stearoyl-3-trimethylammonium-propane (chloride salt) (DOTAP) or 1,2-distearoyl-3-trimethylammonium propane (DSTAP). Residual chloroform was further removed under vacuum overnight at room temperature. The dried lipid mixture was re-hydrolyzed in normal saline and sonicated in the presence of perfluorocarbon gas. The DSEPC carries a quaternary ammonium ion, giving the microbubbles a cationic charge. Control bubbles had distearoyl-sn-glycero-3-phosphoethanolamine-N-biotinyl instead of the charged lipid. The average charge for the cationic bubbles is +55.2 mV, while the control bubbles have a negative charge of −18.6 mV. The MSCs have a surface charge of −23.6 mV. The average diameter of the microbubbles is approximately 2.5 microns.

The bubble concentration and size distribution were analyzed using a Multisizer 3 Coulter Counter (Beckman, Calif.). The electrical charge of the microbubbles and the cells was measured using a Zetasizer Nano-Zs90 (Malvern Instruments, UK). For the in vivo work, sterile microbubbles will be synthesized using the dedicated clean room available.

Example XI

Ultrasound Delivery System

The in vitro experiments were performed using a 5 MHz transducer (Model V326, Olympus NDT). For the in vivo studies, a 1.7 MHz intravascular ultrasound catheter (Ekosonic SV, Ekos Corp) was utilized. The transducers were driven with a waveform generator (Model 33250A, Agilent) coupled to a Power Amplifier (Model 100A250A, Amplifier Research). Both systems were driven with a 5 μs tone burst with a 25 μs pulse interval so the effective duty cycle was 20%. The ultrasound systems were calibrated in a water tank using a needle hydrophone (Model HGL-200, Onda Corp). The acoustic pressure at the focal point of the 5 MHz transducer was 1.2 MPa. The 1.7 MHz intravascular catheter was calibrated to generate 1 MPa (high radiation force) and 0.5 MPa (low radiation force) at 2 mm from the catheter surface.

Example XII

Mesenchymal Stem Cell (MSC) Cultures

Rat MSCs were used for in vitro experiments, while rabbit MSCs were employed for in vivo testing. MSCs were obtained from the mononuclear fraction of bone marrow of adult Sprague-Dawley rats or adult New Zealand rabbits, and expanded using 20% fetal calf serum in α-MEM supplemented with antibiotics and 2 mM L-glutamine. The non-adherent cells were washed away after 1 week in culture. The cells were then trypsinized at 2 weeks (passage 2) and split 1:2-4, and every 7-10 days thereafter before reaching confluence. MSCs were labeled with 0.5 μM Cell Tracker Orange (CMRA, Invitrogen) prior to use. The cells were gently trypsinized (0.02%) and allowed to interact with microbubbles in suspension in phosphate-buffered saline (PBS).

Example XIII

Mesenchymal Stem Cell Viability

For these experiments rat MSCs were used, and lethal exposure to hydrogen peroxide ($H_2O_2$) was used as a positive control. The MSCs were incubated in physiological buffered saline with cationic microbubbles at a 1:50 ratio for 1 hr, then labeled with a commercially available cell viability kit (i.e., for example, LiveDead®, Invitrogen, CA) according to the manufacturer's instructions, and examined after an additional 2 hrs.

Example IVX

In Vivo Aorta Studies

The animal studies described below were approved by the University of Pittsburgh Institutional Animal Care and Use Committee and complied with the PHS Policy on Humane Care and Use of Laboratory Animals. Adult New Zealand rabbits (3-4 kg weight) were sedated with intramuscular xylazine (7 mg/kg) and ketamine (40 mg/kg), intubated, and anesthetized with 1.5% inhaled isoflurane. The animals were treated with aspirin (100 mg rectally) and heparin (1000 U iv).

Vascular access was obtained in the right femoral and the left carotid arteries. To create areas of endothelial injury requiring treatment, an 4.5-5 mm angioplasty balloon was advanced under fluoroscopic guidance to the thoracic aorta and inflated in 3 separate aortic regions spanning T8 to L2 vertebral levels. An over-the-wire occlusion balloon was then advanced anterogradely via the carotid artery to the descending thoracic aorta, for use as a flow occluder and cell delivery catheter, while the Ekosonic ultrasound catheter was advanced via the femoral access to the denuded section of the aorta. See, FIG. 15A.

Rabbit MSCs were mixed with cationic microbubbles at a 1:40 ratio (mb:MSC) 1:40. The anterograde occlusion balloon was inflated, and the distal aorta was flushed with PBS for 30 s through the lumen of the balloon catheter distal to the occlusion, followed by 10 cc of serum-free media containing $3 \times 10^5$ mb-MSCs. The ultrasound was on for 3.5 min while gradually withdrawing the Ekosonic catheter over the length of the treatment area (i.e., for example, approximately 12-15 mm).

The 3 injury sites along the length of the descending aorta were randomly assigned to one of 3 treatment conditions: control (no ultrasound), low radiation force (0.5 MPa) and high radiation force (1 MPa). The occlusion balloon was then deflated (total occlusion time 5 min) to restore flow in the aorta, the rabbits were euthanized 20 min thereafter, and the aorta was perfusion fixed with 10% buffered formalin, dissected free, and examined en face by fluorescence microscopy. The number of adherent fluorescent MSCs were counted and the area of the aortic segment containing them was measured using a publicly available software package (i.e., for example, Image J, National Institutes of Health, Bethesda Md.).

To determine the persistence of radiation-force induced MSC adhesion, a single aortic endothelial injury lesion was created in a separate group of similarly instrumented rabbits, which were then treated with double the number of mb-MSC complexes and the high acoustic power radiation force protocol described above. The animals were allowed to recover and were euthanized at 3 (n=1) and 24 hours later (n=2), and the aortas were prepared as described above.

Example XV

Statistics

Data are expressed as mean±s.e.m. Experimental groups were compared using a non-parametric Kurskal-Wallis test to avoid assuming Gaussian distribution in these small samples. If significant differences were found (p<0.05), Dunn's test was performed post hoc to determine where they resided using a commercially available software package (Prism 5®, GraphPad).

We claim:
1. A method, comprising:
a) providing:
i) a microbubble:endothelial progenitor cell complex, wherein the microbubble attaches said cell via an endothelial progenitor cell-specific ligand, and
ii) an intravascular ultrasound probe capable of generating a radial acoustic radiation force, and
b) administering said complex to an injured vascular tissue and
c) inserting said intravascular ultrasound probe into said injured vascular tissue;
d) directing said microbubble:endothelial progenitor cell complex to said injured vascular tissue with said radial acoustic radiation force under conditions such that said complex adheres to said injured tissue.
2. The method of claim 1, wherein said method further comprises step (e) accelerating injured vascular tissue growth by said adhesion of said complex to said injured tissue.
3. The method of claim 1, wherein said microbubble is attached to the endothelial progenitor cell by said cell specific ligand.
4. The method of claim 1, wherein said injured vascular tissue is derived from tissue selected from the group consisting of a blood vessel tissue, an artery tissue, and a vein tissue.
5. The method of claim 1, wherein said endothelial progenitor cell is a personalized progenitor cell.
6. The method of claim 1, wherein said microbubble is filled with an acoustically active gas.
7. The method of claim 1, wherein said ligand is selected from the group consisting of a vascular endothelial growth factor (VEGF) molecule, a monoclonal CD34 antibody, and a monoclonal CD133 antibody.
8. The method of claim 1, wherein said administering comprises a route selected from the group consisting of oral, parenteral, intravenous, intradermal, intraperitoneal, intramuscular, and intranasal.
9. The method of claim 1, wherein said administering further comprises using a medical device.
10. The method of claim 9, wherein said medical device is selected from the group consisting of an injection needle and a catheter.
11. The method of claim 1, wherein said microbubble:endothelial progenitor cell complex comprises a ratio ranging between approximately 12:1 to 400:1.

* * * * *